(12) United States Patent
Elia et al.

(10) Patent No.: US 11,304,878 B2
(45) Date of Patent: *Apr. 19, 2022

(54) NUTRITIONAL SUPPORT FEEDING EFFICIENCY

(71) Applicant: ART MEDICAL Ltd., Netanya (IL)

(72) Inventors: Liron Elia, Kiryat-Ata (IL); Gavriel J. Iddan, Haifa (IL)

(73) Assignee: ART MEDICAL Ltd., Netanya (IL)

(*) Notice: Subject to any disclaimer, the term of this patent is extended or adjusted under 35 U.S.C. 154(b) by 0 days.

This patent is subject to a terminal disclaimer.

(21) Appl. No.: 17/334,864

(22) Filed: May 31, 2021

(65) Prior Publication Data

US 2021/0283021 A1  Sep. 16, 2021

Related U.S. Application Data

(63) Continuation of application No. 16/808,699, filed on Mar. 4, 2020, now Pat. No. 11,020,322, which is a
(Continued)

(51) Int. Cl.
*A61J 15/00* (2006.01)

(52) U.S. Cl.
CPC .................. *A61J 15/0084* (2015.05)

(58) Field of Classification Search
CPC .............. A61J 15/0076; A61J 15/0084; A61M 2005/14208; A61M 2005/1726;
(Continued)

(56) References Cited

U.S. PATENT DOCUMENTS

2009/0210368 A1  8/2009  Deo et al.
2011/0112429 A1  5/2011  Stuebe et al.
(Continued)

FOREIGN PATENT DOCUMENTS

WO  WO 2018/104888  6/2018
WO  WO 2018/185738  10/2018
WO  WO 2020/178833  9/2020

OTHER PUBLICATIONS

International Search Report and the Written Opinion dated Jul. 6, 2020 From the International Searching Authority Re. Application No. PCT/IL2020/050256. (21 Pages).
(Continued)

*Primary Examiner* — Alan Chen
*Assistant Examiner* — Brent Johnston Hoover

(57) ABSTRACT

There is provided a method comprising: computing a target nutritional goal to reach at an end of a time interval based on a real time energy expenditure of a patient, wherein the target nutritional goal comprises a volume to be delivered (VTBD) by the end of the time interval corresponding to a target amount of energy expenditure of the patient over the time interval, computing a target feeding profile defining a target feeding rate for enteral feeding of the patient for reaching the VTBD by the end of the time interval, continuously monitoring the real time energy expenditure, adapting the target nutritional goal and corresponding VTBD to compute a maximum VTBD to reach at the end of the time interval according to the monitoring, and dynamically adapting the target feeding rate and the corresponding target feeding profile for a remaining portion of the time interval for reaching the maximum VTBD.

20 Claims, 29 Drawing Sheets

Related U.S. Application Data continuation-in-part of application No. 16/291,127, filed on Mar. 4, 2019, now Pat. No. 10,682,288.

(58) Field of Classification Search
CPC .... A61M 2205/3334; A61M 2205/502; A61M 2205/581; A61M 5/14232; A61M 5/16836; A61M 5/1684; A61M 5/16854
See application file for complete search history.

(56) References Cited

U.S. PATENT DOCUMENTS

| | | | |
|---|---|---|---|
| 2015/0332490 A1 | 11/2015 | Coulmeau et al. | |
| 2016/0058673 A1* | 3/2016 | Francis | G16H 20/17 604/65 |
| 2016/0143817 A1* | 5/2016 | Elia | A61B 5/4238 604/503 |
| 2018/0078195 A1 | 3/2018 | Sutaria et al. | |
| 2018/0161249 A1 | 6/2018 | Elia et al. | |
| 2019/0083725 A1 | 3/2019 | Elia et al. | |
| 2020/0281819 A1 | 9/2020 | Elia et al. | |

OTHER PUBLICATIONS

Invitation to Pay Additional Fees, Communication Relating to the Result of the Partial International Search and the Provisional Opinion dated May 15, 2020 From the International Searching Authority Re. Application No. PCT/IL2020/050256. (12 Pages).
Notice of Allowance dated Feb. 3, 2021 From the US Patent and Trademark Office Re. U.S. Appl. No. 16/808,699. (17 Pages).
Notice of Allowance dated Feb. 10, 2020 From the US Patent and Trademark Office Re. U.S. Appl. No. 16/291,127. (8 pages).
Official Action dated Sep. 16, 2019 From the US Patent and Trademark Office Re. U.S. Appl. No. 16/291,127. (51 Pages).
Official Action dated Sep. 17, 2020 from the US Patent and Trademark Office Re. U.S. Appl. No. 16/808,699. (33 pages).
Bendavid et al. "NutritionDay ICU: A 7 Year Worldwide Prevalence Study of Nutrition Practice in Intensive Care", Clinical Nutrition, 36(4): 1122-1129, Published Online Aug. 9, 2016.
Casaer et al. "Early Versus Late Parenteral Nutrition in Critically Ill Adults", The New England Journal in Medicine, 365(6): 506-517, Aug. 11, 2011.
Dvir et al. "Computerized Energy Balance and Complications in Critically Ill Patients: An Observational Study", Clinical Nutrition, 25(1): 37-44, Feb. 2005.
Harvey et al. "Trial of the Route of Early Nutritional Support in Critically Ill Adults", The New England Journal of Medicine, 371(18): 1673-1684, Published Online Oct. 1, 2014.
Heyland et al. "Nutrition Support in the Critical Care Setting: Current Practice in Canadian ICUs—Opportunities for Improvement?", Journal of Parenteral and Enteral Nutrition, 27(1): 74-83, Jan.-Feb. 2003.
Jenkinson et al. "Symptoms and Endoscopic Findings—Can they Predict Abnormal Nocturnal Acid Gastrooesophageal Reflux?", Annals of the Royal College of Surgeons of England, 71(2): 117-119, Mar. 1989.
Reignier et al. "Effect of Not Monitoring Residual Gastric Volume on Risk of Ventilator-Associated Pneumonia in Adults Receiving Mechanical Ventilation and Early Enteral Feeding. A Randomized Controlled Trial", Journal of the American Medical Association, JAMA, 309(3): 249-256, Jan. 16, 2013.
Reignier et al. "Enteral Versus Parenteral Early Nutrition in Ventilated Adults With Shock: A Randomised, Controlled, Multicentre, Open-Label, Parallel-Group Study (NUTRIREA-2)", The Lancet, 391(10116): 133-143, Published Online Nov. 8, 2017.
Shiraishi et al. "Validation of a Prognostic Calculator for Prediction of Early Vesicoureteral Reflux Resolution in Children", The Journal of Urology, 182: 687-691 , Aug. 2009.
Singer et al. "ESPEN Guideline on Clinical Nutrition in the Intensive Care Unit", Clinical Nutrition, 38(1): 48-79, Published Online Sep. 29, 2018.
Tatucu-Babet et al. "The Prevalence of Underprescription or Overprescription of Energy Needs in Critically Ill Mechanically Ventilated Adults as Determined by Indirect Calorimetry: A Systemic Literature Review", Journal of Parentral and Enteral Nutrition, 40(2): 212-225. Published Online Jan. 20, 2015.
Wischmeyer et al. "Winning the War Against ICU-Acquired Weakness: New Innovations in Nutrition and Exercise Physiology", Critical Care, 19(Suppl.3): S6-1-S6-14, Published Online Dec. 18, 2015.
Zusman et al. "Predictive Equations Versus Measured Energy Expenditure by Indirect Calorimetry: A Retrospective Validation", Clinical Nutrition, 22 P., Published Online May 8, 2018.
Zusman et al. "Resting Energy Expenditure, Calorie and Protein Consumption in Critically Ill Patients: A Retrospective Cohort Study", Critical Care, 20(367): 1-8, Nov. 10, 2016.

* cited by examiner

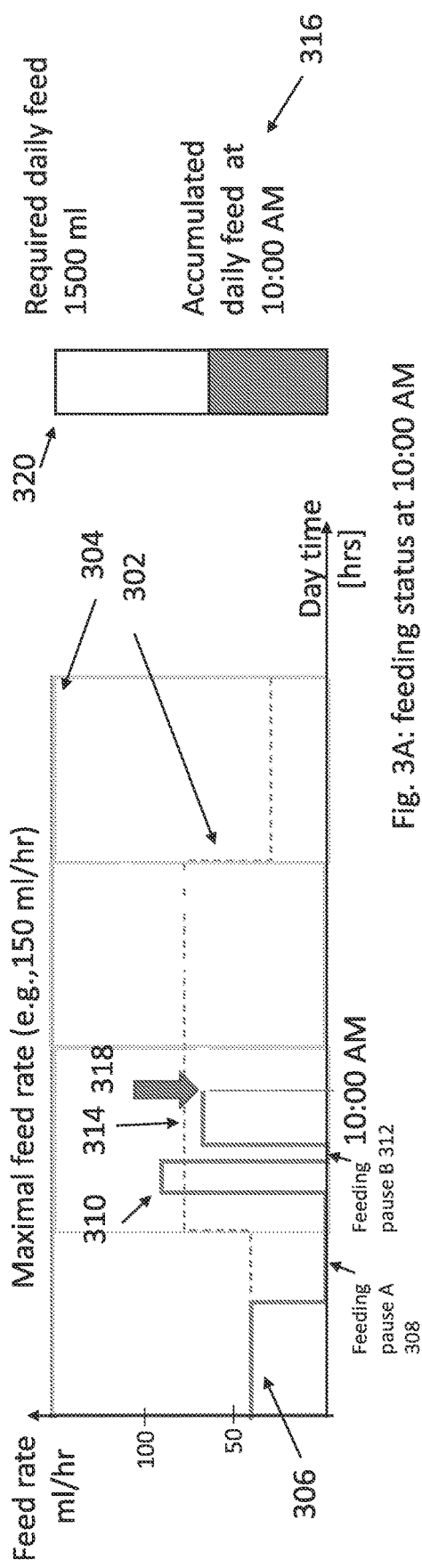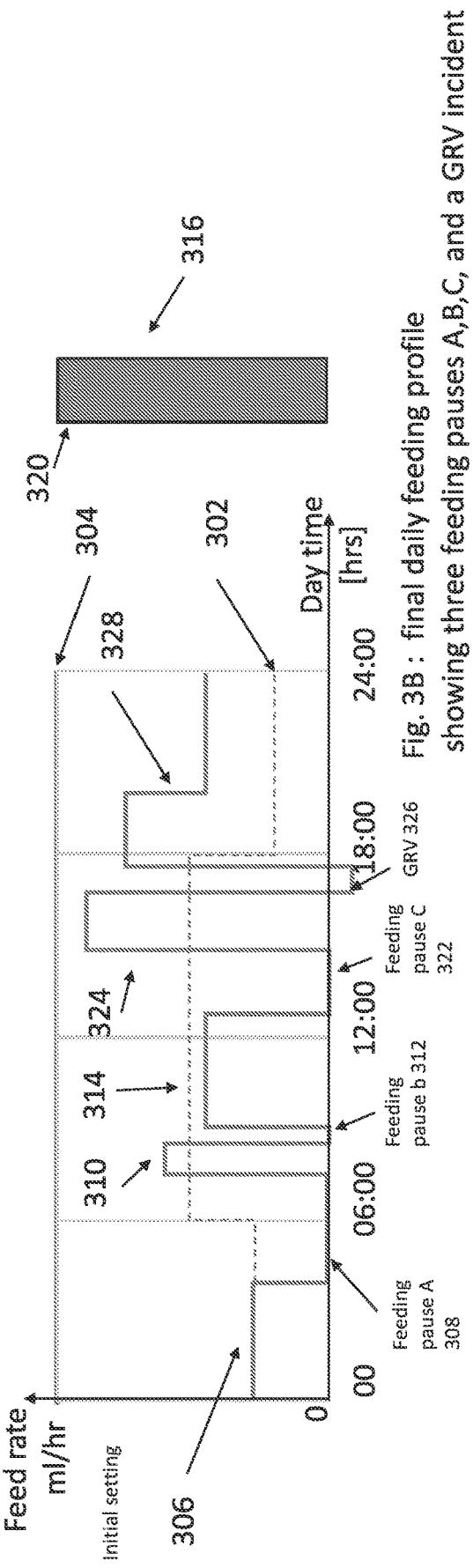

Measured parameters
Total GRV weight ——— $W_t$ [gram]
Total GRV volume ——— $V_t$ [ml]
a-priori known data Food density ——— $\rho \left[\frac{gram}{ml}\right]$  *known from formula data*

*Calculating the volume of lost food $V_f$ [ml] for future make up.*

Using the weight balance equation:

$$V_f \cdot \rho + (V_t - V_f) = W_t$$

We get:

$$V_f = \frac{W_t - V_t}{\rho - 1}$$

FIG. 4 showing the results of the N patient reflux events associated with reflux-related parameters m vis a vis accumulated learned results (uniform showing the ranges of the N reflux-related parameters associated with reflux event m vis a vis accumulated learned results (normal distribution) having means

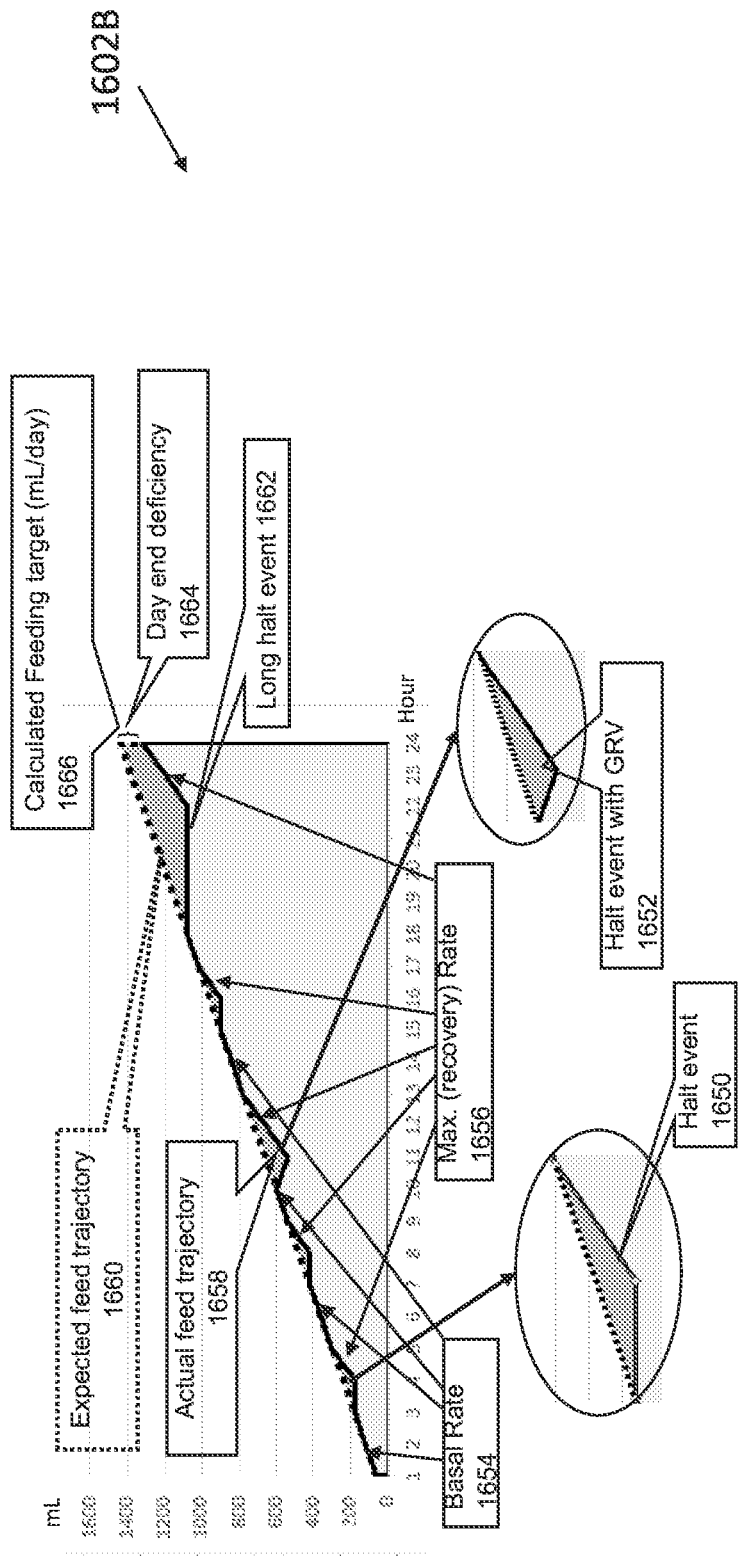
Fig. 15B: A more detailed nutritional daily chart

NUTRITIONAL SUPPORT FEEDING EFFICIENCY

RELATED APPLICATIONS

This application is a continuation of U.S. patent application Ser. No. 16/808,699, filed on Mar. 4, 2020, which is a Continuation-in-Part (CIP) of U.S. patent application Ser. No. 16/291,127 filed on Mar. 4, 2019, now U.S. Pat. No. 10,682,288. The contents of the above applications are all incorporated by reference as if fully set forth herein in their entirety.

This application is related to International Patent Application No. PCT/IL2017/051271 (published as WO2018/185738), titled "SYSTEMS AND METHODS FOR DYNAMIC CONTROL OF ENTERAL FEEDING ACCORDING TO ENERGY EXPENDITURE", and U.S. patent application Ser. No. 15/614,641, titled "SYSTEMS AND METHODS FOR AUTOMATIC MANAGEMENT OF REFLUX DURING ENTERAL FEEDING", U.S. patent application Ser. No. 16/000,922, titled "SYSTEMS AND METHODS FOR TRACKING SPONTANEOUS BREATHING IN A MECHANICALLY VENTILATED PATIENT", U.S. patent application Ser. No. 15/614,641, titled "SYSTEMS AND METHODS FOR AUTOMATIC MANAGEMENT OF REFLUX DURING ENTERAL FEEDING", International Patent Application No. PCT/IB2017/057702 (published as WO2018/104888), titled "SYSTEMS AND METHODS FOR SENSING LUNG FLUID", U.S. patent application Ser. No. 15/228,115, titled "POINT OF CARE URINE ANALYZER", by the same inventors as the present application, the contents of which are incorporated herein by reference in their entirety.

FIELD AND BACKGROUND OF THE INVENTION

The present invention, in some embodiments thereof, relates to treatment of a patient and, more specifically, but not exclusively, to systems and methods for treatment of a patient by automated patient care.

Certain patients require assistance with feeding via an enteral approach, require assistance with breathing, and/or require assistance with urination, for example, patients in the intensive care unit (ICU) which may be sedated and/or intubated. Current approaches are based on a manual assessment (e.g., by a nurse, physician), and are limited in their ability to provide optimal settings for the patient. Medical outcomes of patients may be improved by better control of enteral feeding, breathing, and/or urination.

Recent studies suggest that nutritional guidelines across the majority of intensive care units (ICUs) are not being implemented, for example, as described with reference to Bendavid I, Singer P, Theilla M, et al. (2017) *Nutrition Day ICU: a 7-year worldwide prevalence study of nutrition practice in intensive care. Clin Nutr* 36:1122-1129, and Heyland D K, Schroter-Noppe D, Drover J W, Jain M, Keefe L, Dhaliwal R, *Day A* (2003) *Nutrition support in the critical care setting: current practice in Canadian ICUs—opportunities for improvement? J Parenter Enteral Nutr.* 27:74-83. Lack of knowledge, no technology to support medical staff, and general noncompliance with nutritional guidelines result in higher mortality and infection complications.

One of the main pitfalls is the common use of predictive equations like Harris-Benedict equations for targeting energy prescription in critical illness. The equations have been demonstrated by many, for example, as described with reference to Zusman O, Kagan I, Bendavid I, Theilla M, Cohen J, Singer P (2018) *Predictive equations Predictive Equations versus Measured Energy Expenditure by Indirect calorimetry: A Retrospective Validation. Clin Nutr* (Article in Press, and Tatucu-Babet O A, Ridley E J, Tierney A C (2015) *The prevalence of underprescription or overprescription of energy needs in critically ill mechanically ventilated adults as determined by indirect calorimetry: a systematic literature review. JPEN J Parenteral Enteral Nutr* 40:212-225, to be inaccurate in more than 50% of the cases, leading to under or over nutrition. In case of too low a target, patients will be underfed and, since the process is progressively increasing the rate of administration, calorie balance will reach large negative values that are associated with increased morbidity, for example, as described with reference to Dvir D, Cohen J, Singer P (2005) *Computerized energy balance and complications in critically ill patients: an observational study. Clin Nutr* 25:37-44.

Providing higher calories target that is needed has been found to be associated with increased mortality, for example, as described with reference to Zusman O, Theilla M, Cohen J, Kagan I, Bendavid I, Singer P (2016) *Resting energy expenditure, calorie and protein consumption in critically ill patients: a retrospective cohort study. Crit Care* 20:367, resulting in recommendations by ESPEN to measure energy expenditure in a rested condition [REE], for example, as described with reference to Singer P, Reintam Blaser A, M Berger M M, Alhazzani W, Calder P C, Casaer M (2018) *ESPEN guideline on clinical nutrition in the intensive care unit. Clin Nutr Epub ahead of publication.*

SUMMARY OF THE INVENTION

According to a first aspect, system for automated enteral feeding of a patient, comprises: at least one processor executing a code for: monitoring a plurality of gastric reflux-related parameters and at least one gastric reflux event while the patient is automatically enterally fed by an enteral feeding controller according to a baseline feeding profile including a target nutritional goal, training a classifier component of a model for predicting likelihood of a future gastric reflux event according to an input of scheduled and/or predicted plurality of gastric reflux-related parameters, the classifier trained according to computed correlations between the plurality of gastric reflux-related parameters and the at least one reflux event, feeding scheduled and/or predicted gastric reflux-related parameters into the trained classifier component of the model for outputting risk of likelihood of a future gastric reflux event, and computing, by the model, an adjustment to the baseline feeding profile for reducing likelihood of the future gastric reflux event and for meeting the target nutritional goal.

In a further implementation form of the first aspect, the plurality of reflux-related parameters are members selected from the group consisting of: time of day of the reflux event, enteral feeding rate during the reflux event, patient location change prior to the reflux event, and medication administered prior to the reflux event.

In a further implementation form of the first aspect, the patient location change is detected by a member selected from the group consisting of: scheduled event requiring patient location change extracted from an electronic health record (EHR) of the patient, an analysis of images captured by a camera monitoring the patient, and an analysis of inertial signals outputted by inertial sensors.

In a further implementation form of the first aspect, the monitoring is performed over a time interval for which a risk of likelihood of the future reflux event was previously predicted and the adjustment to the baseline feeding profile was previously computed, the training is performed for the time interval for updating the trained classifier, and the feeding is performed based on the updated trained classifier for outputting an a new and/or updated risk of likelihood of the future reflux event, and the adjustment is computed based on the new and/or updated risk.

In a further implementation form of the first aspect, the adjustment to the baseline feeding profile comprises an adjustment to a baseline feeding rate delivered by a pump by adjusting at least one member of the group consisting of: a stroke rate of the pump, and a stroke amplitude of the pump.

In a further implementation form of the first aspect, further comprising: iterating the monitoring, the training, the feeding, and the computing, wherein: monitoring is for accumulating data indicative of the plurality of reflux-related parameters and at least one reflux event, training is for dynamically updating the trained classifier based on the accumulated data, feeding is iterated for previously processed and/or new scheduled and/or predicted reflux-related parameters, and the computing the adjustment is dynamically performed according to dynamically predicted likelihood of future reflux event.

In a further implementation form of the first aspect, the at least one reflux event is associated with a plurality of reflux-event parameters, and the classifier is trained for prediction of likelihood of the future reflux event based on computed correlations between the plurality of reflux-related parameters and the plurality of reflux-event parameters.

In a further implementation form of the first aspect, the at least one reflux event is defined as a requirement of the plurality of reflux-event parameters.

In a further implementation form of the first aspect, the plurality of reflux-event parameters are members selected from the group consisting of: reflux duration, reflux amount.

In a further implementation form of the first aspect, when the risk of likelihood of the future reflux event denotes a likely occurrence of the future reflux event, the adjustment comprises a reduction in feeding rate, and when the risk of likelihood of the future reflux event denotes an unlikely occurrence of the future reflux event, the adjustment comprises an increase in feeding rate.

In a further implementation form of the first aspect, the increase in feeding rate is limited by a maximal feeding rate computed according to a risk of likelihood of future reflux event below a requirement for no scheduled and/or predicted reflux-related parameters.

In a further implementation form of the first aspect, the reduction and increase in feeding rate are proportion to the risk of likelihood of the future reflux event.

In a further implementation form of the first aspect, the reduction and increase in feeding rate are performed in constant predefined amounts.

In a further implementation form of the first aspect, the reduction and increase in feeding rate are computed according to a set of rules based on the computed the risk of likelihood of the future reflux event.

In a further implementation form of the first aspect, further comprising: detecting a reflux event by the monitoring while the patient is enterally fed according to a feeding rate of the baseline feeding profile, pausing the enteral feeding by the enteral feeding controller for a pause time interval, adjusting the baseline feeding profile by reducing the feeding rate, and resuming the enteral feeding after the pause time interval and the reduced feeding rate.

In a further implementation form of the first aspect, further comprising: updating the training of the classifier according to computed correlations between the plurality of reflux-related parameters associated with the detected reflux event, and the detected reflux event, re-outputting risk of likelihood of the future reflux event, wherein the feeding rate is reduced according to the re-outputted risk.

In a further implementation form of the first aspect, the baseline feeding profile is defined over a time interval, and the target nutritional goal denotes an accumulation of enteral feeding parameters to reach at an end of the time interval.

In a further implementation form of the first aspect, further comprising: computing at the end of the time interval, a nutritional difference between the accumulation of enteral feeding parameters and the target nutritional goal, and generating instructions for parenteral feeding of the patient according to the difference.

In a further implementation form of the first aspect, the reflux-related parameters and the at least one reflux event are time stamped, and wherein the correlations are computed between the plurality of reflux-related parameters and the at least one reflux event having time stamps falling within a common time window.

In a further implementation form of the first aspect, the correlations are iteratively computed by sliding the common time window.

In a further implementation form of the first aspect, the common time window is about 15 minutes.

In a further implementation form of the first aspect, the plurality of reflux-related parameters denote a time within a repeating physiological cycle, the correlation is performed between the at least one reflux event and the time within the repeating physiological cycle, and the risk of likelihood of future reflux event is based on a current time with respect to the repeating physiological cycle.

In a further implementation form of the first aspect, the adjustment to the baseline feeding profile includes an adjustment of at least one of: water and medication for enteral delivery, at a defined time of day.

According to a second aspect, a system for automated patient care, comprises: at least one processor executing a code for: monitoring, over a monitoring interval, a plurality of patient-related parameters, a plurality of enteral delivered substances, and a plurality of gastric reflux-event parameters obtained while the patient is automatically enteral fed by an enteral feeding controller according to a baseline feeding profile including a target nutritional goal, creating a training dataset by computing a plurality of feature vectors each associated with an indication of time during the monitoring interval, each feature vector storing the plurality of patient-related parameters, the plurality of enteral delivered substances, and the plurality of gastric reflux-event parameters, training a model adapted to receive current patient-related parameters and output instructions for adjustment of the enteral delivered substances for reducing likelihood of a future gastric reflux event, the model trained according to the training dataset based on computed correlations between the plurality of patient-related parameters, the plurality of enteral delivered substances, and the plurality of gastric reflux-event parameters, and feeding current patient-related parameters into the trained model for outputting instructions for adjustment of the enteral delivered substances for reducing likelihood of a future reflux event.

In a further implementation form of the second aspect, the plurality of patient-related parameters are selected from the group consisting of: patient demographics, patient age, patient gender, current patient medical diagnosis, past patient medical history, current patient signs and/or symptoms, patient vital signs, patient urine data, patient calorimetry data, enteral feeding rate, patient location changes, blood test values, urinalysis test values, urine output, lung function parameter values, lung fluid level, enteral administration of a bolus, and SpO2.

In a further implementation form of the second aspect, the enteral delivered substances are selected from the group consisting of: enteral feeding formula, water, and medication.

In a further implementation form of the second aspect, the reflux-event parameters are selected from the group consisting of: time of day of the reflux event, volume of reflux, intensity of reflux, duration of reflux, weight of reflux.

In a further implementation form of the second aspect, the adjustment comprises entering a medication phase when administration of medication is indicated by halting feeding for a predefined time interval for reducing likelihood of reflux.

In a further implementation form of the second aspect, the monitoring, the creating, and the training are iteratively performed for the time interval during which the enteral delivered substances are adjusted.

According to a third aspect, a system for generating instructions for adjustment of at least one of a mechanical ventilator and fluid balance of a patient, comprises: at least one hardware processor executing a code for: monitoring, over a monitoring interval, output of a plurality of sensors located on a feeding tube positioned for enteral feeding of the patient, a plurality of ventilation-related parameters denoting adjustable settings of the mechanical ventilator, and a plurality of fluid-related parameters denoting adjustment of the fluid balance of the patient, obtained while the patient is automatically enteral fed via the feeding tube, creating a training dataset by computing a plurality of feature vectors each associated with an indication of time during the monitoring interval, each feature vector storing features computed from the output of the plurality of sensors located on the feeding tube, the plurality of ventilation-related parameters, and the plurality of fluid-related parameters, training a model adapted to receive current outputs of the plurality of sensors located on the feeding tube and output instructions for adjustment of at least one of the plurality of ventilation-related parameters of the mechanical ventilator that automatically ventilates the patient and the plurality of fluid-related parameters denoting adjustment of a fluid balance of the patient, the model trained according to the training dataset based on computed correlations between the output of the plurality of sensors located on the feeding tube, the plurality of ventilation-related parameters, and the plurality of fluid-related parameters, and feeding current outputs of the plurality of sensors located on the feeding tube into the trained model for outputting instructions for adjustment of the plurality of ventilation-related parameters of the mechanical ventilator, and adjustment of the plurality of fluid-related parameters for fluid balance of the patient for obtaining at least one member of the group consisting of: at least one target patient-breathing parameter and at least one target patient-fluid parameter.

In a further implementation form of the third aspect, the monitoring further comprises monitoring at least one patient-breathing parameter and at least one patient-fluid parameter, wherein the feature vector of the training dataset further includes features computed from the at least one patient-breathing parameter and at least one patient-fluid parameter, wherein the model is trained to receive current at least one patient-breathing parameter and at least one patient-fluid parameter based on computed correlations between the at least one patient-breathing parameter, the at least one patient-fluid parameter, the output of the plurality of sensors located on the feeding tube, the plurality of ventilation-related parameters, and the plurality of fluid-related parameters, wherein the feeding comprise feeding current values of the at least one patient-breathing parameter and the at least one patient-fluid parameter.

In a further implementation form of the third aspect, the at least one patient-breathing parameter is selected from the group consisting of: SpO2, impedance sensors output, wherein the at least one patient-fluid parameter is selected from the group consisting of: administration of diuretic medication, administration of antidiuretic medication, amount of urine outputted, time of urine output, concentration of urine output, and amount of fluid in lungs.

In a further implementation form of the third aspect, the at least one target patient-breathing parameter is selected from the group consisting of: SpO2, impedance sensors output, wherein the at least one target patient-fluid parameter is selected from the group consisting of: amount of urine outputted over a time interval, concentration of urine output, and amount of fluid in lungs.

In a further implementation form of the third aspect, the output of the plurality of sensors comprises at least one feature computed based on the output of the plurality of sensors, the at least one feature selected from the group consisting of: estimate of amount of fluid in at least one lung of the patient, and estimate of spontaneous diaphragm movement of the patient.

In a further implementation form of the third aspect, the plurality of fluid-related parameters are selected from the group consisting of: administration of diuretic medication, administration of antidiuretic medication, administration of intravenous fluid administration, amount of enteral fluid administration, and type of fluid being administered.

In a further implementation form of the third aspect, the monitoring, the creating, and the training are iteratively performed for the time interval during which the mechanical ventilator and/or the fluid balance of the patient are being adjusted.

According to a fourth aspect, a system for automated enteral feeding of a patient, comprises: at least one hardware processor executing a code for: computing a target nutritional goal to reach at an end of a time interval based on a basal metabolic rate of a patient obtained over a portion of the time interval, wherein the target nutritional goal comprises a volume to be delivered (VTBD) by the end of the time interval corresponding to a target amount of energy expenditure of the patient over the time interval computed according to the basal metabolic rate, computing a target feeding profile defining a target feeding rate for enteral feeding of the patient by an automated enteral feeding device for reaching the VTBD by the end of the time interval, continuously monitoring the real time energy expenditure of the patient over the time interval based on continuous measurements of the basal metabolic rate, dynamically adapting the target nutritional goal and corresponding VTBD to compute a maximum VTBD (max VTBD) to reach at the end of the time interval according to dynamic adaptations of the monitored real time energy expenditure of the patient, dynamically adapting the target feeding rate and the corresponding target feeding profile for a remaining portion of the time interval for reaching the dynamically adjusted max VTBD by the end of the time interval, wherein the target feeding profile tracks changes of the basal metabolic rate.

In a further implementation form of the fourth aspect, a feeding rate for reaching the maximal VTBD is computed as about 1.2*the feeding rate for reaching the VTBD.

According to a fifth aspect, a system for automated enteral feeding of a patient, comprises: at least one hardware processor executing a code for: computing a target feeding profile denoting a target enteral feeding of the patient by an automated enteral feeding device for reaching a target nutritional goal at an end of a time interval, defining a baseline feeding profile of a patient by matching to the target feeding profile, wherein the patient is automatically fed by the automated enteral feeding device according to the baseline feeding profile for reaching the target nutritional goal, pausing or slowing down the enteral feeding by the automated enteral feeding device for at least one pause time interval, wherein a feeding deficiency is formed between the target feeding profile and the baseline feeding profile during each pause time interval; and adjusting the baseline feeding profile is to a higher feeding rate that is higher than a feeding rate of the corresponding target feeding profile to compensate the feeding deficit for reaching the target nutritional goal at the end of the time interval.

In a further implementation form of the fifth aspect, the higher feeding rate is a defined maximal feeding rate.

In a further implementation form of the fifth aspect, the maximal feeding rate is selected according to likelihood of the patient refluxing the enteral feeding being below a threshold.

In a further implementation form of the fifth aspect, the maximal feeding rate is computed at about 1.75*a feeding rate defined by the target feeding profile.

In a further implementation form of the fifth aspect, further comprising a code for: detecting when the gap between the target feeding profile and the baseline feeding profile has closed, and reducing the baseline feeding profile to match the target feeding profile.

In a further implementation form of the fifth aspect, further comprising a code for: dynamically adjusting the target nutritional goal, dynamically adjusting the target feeding profile for reaching the dynamically adjusted target nutritional goal at the end of the time interval, and dynamically matching the baseline feeding profile to the adjusted target feeding profile for reaching the dynamically adjusted target nutritional goal.

In a further implementation form of the fifth aspect, the target nutritional goal is dynamically adjusted according to dynamic values of a computed resting energy expenditure (REE) of the patient, wherein the target nutritional goal is matched within a tolerance range to energy requirements of the patient determined according the REE.

In a further implementation form of the fifth aspect, the adjustment to the baseline feeding profile comprises an adjustment to the baseline feeding profile dynamically matched to the adjusted target feeding profile.

In a further implementation form of the fifth aspect, further comprising a code for: presenting within an interactive graphical user interface (GUI) on a display, a first curve denoting the target feeding profile, a second curve denoting the baseline feeding profile with dynamic adjustments, and marking a zone indicative of the gap of feeding deficiency formed between the target feeding profile and the baseline feeding profile.

In a further implementation form of the fifth aspect, further comprising a code for automatically detecting location of a feeding tube within a target feeding zone, and triggering the automatic enteral feeding by the automated enteral feeding device in response to the detected location of the feeding tube at the target feeding zone.

In a further implementation form of the fifth aspect, the target nutritional goal is computed match a resting energy expenditure (REE) of the patient within a tolerance range, the REE computed based on $CO_2$ production rate and/or $O_2$ consumption rate estimates of the patient made by measurements of at least one sensor.

In a further implementation form of the fifth aspect, the target nutritional goal excludes hidden calories in medications prescribed to the patient.

In a further implementation form of the fifth aspect, further comprising a code for presenting an interactive GUI for selection of at least one of a plurality of available feedings compositions currently in stock that most closely match the target nutritional goal.

In a further implementation form of the fifth aspect, the target feeding profile is computed per respective time interval of a plurality of time intervals as an increasing percentage of a maximal value of the target nutritional goal at the end of each respective time interval, wherein at each subsequent time interval the percentage is increased until the maximal value is met, wherein the target nutritional goal is set to the maximal value for additional subsequent time intervals.

In a further implementation form of the fifth aspect, further comprising a code for presenting within an interactive GUI, a dashboard presenting an indication of deviation from a target zone of a real time value of at least one of: urine output, metabolism, gastric reflux event, REE used to compute the target feeding profile, and gastro residual volume (GRV).

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3A is a graph depicting an example of adjusting a baseline feeding profile, in accordance with some embodiments of the present invention;

FIG. 3B is a depicting the process of adjusting the baseline feeding profile to reach a target nutritional goal, in accordance with some embodiments of the present invention;

FIG. 4 is equations for computing an estimation of an amount of enteral feeding lost due to reflux and/or a GRV procedure, for compensating by adjustment of the baseline feeding rate, in accordance with some embodiments of the present invention;

FIG. 15A-15B includes graphs depicting exemplary nutritional daily charts for a patient, summarizing exemplary important nutritional status of the patient, in accordance with some embodiments of the present invention;

Figure 1:
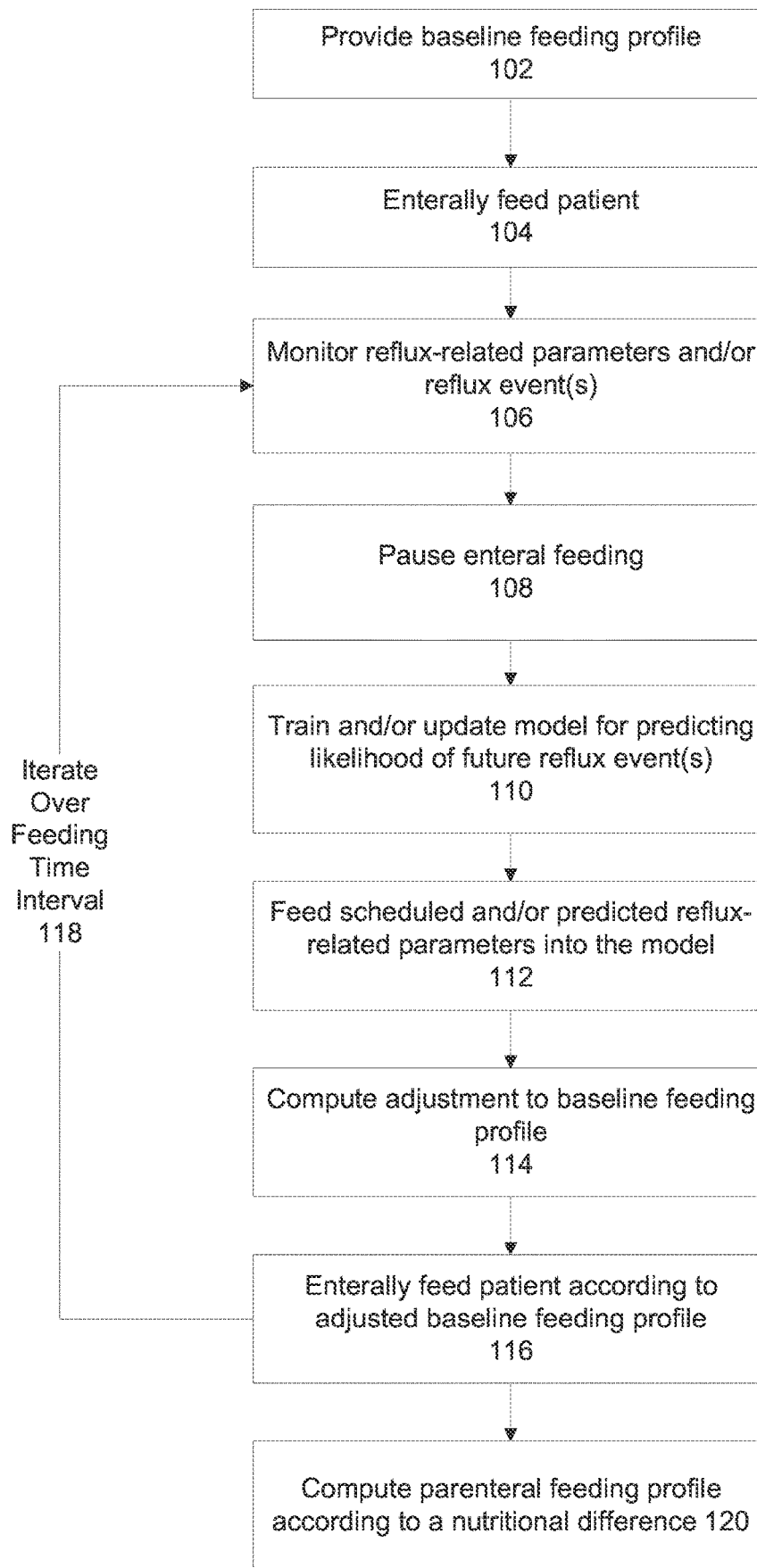
FIG. 1 is a flowchart of a method for treating a patient by automated adjustment of a baseline feeding rate for enteral feeding according to likelihood of future reflux event(s), in accordance with some embodiments of the present invention.

DESCRIPTION OF SPECIFIC EMBODIMENTS
OF THE INVENTION

The present invention, in some embodiments thereof, relates to treatment of a patient and, more specifically, but not exclusively, to systems and methods for treatment of a patient by automated patient care.

As used herein, the terms patient-related parameters and reflux-related parameters may sometimes be interchanged, for example, when clinical parameters measured for the patient are correlated with risk of reflux.

As used herein, the terms reflux-event parameters and at least one reflux event may sometimes be interchanged, for example, the reflux event may be defined according to one or more reflux-event parameters.

As used herein, the term reflux-related parameters refers to gastric reflux-related parameters, and/or the term reflux event refers to gastric reflux event.

An aspect of some embodiments of the present invention (sometimes referred to herein as artificial intelligence (AI), adaptive system, machine learning relating) to systems, methods, apparatus, and/or code instructions (i.e., stored in a memory and executable by one or more hardware processors) for personalized treating (and/or for generating instructions for treating) a patient by automated adjustment of an enteral feeding rate provided by an enteral feeding controller and/or ventilation assistance such as controlled suction. The adjustment is personalized for the patient, based on code of a model (e.g., machine learning code, for example, a classifier component) that learns the most optimal way to enteral feed the patient (e.g., to reach a target nutritional goal) while reducing risk of reflux events. The adjustment in rate is performed automatically by the model that learns correlations between reflux-related parameters and risk of reflux event (see FIG. 2B), and adjusts the feeding rate to reduce risk of reflux event. The model (e.g., statistical classifier component of the model) is trained for the current patient, i.e., trained differently for each patient according to data collected for the respective patient.

An aspect of some embodiments of the present invention relate to systems, methods, apparatus, and/or code instructions for automated enteral feeding of a patient by an automated enteral feeding device. A target feeding profile denoting a target enteral feeding of the patient for reaching a target nutritional goal at an end of a time interval is computed, for example, based on real time basal metabolic rate (also referred to as basal rate). The basal metabolic rate indicates the real time energy expenditure of the patient (e.g., REE), which may be computed based on sensor measurements over a short time interval (e.g., 5-15 minutes, or other values) which is extrapolated to the end of the time interval (e.g., at the end of 6, 12, 24, hours, or other values). The target feeding rate is computed based on the 24 hour (used as a non limiting example) target, for example, a feeding plan for the next 24 hours. The predicted 24 hour energy expenditure target to reach corresponds to a volume of an enteral feeding formulation selected to enteral feed the patient. The target volume of the enteral feeding formulation to provide by the 24 hour time target may sometimes be referred to herein as volume to be delivered (VTBD). A baseline feeding profile of a patient is defined by matching to the target feeding profile. The baseline feeding profile may include a baseline feeding rate matched to the target feeding rate to reach VTBD by the end of the 24 hour time interval. The patient is automatically fed by the automated enteral feeding device according to the baseline feeding profile for reaching the target nutritional goal. The enteral feeding may be pausing or slowing down by the automated enteral feeding device for at least one pause time interval. A feeding deficiency is formed between the target feeding profile and the baseline feeding profile during each pause time interval. The baseline feeding profile is adjusted is to a higher feeding rate (optionally a maximal feeding rate) that is higher than a feeding rate of the corresponding target feeding profile to compensate for the feeding deficit for reaching the target nutritional goal at the end of the time interval. The maximal feeding rate compensates for the feeding volume that would otherwise have been provided to the patient if not for the pause (or reduced rate) in the feeding, by providing additional volumes of feeding formula during the remaining amount of time. The compensation is designed to result in the same VTBD at the end of 24 hours that would otherwise have been provided if not for the pause (or reduced rate) in feeding.

An aspect of some embodiments of the present invention relate to systems, methods, apparatus, and/or code instructions for automated enteral feeding of a patient by an automated enteral feeding device. A target nutritional goal to reach at an end of a time interval is computed, optionally based on a basal metabolic rate (indicative of real time energy expenditure) of the patient obtained over a short portion of the time interval (e.g., 5-15 minutes, or other values), for example, 2000 Kcal in 24 hours based on about 20.8 Kcal basal metabolic rate and/or energy expenditure in 15 minutes. The target nutritional goal comprises a volume to be delivered (VTBD) of a selected feeding formulation by the end of the time interval corresponding to the energy requirement of the time interval, for example, for a formula where 1 milliliter (ml) provides 2 Kcal, VTBD is 2000 Kcal/2 ml per Kcal=1000 ml. The VTBD of the feeding formulation corresponds to a target amount of energy expenditure of the patient over the time interval computed according to the real time energy expenditure, by extrapolating from the short portion to the whole time interval. A target feeding profile defining a target feeding rate for enteral feeding of the patient by an automated enteral feeding device for reaching the VTBD by the end of the time interval is computed. For example, to reach 1000 ml by the end of 24 hours the feeding rate is about 1000/24=41.7 ml/hour. The real time energy expenditure of the patient is continuously monitored (or about continuously over short time intervals, for example, every second, minute, 5 minutes, or other values) over the time interval, optionally based on continuous measurements of the basal metabolic rate. The target nutritional goal and corresponding VTBD are dynamically adapted to compute a maximum VTBD (max VTBD) to reach at the end of the time interval according to dynamic adaptations of the monitored real time energy expenditure of the patient. For example, when the patient improves at hour 18 of the 24 hour time interval, and the new energy expenditure increases by 20%, a new target at the end of the time interval is computed to provide the patient with the extra 20% over the remaining portion of the time interval, i.e., for the remaining 6 hours. The max VTBD is computed, as initial VTBD and the additional volume over the previous VTBD to reach the new energy target. The target feeding rate and the corresponding target feeding profile are adapted for the remaining portion of the time interval for reaching the dynamically adjusted max VTBD by the end of the time interval. For example, for the remaining 6 hours, the feeding rate is increased to reach the new target of max VTBD. Effectively, the target feeding profile tracks changes of the basal metabolic rate.

The max VTBD may be defined by a user such as a physician in order to compensate losses.

The feeding rates described herein may be computed, for example, in terms of ml/hour, or ml/minute, or other time intervals.

The automated feeding may be paused, for example, due to a manual stop by a user, automatic stop by the device when reflux is detected, clogs in the gastric tube feeding outlet, and/or other reasons described herein.

It is noted that the volume digested by the patient may sometimes differ from the volume delivered to the patient. The systems, methods, apparatus, and/or code instructions described herein may refer to achieving digested volume for a patient by dynamically changing the delivered volume according the initial baseline, as described herein.

Optionally, a target feeding profile is set for reaching a target nutritional goal at an end of a time interval, for example, 24 hours. The baseline feeding profile, which indicates the actual feedings provided to the patient, is matched to the target feeding profile, which represent the desired feeding goal. A gap is formed between the target feeding profile and the baseline feeding profile during pauses of the enteral feeding. The gap indicates a difference between the total accumulated feedings actually administered to the patient, and the desired accumulated feedings. To close the gap, the feeding rate of the baseline feeding profile is increased. When the gap has closed, the feeding rate of the baseline feeding profile is reduced, to match the feeding rate of the target feeding profile. When the target nutritional goal is dynamically adjusted (e.g., increased), before the end of the time interval, the target feeding profile is adjusted (e.g., increased). The baseline feeding profile is adjusted (e.g., increased) to match the adjusted target feeding profile, in an attempt to reach the new target nutritional goal by the end of the time interval.

Optionally, for a patient (e.g., hospitalized, such as in the ICU), a large number of medical parameters are monitored (e.g., continuously such as by sensor, per event such as blood test results, regularly such as medical examination rounds by physicians and/or nurses) and may be stored in the electronic health record (EHR), for example, stored in an EHR server. The EHR accumulates past medical information and statistics of medical parameters (e.g., variables and/or signal) that potentially may affect the enteral feeding policy in form of food type and/or feeding rate. Alternatively or additionally, current medical status indicators for example oxygen saturation SPO2 heart data, ventilation data and patient motion (forced by care taker or spontaneous) may be recorded and stored in the EHR or other associated dataset.

The feeding rate may be increased when the risk of reflux is low, to compensate for reduced feeding during reduced feeding rates and/or pauses, for example, in the form of feeding stops (pause) which may be automatically triggered when reflux is detected and/or manually done by a user (e.g., care taker decision to pause the feeding for one or more reasons), to reach an optional target nutritional goal at the end of a feeding time interval. The correlations and adjustment of the feeding rate are iterated following the accumulated patient sensory data, which reduces overall risk of reflux events while providing enteral feeding for reaching as close as possible to the target nutritional goal. Optionally, when the patient has skin electrodes applied thereon, for example a lung water (i.e., edema), electrode and/or limbs electrodes, cross correlation may be computed to detect the cross effects between feeding parameters, water administration and/or medication administration and/or lung fluid.

Reflux-related parameters (e.g., time of reflux event, enteral feeding rate, patient orientation change (e.g., as detected by camera and/or inertial body strapped sensors), and administered medication) and reflux events are monitored while the patient is being automatically enteral fed by an enteral feeding controller. The patient is enteral fed according to a baseline feeding profile, which includes a target nutritional goal. The target nutritional goal is optionally defined for an end of a feeding time interval, computed as an aggregation over the feeding time interval, for total calories and/or total volume delivered over 24 hours. A model (e.g., classifier component) is trained for predicting likelihood of a future reflux event according to an input of a scheduled and/or predicted reflux-related parameter(s), for example, risk of reflux given a certain feeding rate and a scheduled patient orientation change event (e.g., due to a patient procedure), or risk of reflux associated with an administration of a certain medication. The model (e.g., classifier component) is trained according to computed correlations between the reflux-related parameters and the reflux event(s). Scheduled and/or predicted reflux-related events are fed into the model (e.g., classifier component) for outputting risk of likelihood of a future reflux event. The baseline feeding profile is adjusted for reducing likelihood of the future reflux event and for meeting the target nutritional goal. At least some implementations of the systems, methods, apparatus, and/or code instructions described herein include a learning and/or training model that automatically adjusts operating parameters to obtain a best fit for the specific patient. For example, when a certain medication has been previously associated with high risk of reflux, and the medication is scheduled to be administered again in the near future, the feeding rate may be reduced or even stopped in advance of the administration to prevent or further reduce risk of reflux. In another example, when a patient orientation change is scheduled (e.g., detected by an analysis of images of the patient captured by a camera, for example, daily changes of the patient's bedding), the feeding rate may be stopped during the orientation change (due to risk of reflux) and increased before and/or after the orientation change (when risk of reflux is low) for compensating for lack of feeding during the pause. In another example, the model (e.g., classifier component) learns risk of reflux during different times of the day (e.g., due to a physiological cycle of the patient) and adjusts the feeding rate accordingly to maximize feeding while reducing risk of reflux at different times of the day.

The feeding rate instructed by the enteral feeding controller (e.g. delivered by a pump) may be controlled, for example, by stroke frequency and/or by stroke amplitude and/or by combining frequency control with amplitude control.

The monitoring, training, and adjustment are iterated over the feeding time interval, for dynamically updating the correlations, dynamically computing risk of reflux for new scheduled reflux-related parameters and/or dynamically re-computing risk for known reflux-related parameters (using the updated correlation values), and dynamically adapting the feeding rate. The correlations values are updated for the respective patient based on the monitoring data, which increases accuracy of predicting risk of reflux-related parameters, and improves the ability to reach a tradeoff between a faster feeding rate (to reach the target nutritional goal) and reduction of risk of reflux events.

It is noted that the correlations may be between each reflux-related parameter and risk of reflux event, and/or between a combination of multiple reflux-related parameters and risk of reflux event. For example, certain individual reflux-related parameters may not be significantly correlated with a significant risk of reflux event, however a combination of multiple such reflux-related parameters may be significantly correlated with significant risk of reflux event.

Exemplary correlation of patient clinical parameters that are statistically significantly correlated to risk of reflux, discovered by Inventors during clinical studies using our implementations of a designed feeding tube, for example, as described in the applications incorporated by reference:

Reflux versus SPO2 (e.g., measured by a pulse oximeter).

Reflux versus Patient position and/or movement, optionally changes thereof (e.g., measured by camera and/or inertial sensors)

Reflux versus Bolus enteral administration (e.g., initiated by care taker decision)

Lungs water and/or edema versus Urine output (e.g., measured by skin and feeding tube electrodes)

Reflux versus lung fluid

Reflux versus urine output

Examples of systems and methods for sensing lung fluid and functionality are described with reference to International Patent Application No. IB2017/057702.

Examples of systems and methods for tracking spontaneous breathing in a mechanically ventilated patient are described with reference to application Ser. No. 16/000,922.

Examples of systems and methods for analyzing urine are described with reference to application Ser. No. 15/228,115.

Exemplary correlations computed herein (e.g., by the computing device) may be of the following form:

let $r_i$ be a reflux sequence of n elements let $m_{j,i}$ be the n measurements sequence of parameter j Then:

$$\rho^j = \frac{\sum_{i=1}^{i=n}(r_i - \overline{r}) \cdot (m_{J,i} - \overline{m_J})}{\sqrt{\sum_{i=1}^{i=n}(r_i - \overline{r})^2 \sum_{i=1}^{i=n}(m_{J,i} - \overline{m_J})^2}}$$

Then for example: if $p^j < 0.5$ weak correlation

If $p^j > 0.9$ strong correlation, halt feeding

The thresholds of 0.5 and 0.9 are exemplary. Other values for a threshold denoting weak and/or strong correlations may be used, for example, threshold for weak correlation may be 0.3, 0.4, 0.6, 0.7, or other smaller, larger, or intermediate values. Threshold for strong correlation may be, for example, 0.7, 0.8, 0.95, or other smaller, larger, or intermediate values. The threshold differentiating between weak and strong may be the same value, or different values. Parameters having strong correlations with reflux may be selected for adjustment of entral substance delivery (e.g., formula, water, medication) for reducing risk of reflux, as described herein. For example, when the computed correlation is above the strong correlation threshold, instructions for halting feeding may be generated. Parameters having weak correlations with reflux may be ignored for adjustment of entral substance delivery. For example, when the computed correlation is below the weak correlation threshold, feeding may continue. Parameters having correlations between weak and strong may be analyzed, for example, according to a set of rules, by the model, based on manual input, and/or other methods. For example, when the computed correlation is between the weak and strong threshold, instructions to adapt the feeding may be generated, for example, reduce the feeding rate without necessarily stopping feeding. The amount of reduction in rate may be proportion to the degree of correlation, for example, linearly, exponentially, non-linearly, and/or computed by the model.

Optionally, the adjustment to the baseline feeding profile includes an adjustment of water and/or medication for enteral delivery. For example, addition of extra water and/or administration of one or more medications. Optionally, the adjustment defines the time of day (e.g., range) when the water and/or medication is to be delivered.

Exemplary events that may trigger a feeding pause (i.e., stop, which may be temporary) include:
Administration of muscle relaxation medication (e.g., according to values stored in the EHR).
Patient movement (e.g., as indicated by an analysis of images captured by camera or inertial sensors).
Administration of a bolus (e.g., according to values stored in the EHR).

An aspect of some embodiments of the present invention relates to systems, methods, apparatus, and/or code instructions (i.e., stored in a memory and executable by one or more hardware processors) for treating (and/or for generating instructions for treating) a patient by automated enteral feeding. Data elements are obtained (i.e., monitored) over a monitoring interval. The obtained data elements include patient-related parameters, enteral delivered substances, and/or reflux-event parameters. The data elements are obtained while the patient is automatically enteral fed by an enteral feeding controller, optionally according to a baseline feeding profile including a target nutritional goal. A training dataset is created. The training dataset includes feature vectors each associated with an indication of time during the monitoring interval when the data elements were obtained. Each feature vector stores the patient-related parameters, the enteral delivered substances, and the reflux-event parameters, obtained during a time interval corresponding to the feature vector. A model is trained and/or generated based on the feature vectors of the training dataset. The model is adapted to receive current patient-related parameters and/or enteral delivered substances, and output instructions for adjustment of the enteral delivered substances. The adjustment may be for reducing likelihood of a future reflux event. The model may be trained according to computed correlations between patient-related parameters, enteral delivered substances, and/or reflux-event parameters. Current patient-related parameters are fed into the trained model for outputting instructions for adjustment of the enteral delivered substances (e.g., water, medication, enteral formula), optionally for reducing likelihood of a future reflux event. The enteral delivered substances are adjusted according to the instructions.

An aspect of some embodiments of the present invention relates to systems, methods, apparatus, and/or code instructions (i.e., stored in a memory and executable by one or more hardware processors) for treating (and/or for generating instructions for treating) a patient by adjustment of a mechanical ventilator and/or fluid balance. Data elements are obtained (i.e., monitored) over a monitoring interval. The obtained data elements include output of sensors located on a feeding tube positioned for enteral feeding of the patient (e.g., as described with reference to application Ser. No. 16/000,922, and/or IB2017/057702), ventilation-related parameters, and/or fluid-related parameters. The data elements are obtained while the patient is automatically enteral fed by an enteral feeding controller. A training dataset is created. The training dataset includes feature vectors each associated with an indication of time during the monitoring interval when the data elements were obtained. Each feature vector stores the output of the sensors located on the feeding tube, ventilation-related parameters, and/or fluid-related parameters, obtained during a time interval corresponding to the feature vector. A model is trained and/or generated based on the feature vectors of the training dataset. The model is adapted to receive current outputs of the sensors located on the feeding tube and output instructions for adjustment of the mechanical ventilator that automatically ventilates the patient and and/or the fluid balance of the patient. The adjustment may be for reaching a target patient-breathing parameter (e.g., SpO2, output of impedance sensors) and/or target patient-fluid parameter (e.g., urine output over a time interval). The model may be trained according to computed correlations between the output of the sensors located on the feeding tube, and/or the ventilation-related parameters, and/or the fluid-related parameters. Current outputs of the sensors located on the feeding tube are fed into the trained model for outputting instructions for adjustment of mechanical ventilator and/or fluid balance of the patient (e.g., give diuretic medication, give antidiuretic medication, give IV saline, give extra water with enteral feeding), optionally for obtaining the target patient-breathing parameter (e.g., target SpO2 value, target value of output of impedance sensor(s)) and/or target patient-fluid parameter (e.g. target urine output over 24 hours). The mechanical ventilator and/or the fluid balance are adjusted according to the instructions.

Optionally, the feature of obtaining the data items, the creation of the feature vector, and the training of the model are iterated over time to update the model based on outcomes of the adjustment. The model is fed new values and computes new adjustments based on the updated model. In this manner, the model iteratively learns results of its adjustment outputs, for improving the adjustment, optionally for further reducing risk of reflux.

At least some of the systems, methods, apparatus, and/or code instructions (i.e., stored in a memory and executable by one or more hardware processors) described herein relate to the problem of treatment of a patient by automated patient care. Most of the ICUs (and/or other exemplary healthcare departments) are not equipped with computerized information systems allowing calculation of daily and cumulative energy balance. This value may be missed if not evaluated daily, and the importance of keeping tight calorie balance may be disregarded. The cumulative negative energy balance may reach −10,000 kcal, thereby increasing the risks of morbidity and mortality, for example, as described with reference to Dvir D, Cohen J, Singer P (2005) *Computerized energy balance and complications in critically ill patients: an observational study. Clin Nutr* 25:37-44. Another substantial risk is the rehabilitation of a patient post-discharge that may be prolonged substantially, for example, as described with reference to Wischmeyer P E, San-Millan I (2015) *Winning the war against ICU-acquired weakness: new innovations in nutrition and exercise physiology. Crit Care* 19:s6. At least some of the systems, methods, apparatus, and/or code instructions described herein provide a next generation of feeding technology that explores the benefits of continuous energy expenditure and use AI and prediction algorithms to handle caloric and protein deficit. Communication between ICU and post-ICU discharge units to understand nutrition regime and predictive deficit, and an app to help the patient to recover after post-hospital discharge may be provided. Using the knowledge acquired in the analysis of hospital food left uneaten by patients to evaluate the energy, protein and vitamins deficits, at least some of the systems, methods, apparatus, and/or code instructions described herein may overcome the deficits in the post ICU period. When implemented in the critical stage, at least some of the systems, methods, apparatus, and/or code instructions described herein may help to ensure that a patient's nutritional plan and goals are constantly measured, monitored and achieved. Wearable data may be integrated with EHR data, including data from sensors continuously measuring physical activity and glucose level (missing reference).

At least some of the systems, methods, apparatus, and/or code instructions (i.e., stored in a memory and executable by one or more hardware processors) described herein improve patient safety, reduce mortality, and/or decrease complications and length of stay in the ICU.

At least some of the systems, methods, apparatus, and/or code instructions (i.e., stored in a memory and executable by one or more hardware processors) described herein may assist with one or more of the following: 1. Optimal patient feeding through a combination of real-time reflux detection and prevention. 2. Energy expenditure measurement and continuous personalized feeding formula selection. 3. Continuous monitoring of the enteral feeding delivery. 4. Calculations and continuous monitoring of supplement nutrition. 5. Automated information flow between units.

At least some of the systems, methods, apparatus, and/or code instructions (i.e., stored in a memory and executable by one or more hardware processors) described herein relate to the problem of treatment of a patient by enteral feeding, optionally including water and/or medication administration. Optionally, when special fluid administration associated with increased likelihood of reflux is used, for example medication administration, the pumping procedure may change to a "medication phase" for reducing likelihood of risk of reflux and/or reducing likelihood of risk of GRV. The Medication phase may be carried out, for example, by terminating the feeding for a period of time ahead of the medication phase and optionally reducing the delivering, for example, reducing the pumping rate for reducing the likelihood of reflux.

Design and/or selection of an appropriate enteral feeding regime, which includes the feeding rate (e.g., calories per unit of time) and/or composition of the enteral feeding (e.g., mix of carbohydrates, protein, fat and/or other nutrients) affects patient survival and recovery. There is a tendency to increase the feeding rate in order to provide the patient with sufficient amount of nutritional. However, on the other hand, a feeding rate that is too high results in reflux events. Reflux increase risk of complications for the intubated patient, for example, aspiration pneumonia resulting from reflux being aspirated into the lungs. Reducing the feeding rate to a low level may reduce risk of reflux, but may increase the risk of the patient not receiving sufficient nutrition which is associated with increased morbidity, mortality, and/or complications. Selection of an optimal feeding profile which on the one hand provides correct nutrition for the patient to improve treatment outcome, and on the other hand avoids or reduces risk of reflux is a challenging task at least due to the described tradeoffs.

Careful feeding control has been shown to be as a patient recuperation accelerator. For example, new intensive care unit (ICU) guidelines recommend to administer early enteral nutrition in critically ill adult patients when oral intake is not possible. Also, to avoid overfeeding, early full enteral nutrition shall not be used in critically ill patients but shall be prescribed within at least three days and more specifically in the first day 30% of the suggested nutrition, second day 50% third day 70% and from the fourth day on, until the full suggested amount is reached. The suggested amount may be determined by standard practice methods.

When following the guidelines for feeding, a preset feeding profile is determined and administered, where the same amount is provided all hours, every hour. The feeding rate is not adapted according to the ever-changing condition of the patient. As a result, the feeding procedure is not capable of compensating for food losses and is not capable of minimizing adverse events, for example, feeding halt due to reflux, gastric residual volume aspiration (GRV) and/or feeding halt for patient treatment. Standard feeding devices are no designed to reduce risk of such adverse events. Effectively, the delivered nutrition does not equal the digested nutrition that the patient actually absorbs, at least due to reflux where at least some of the enteral delivered food leaves the body of the patient (e.g., GRV).

In addition, the food consumption varies during the day due to patient's changing condition so if the daily routine stays and the feeding profile stays the same, some parts of the day will have reflux events and possibly massive reflux that will cause aspiration and aspiration pneumonia, because of low gastric emptying activity, and some parts of the day that potentially enable the caregiver to feed more will stay the same. Standard feeding methods are do not adopting a temporal feeding profile to better fit the patient's need when fast recuperation is the natural goal.

At least some of the systems, methods, apparatus, and/or code instructions (i.e., stored in a memory and executable by one or more hardware processors) described herein improve the technical field of automated enteral feeding of a patient for treatment thereof. The improvement is based on generating instructions for automated control of the enteral feeding by a feeding controller, which achieves an optimal trade-off between reaching as close as possible (and/or meeting) a target nutritional goal for increasing medical outcomes, and reducing or preventing risk of reflux which is linked to complications such as aspiration pneumonia.

The gastric administration of enteral feeding is associated with more vomiting and reflux than parenteral nutrition, for example, as described with reference to Reignier J, Boisrame-Helms J, Brisard L, Lascarrou J B, Ait Hussain A, Anguel N et al. (2018) *NUTRIREA-2 Trial Investigators; Clinical Research in Intensive Care and Sepsis (CRICS) group: Enteral versus parenteral early nutrition in ventilated adults with shock: a randomised, controlled, multicentre, open-label, parallel group study (NUTRIREA-2). Lancet* 391:133-143. The reflux and regurgitation are a factor for increasing the risks of ventilator-associated pneumonia (VAP), and there is a constant conflict between increasing feeding rate for reaching the nutritional goal and reducing feeding rate for decreasing aspiration. Therefore, clinicians are cautious in the progression of the rate of administration of enteral feeding in order to decrease the risks of reflux and vomiting and not increase the risks of VAP. Elevating the head of the bed to a half sitting position is the only demonstrated technique that reduces the incidence of VAP. The assessment of gastric function using gastric residual volume (GRV) test periodic aspiration is clinically used, but is not useful in monitoring enteral nutrition administration, for example, as described with reference to Reignier J, Mercier E, Le Gouge A, Boulain T, Desachy A, Bellec E et al. (2013) *Effect of not monitoring residual gastric volume on risk of ventilator-associated pneumonia in adults receiving mechanical ventilation and early enteral feeding: a controlled randomized trial. JAMA* 209:249-256. For an effective result of gastric evacuation, gastric residues should be released when reflux occurs, and not in an arbitrary and pre-determined (once every 4 hours) timeframe.

Known methods include, for example, predictive equations (e.g. Harris-Benedict) to determine nutritional requirements, and manually measuring gastric residual volumes (GRV) to determine safe enteral feeding rates. However, such known methods are not patient specific, and are based on a general approach based on studies performed for a wide ranging patient population. Moreover, such methods due not provide a dynamic tradeoff that balances reduction in risk of reflux with the goal of providing the patient with enterally delivered nutrition to reach a target nutritional goal. The described approach does not adapt to the specific patient needs, i.e., the approach at least has no learning capability, in contrast to at least some implementations of the systems, apparatus, methods, and/or code instructions described herein that have learning capability for adapting to needs of each specific patient.

Additional details of the technical problem related to reducing risk of reflux and/or aspiration pneumonia is described with reference to application Ser. No. 15/614,641. Additional details of the technical problem related to treatment of the patient by proper enteral feeding for increasing medical outcomes is described with reference to International Patent Application No. IL2017/051271.

As discussed herein, the compliance to guidelines as well as to prescription rarely achieves the nutritional goal. Numerous reasons may explain this poor adherence, but the need to give the prescribed dose of enteral feeding is not perceived as the need to administer an adequate and timely antibiotic prescription. An assessment of the patient's delivered feeding efficiency is automatically performed by at least some implementations of the systems, methods, apparatus, and/or code instructions described herein, not manually by the nurse. Exemplary elements that may be continuously calculated are: 1. Time lost by stopping feeding, for example, related to surgical procedure, CT or MRI tests. 2. Calculating and continuously compensating for all nutritional losses. Both compensation elements are automatically managed by at least some of the systems, methods, apparatus, and/or code instructions described herein. This would also free nurses' time.

At least some of the systems, methods, apparatus, and/or code instructions described herein address the technical problem by computing a risk of likelihood of a future reflux event by a model (e.g., classifier component of the model) that is dynamically updated by correlations computed for monitored reflux-related parameters and reflux events that occurred for the patient being enteral fed according to a baseline feeding profile. The risk of future reflux event is computed based on scheduled and/or predicted reflux-related parameters. The baseline feeding profile is dynamically adjusted based on the predicted likelihood of future reflux events, for reducing risk of the future reflux event. The model training and adjustment are iterated over time, for real time adaptation of the baseline feeding profile, which results in an optimal trade-off between reaching the target nutritional goal while reducing risk of reflux. Effectively, factors that cause the patient reflux are identified in advance and the feeding rate is adjusted appropriated to reduce risk of reflux. When no factors linked to reflux are identified in the near future, the feeding rate may be increased (e.g., up to a maximal defined rate). The adjustment is dynamically performed, while monitoring data is continuously gathered and analyzed to fine tune the baseline feeding profile. For example, a regularly scheduled patient sheet change is detected which is correlated with reflux. The rate is reduced in advance, but reflux still occurs. For the next sheet change, the rate is further reduced until no reflux occurs, or until a small amount of reflux below a threshold is obtained.

An example for adjustment of the feeding rate by the model is now described. The target enteral feeding rate is 60 [milliliter/hour (ml/hr)] and the pump stroke volume is 2.5 [ml] which leads to a stroke frequency corresponding to a stroke every 2.5 [minutes]. Now, when 4 strokes are lost or halted due to reflux or for other reason, the model generates instructions for compensating the loss by increasing after a while, the pumping rate to for example 1.5 strokes per minute for a period of time for making up of the loss. Note that a limit to the maximal rate is defined, for example, about 1 stroke per minute which correspond to about 150 [ml/hr] rate on continuous operation.

It is noted that the systems, methods, apparatus, and/or code instructions described herein do not simply perform automation of a manual procedure. First, no manual equivalent of the process described herein has been previously described. The process of manually determining the enteral feeding profile based on predictive equations and/or manually measuring GRV are different than the process described herein. Second, the process described herein includes automated features which cannot be performed manually by a human using pencil and/or paper. For example, computation of the correlations between reflux-related parameters and reflux events cannot be manually computed, a model cannot be manually trained, and a computation of risk of likelihood of future reflux events cannot be manually computed.

At least some of the systems, methods, apparatus, and/or code instructions (i.e., stored in a memory and executable by one or more hardware processors) described herein relate to the problem of selecting how and/or when to deliver water, and/or enteral formula and/or medications to an enteral fed patient for reducing risk of reflux. At least some of the systems, methods, apparatus, and/or code instructions (i.e., stored in a memory and executable by one or more hardware processors) described herein improve the medical field of treatment of a patient by improving delivery of water, and/or enteral formula and/or medications to an enteral fed patient for reducing risk of reflux. In some implementations, the technical solution to the problem and/or the improvement are obtained by the model that is trained on the feature vector of a large number of parameters. The model learns correlations of the parameters with reflux, and adjusts the enteral delivered substances according to an input of current value of the parameters, for reducing risk of reflux. The model is iteratively updated with values after the adjustment (which are indicative of results of the adjustment), and iteratively learns to further improve the adjustment to further reduce risk of reflux.

At least some of the systems, methods, apparatus, and/or code instructions (i.e., stored in a memory and executable by one or more hardware processors) described herein relate to the problem of treating a patient by parenteral nutritional. The standard of care suggests using enteral nutrition if gastric tolerance allows it. Some studies, for example, as described with reference to Casaer M P, Mesotten D, Hermans G, Wouters P J, Schetz M, Meyfroidt G et al. (2011) *Early versus late parenteral nutrition in critically ill adults. N Engl J Med* 365:506-17, have been understood in such a way that parenteral nutrition per se may be harmful and should not be prescribed in critically ill patients or only late in the clinical course. This is despite the fact that many recent papers, for example, as described with reference to Harvey S E, Parrott F, Harrison D A, Bear D E, Segaran E, Beale R, et al. (2014) *CALORIES Trial Investigators. Trial of the route of early nutritional support in critically ill adults. N Engl J Med* 371:1673-84, have shown the safety of parenteral nutrition. This reluctance to prescribe parenteral nutrition in cases of enteral nutrition failure is leading to negative caloric and nitrogen balance and may lead to impaired clinical outcomes, for example, as described with reference to Dvir D, Cohen J, Singer P (2005) *Computerized energy balance and complications in critically ill patients: an observational study. Clin Nutr* 25:37-44. Supplemental parenteral nutrition should be considered in any case of risk of undernutrition if enteral feeding does not reach the target after 3-7 days, for example, as described with reference to Singer P, Reintam Blaser A, M Berger M M, Alhazzani W, Calder P C, Casaer M (2018) *ESPEN guideline on clinical nutrition in the intensive care unit. Clin Nutr Epub ahead of publication*. At least some implementations of the systems, methods, apparatus, and/or code instructions described herein compute a personalized optimal combination of enteral and parenteral nutrition for each patient.

At least some of the systems, methods, apparatus, and/or code instructions (i.e., stored in a memory and executable by one or more hardware processors) described herein relate to the medical problem of improving breathing of a patient by control of mechanical ventilation and/or fluid balance, and/or improving urination of the patient by controlling water (e.g. IV, enteral routes, saline, or other fluids) and/or medications (e.g., diuretic, antidiuretic). Proper breathing and fluid balance are interlinked in compromised patients. Providing too much fluid to the patient (e.g. IV, enteral route, and/or using antidiuretic medications) may properly hydrate the patient but comes at a risk of fluid entering the lungs, which reduces the ability of the patient to breathe properly even when being mechanically ventilated. The mechanical ventilator may be adjusted to help the patient breath, but too much ventilating may damage the lungs of the patient, while when ventilation is insufficient the patient does not get enough oxygen. Too little fluid provided to the patient (e.g., too little IV fluid, too little enteral fluid, excess use of antidiuretics) may reduce risk of fluid in the lungs, but comes at the cost of increased risk in reduced urine output, damage to kidneys, dehydration, and/or buildup of toxins in the body. Therefore, tradeoffs affecting ventilation and fluid balance are difficult to manage, especially when performed manually as in common clinical practice. At least some of the systems, methods, apparatus, and/or code instructions (i.e., stored in a memory and executable by one or more hardware processors) described herein provide a solution to the medical problem by the trained model that monitors data elements for adjusting the mechanical ventilator and/or fluid balance to obtain the target patient-breathing parameter (e.g., SpO2 value, value of output of impedance sensor(s)) and/or target patient-fluid parameter (e.g., urine output over a time interval).

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term model may refer to one or multiple models, for example, artificial intelligence code and/or machine learning code and/or adaptive system and/or statistical classifiers. The model may include multiple components, for example, a statistical classifier and/or other code. For example, multiple components may be trained, which may process data in parallel and/or as a pipeline. For example, output of one type of model (e.g., from intermediate layers of a neural network) is fed as input into another type of model. For example, in an exemplary implementation a classifier component of the model is trained for predicting likelihood of a future reflux event according to defined inputs. An adjustment to the baseline feeding profile is computed by another component of the model, for example, for reducing likelihood of the future reflux event outputted by the classifier component. Exemplary models may include one or more statistical classifiers, which may be implemented as, for example: one or more neural networks of various architectures (e.g., artificial, deep, convolutional, fully connected), support vector machine (SVM), logistic regression, k-nearest neighbor, decision trees, and combinations of the aforementioned.

Figure 2:
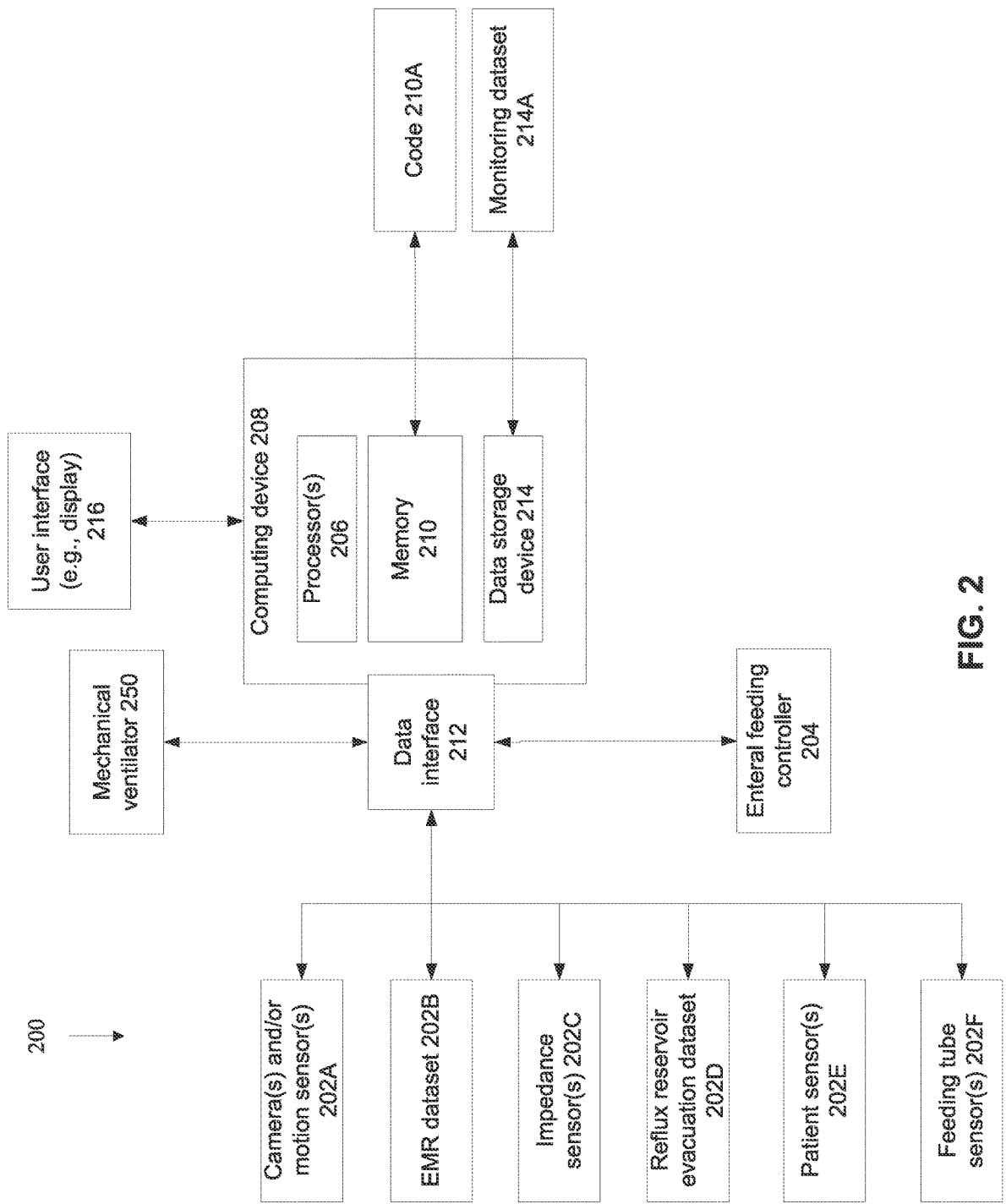
FIG. 2 is a block diagram of components of a system for treating a patient by automated adjustment of a baseline feeding rate for enteral feeding according to likelihood of future reflux event(s), in accordance with some embodiments of the present invention.

Reference is now made to FIG. 1, which is a flowchart of a method for treating a patient by automated adjustment of a baseline feeding rate for enteral feeding according to likelihood of future reflux event(s), in accordance with some embodiments of the present invention. Reference is also made to FIG. 2, which is a block diagram of components of a system 200 for treating a patient by automated adjustment of a baseline feeding rate for enteral feeding according to likelihood of future reflux event(s), in accordance with some embodiments of the present invention. One or more acts of the method described with reference to FIG. 1 may be implemented by components of system 200, as described herein, for example, by a hardware processor(s) 206 of a computing device 208 executing code instructions stored in a memory (also referred to as a program store) 210.

Computing device 208 may receive data via one or more data interfaces 212. Data may include monitored reflux-related parameters, for example, from one or more of: a camera and/or motion sensors 202A that captures images of the patient (and/or by code that analyzes the images and/or code that analyzes output of the motion sensors to compute an indication of the reflux-related parameters), and an electronic health record (EHR) of the patient obtained from an EHR dataset 202B (e.g., stored on an EHR server). EHR dataset 202B may store data indicative of past and/or future scheduled administration of diuretics, antidiuretics, and/or fluid (e.g., IV saline). Data may include an indication of reflux event(s) and/or reflux-event parameters, for example, from one or more of, impedance sensors 202C (e.g., located on a tube positioned inside the esophagus of the patient), and reflux evacuation reservoir data 202D (e.g., computed by code that analyzes the amount of reflux evacuated into a reservoir). Data may include output by one or more other patient sensors 202E, for example, urinalysis device, pulse oximeter (e.g., for sensing SpO2), urine sensor (e.g., sensing amount of urine and/or concentration of urine), calorimetry sensor, blood test machine, lung function machine, vital sign measurement devices (e.g., blood pressure sensor, heart rate sensor, breathing rate sensor, temperature sensor). Other sensors 202E may be described in the applications incorporated by reference listed herein. Feeding tube sensor(s) 202F which are located on the distal end portion of the feeding tube used to deliver the enteral feeding, for example, impedance sensors. Exemplary sensors(s) located on feeding tube 202F are described, for example, with reference to U.S. patent application Ser. No. 16/000,922, and International Patent Application No. IB2017/057702 (published as WO2018/104888).

It is noted that motion sensors 202A may be referred to herein using other implementations, for example, inertial sensors, 6 degree of freedom sensors, gyro sensors, and/or accelerometers.

Additional details of impedance sensors 202C and/or reflux evacuation reservoir data 202D are described, for example, with reference to application Ser. No. 15/614,641.

Data interface(s) 212 may be implemented, for example one or more of: a network interface, a port, a direct link, a wire connection, a wireless connection, a local bus, other physical interface implementations, and/or virtual interfaces (e.g., software interface, application programming interface (API), software development kit (SDK)).

Computing device 208 may be implemented as, for example, a standalone unit, a client terminal, a server, a computing cloud, a mobile device, a desktop computer, a thin client, a Smartphone, a Tablet computer, a laptop computer, a wearable computer, glasses computer, and a watch computer. Computing device 208 may be implemented as a customized unit that include locally stored software and/or hardware that perform one or more of the acts described with reference to FIG. 1. Alternatively, or additionally, computing device 208 may be implemented as code instructions loaded on an existing computing device. Alternatively, or additionally, computing device 208 may be implemented as hardware and/or code instructions (e.g., an accelerator card) installed and/or integrated within an existing computing device, for example, as a plug-in component.

Processor(s) 206 of computing device 208 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 206 may include one or more processors (homogenous or heterogeneous), which may be arranged for parallel processing, as clusters and/or as one or more multi core processing units.

Memory (also known herein as a data storage device) 210 stores code instructions executable by processor(s) 206, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 210 stores code instruction that implement one or more acts of the method described with reference to FIG. 1. Alternatively, or additionally, one or more acts of the method described with reference to FIG. 1 are implemented in hardware.

Computing device 208 may include a data storage device 214 for storing data, for example, monitoring database 214A that stores monitored data, for example indications of: reflux-related parameters, reflux-event parameters, and reflux events. Data storage device 214 may be implemented as, for example, a memory, a local hard-drive, a removable storage unit, an optical disk, a storage device, and/or as a remote server and/or computing cloud (e.g., accessed via a network connection).

Computing device 208 includes and/or is in communication with a user interface 216 that includes a mechanism for a user to enter data (e.g., patient information, baseline feeding profile) and/or view presented data (e.g., adaptations of the baseline feeding profile). Exemplary user interfaces 216 include, for example, one or more of, a touchscreen, a display, a keyboard, a mouse, and voice activated software using speakers and microphone. External devices communicating with computing device 208 may serve as user interfaces 216, for example, a smartphone running an application may establish communication (e.g., cellular, network, short range wireless) with computing device 208 using a communication interface (e.g., network interface, cellular interface, short range wireless network interface). The user may enter data and/or view data on the display of the smartphone, optionally via a graphical user interface (GUI) application.

Computing device 208 is in communication with an enteral feeding controller 204 that controls enteral feeding of the patient via an enteral feeding tube. Enteral feeding controller 204 controls and/or adjusts the rate of the enteral feeding according to instructions generated by computing device 208 based on the baseline feeding profile and adjustments thereof. Enteral feeding controller 204 (and/or another device) may adjust the composition of the enteral feeding according to instructions generated by computing device 208. Enteral feeding controller 204 may be implemented using a mechanical based mechanism, and/using computer components (e.g., processor(s), memory storing code instructions executable by the processor(s), and/or hardware components). Enteral feeding controller 204 may be implemented as a pump (e.g., positive displacement feed pump) that is controlled to deliver enteral feedings to the patient via the enteral feeding tube according to the rate defined by the instructions generated by computing device 208. Enteral feeding controller 204 may include a valve that selectively opens the lumen of the enteral feeding tube so that enteral feeding may be delivered to the patient at the defined rate.

As described herein, the term automated enteral feeding device may refer to one or more of: system 200 (and components thereof), computing device 208, enteral feeding controller 204, and/or other components of system 200, and/or combination thereof.

Computing device 208 is in communication with a mechanical ventilator 250 that automatically ventilates the patient. Current settings of mechanical ventilator 250 may be fed into the model, as described herein. Computing device 208 may output instructions for adjustment of mechanical ventilator 250, as described herein. Additional details of an exemplary mechanical ventilator are described, for example, with reference to U.S. patent application Ser. No. 16/000,922.

It is noted that alternatively to impedance sensor(s) 202C, other sensors for sensing reflux may be used (termed herein reflux sensors), and/or an indication of reflux computed by another computing device may be provided. Exemplary reflux sensor include one or more of: a pressure sensor that outputs electrical signals indicative of a sensed pressure within the stomach and/or esophagus, an impedance sensor that outputs electrical signals indicative of a sensed impedance within the stomach and/or esophagus, and a pH sensor that outputs electrical signals indicative of a sensed pH with the stomach and/or esophagus. Reflux event sensors may be located within the digestive system of the patient, for example, within the duodenum, the stomach, the esophagus, and/or other parts of the digestive system. Reflux event sensors may be located, for example, on and/or within an enteral feeding tube that is delivering enteral nutrition to the digestive system of the patient, located on and/or within an evacuation tube that removes refluxing gastric contents (as described herein), located on and/or within an optional gastric tube that delivers enteral feedings and removes refluxing gastric contents, and/or located on and/or within a separate probe.

A reflux evacuation reservoir may receive the reflux that left the body of the patient. Reflux evacuation reservoir may be implemented as, for example, a disposable bag, and/or a disposable container. Reflux evacuation reservoir may be connected to a vacuum source, or no vacuum source may be used (i.e., based on passive evacuation). The amount and/or volume of the digestive contents that exited the body of the patient may be computed and provided to the computing unit as reflux evacuation reservoir data 202D.

Additional optional components and/or additional optional features of components are provided, for example, with reference to application Ser. No. 15/614,641 and International Patent Application No. IL2017/051271.

Referring now back to FIG. 1, at 102, a baseline feeding profile is provided. The baseline feeding profile is defined over a feeding time interval, for example, over 4, 6, 8, 12, 24 hours, or other time frames. The baseline feeding profile may define a target nutritional goal to reach at the end of the feeding time interval. The target nutritional goal may denote an accumulation of multiple enteral feeding parameters to reach at the end of the feeding time interval, for example, total volume of the enteral feeding, total number of calories to provide to the patient, amount of protein to provide to the patient, and/or other nutrients to provide to the patient.

The nutritional goal may be changed during the feeding time interval (e.g., manually by a physician, automatically by code). The adjustment to the baseline feeding profile and/or the baseline feeding profile may be re-computed according to the adjusted nutritional goal. The nutritional goal may define a maximal limit for the feeding time interval, for example, maximum calories and/or maximum volume over 24 hours.

The baseline feeding profile may define a feeding rate, which may vary over the feeding time interval, for example, a temporal feeding profile. The baseline feeding profile may define a feeding formulation, which may be selected, for example, as described with reference to International Patent Application No. IL2017/051271).

The baseline feeding profile may be provided manually selected by a user and/or automatically computed by code. The baseline feeding profile may be computed, for example, based on a resting energy expenditure (REE) computed based on calorimetry sensors (e.g., as described with reference to International Patent Application No. IL2017/051271), based on predictive equations (e.g., Harris-Benedict), by a classifier that is fed parameters associated with the patient feeding and trained on a training dataset of baseline feeding profiles of feeding parameters sample patients.

The baseline feeding profile may include a maximal feeding rate. The maximal feeding rate denotes a maximum feeding rate which is not to be exceeded by the feeding controller. The maximal feeding rate is not to be exceeded when adjustments to feeding rate are made, as described herein. The maximal feeding rate may be computed according to a risk of likelihood of future reflux event below a requirement for no scheduled and/or predicted reflux-related parameters. The maximal feeding rate may be manually selected by a user (e.g., physician). The maximal feeding rate may be set according to a feeding rate tolerated by an enterally fed patient for which risk of reflux events are low (i.e., no expected upcoming change of patient position that increase risk of reflux event).

An exemplary process for setting the baseline feeding profile is now described. It is noted that other methods may be used, and/or the exemplary method may be adapted. The process may be executed by a GUI presented on a display associated with the computing device. An REE calculation is performed for determining the energy amount the patient is using, in order to determine the feeding plan for the baseline feeding profile. The REE measurement duration is defined. Once the duration is set (e.g., while patient is in resting) the measurement is launched. The measurement may be stopped if the patient is restless or for any other reason. After the duration has elapsed, the REE is calculated from the accumulated $VCO_2$ measurement (e.g., by a $CO_2$ sensor). The results may be accepted, or if they seem erroneous, they may be rejected. Once the REE measurement is accepted, the food calculator may be launched. If the operator selects to exit this panel it returns to the regular REE panel. The food calculator assists in selecting the optimal feeding material based on the REE calculation, hidden calories (optional to insert this information by the user), protein calculation and other optional filters (e.g., low fiber). Based on the food calculator's parameters and the selected nutrition, the volume to be delivered (VTBD) and nutrition basal rate are determined, and may be edited by the user. The user is asked by the GUI to set Max rate (per hour) and Max VTBD (per the duration of the feeding time interval, for example 24 hours), this will enable automatic adjustments in order to compensate for feeding stop time (e.g., because of reflux events or routine procedures by the caregivers like bedding, CT scans, surgeries, and the like) and for the residual loss in the GRV residual bag (which is weighted and/or flow is measured by a GRV flow sensor). The GRV mechanism is for decompressing the stomach in reflux event and/or changes in REE estimations that is within the determined range of the user. When $VCO_2$ exceeds the range set (e.g., threshold changed by +\−15%), an alert is generated. If Max VTBD is defined a new kCAL/day target is automatically computed and proposed, along with a newly derived VTBD and nutrition rate. Once accepted, a new baseline feeding plan is set. Additional exemplary details are described with reference to International Patent Application No. IL2017/051271.

Optionally, the baseline feeding profile is divided into portions with an expectation that there will be one or more pauses in feeding (e.g., due to reflux events, scheduled procedures and/or patient orientation events). For example, the baseline feeding profile to reach the target nutritional goal is computed for 18 hours rather than 24 hours, based on an expectation that there will be 6 hours of a pause in enteral feeding. In this manner, compensation for the 6 hours of no feeding is computed in advance. Alternatively, or additionally, the pauses in feeding are not initially considered, and the baseline feeding profile is computed for the full-time interval (e.g., 24 hours). Pauses and compensations are dynamically computed as described herein, for example, by limited time increase in the pumping rate.

Food type and/or additives may be selected a-priori by the physician and entered into the computing device based on the offering list presented to him/her according to the hospital available inventory. In another implementation, an updatable database of feeding materials is embedded in the computing device, or communicated to the computing device via the hospital system to create a personalized top list of the materials that fit the patient according to the baseline feeding profile.

At 104, the patient is automatically enterally fed by an enteral feeding controller (e.g., 204 described with reference to FIG. 2) according to the baseline feeding profile, which may include the target nutritional goal.

The patient is fed according to a baseline feeding rate defined by the baseline feeding profile.

At 106, multiple reflux-related parameters and/or an occurrence of reflux event(s) are monitored while the patient is automatically enterally fed.

Reflux-related parameters are collected in association with a detected reflux event. The reflux-related parameters may be collected for a time point and/or time interval prior to, and/or during the detected reflux event. The reflux-related parameters may be tagged with an indication of the detected reflux event for training the model (e.g., classifier component of the model) and/or computation of correlations by the model (e.g., classifier component of the model).

Optionally, reflux-related parameters are collected when no reflux event is detected. Such reflux-related parameters may be tagged with a category and/or label indicative of no reflux event when training the model (e.g., classifier component of the model) and/or computing correlations with reflux events by the model (e.g., classifier component of the model).

Reflux-related parameters and/or reflux events may be time stamped.

The reflux events may be monitored and/or detected for example, by sensing output of impedance sensor(s) 202C and/or output of reflux reservoir evacuation dataset 202D. Exemplary systems and methods for monitoring and/or detecting reflux events are described, for example, with reference to application Ser. No. 15/614,641).

The reflux-related parameters denote parameters which are statistically significantly correlated with increased and/or decreased risk of reflux events. The reflux-related parameters may be monitored by sensor(s) and/or code that monitors values (e.g., of fields) in a dataset.

The reflux-related parameters may be collected continuously, and/or during preset intervals (e.g., every 5 minutes, 10 minutes, or other time intervals), and/or triggered by events (e.g., during patient orientation change).

The reflux-related parameters may be collected when a reflux event is detected, and/or may be collected when no reflux event is detected. The gastric reflux event denotes digestive contents that have exited the stomach into the esophagus, for example, fluid, stomach acid, and administered enteral feeding. Gastric reflux events may be minor, in which stomach contents travel up the esophagus, but do not leave the body of the patient. Gastric reflux events may be severe, where stomach contents exist the body of the patient, for example, into a reservoir designed to collect refluxed stomach contents.

Exemplary reflux-related parameters and exemplary processes for monitoring thereof include:

Time of day. Time of day may be obtained, for example, from an internal clock, and/or querying a network clock. When a reflux event is detected, the time of day (e.g., range, start time, and/or end time) when the reflux event occurred is obtained.

Enteral feeding rate. The enteral feeding rate may be obtained, for example, from code that computed the current enteral feeding rate, from a field in memory that stores the current enteral feeding rate, and/or by querying the enteral feeding controller. When a reflux event is detected, the obtained enteral feeding rate may be for the feeding rate prior to the reflux event (e.g., immediately before), since the enteral feeding may be paused during the reflux event itself.

Patient location (also referred to as orientation and/or position), for example, lying down, rotated to left, rotated to right, reclining (e.g., angle of recline). Changes in patient location may be monitored, for example, a change in angle of recline, and/or a change from left rotation to right rotation. When a reflux event is detected, the patient location (and/or change thereof) may be for the patient location (and/or change thereof) prior to the reflux event (e.g., immediately before, a few seconds or minutes before, according to a threshold).

It is noted that other reflux-related parameters may be discovered and monitored. A combination of reflux-related parameters may be monitored. Such reflux-related parameters have a statistically significant correlation with risk of reflux even. Different patients may have different correlation values. Some reflux-related parameters may be statistically significant for some patients and not significant for other patients. For example, some patients may have a reflux event with a certain change in orientation while other patients do not suffer a reflux event for the same (or similar) change in orientation. Exemplary other reflux-related parameters include: one or more blood test values, one or more urinalysis test values, one or more lung function parameter values, and one or more values of vital signs.

Patient location changes may occur, for example, during changing of the patient's bedding (e.g., sheets, blankets, pillows, and/or coverings thereof).

Patient location changes may occur during patient procedures, for example, performing tracheal suction, and/or cleaning the patient (e.g., bathing the patient).

The patient location change may detect based on, for example, scheduled event requiring patient location change extracted from an electronic health record (EHR) of the patient, and/or an analysis of images captured by a camera monitoring the patient (e.g., a neural network that receives the images and outputs a classification category indicative of patient location).

6 degree of freedom (DF) inertial sensors output signals (e.g., acceleration and/or angular rate, for example, gyros) may be attached to the patient (e.g., body, clothing, straps, clips), which may provide an alternative and/or additional option for correlating patient motion with reflux occurrence.

Administered medication. When a reflux event is detected, the medications administered prior to the reflux event are obtained. The administered medications may be obtained, for example, from the EHR of the patient.

The reflux-related parameters may be stored in the monitoring dataset.

At 108, optionally, when a reflux event is detected by the monitoring process while the patient is being enterally fed, the enteral feeding may be paused by the enteral feeding controller. Alternatively, or additionally, the feeding may be automatically paused when a change in patient orientation is detected (e.g., when patient procedures are being performed) for example, detected by the analysis of images of the camera. Such change in orientation may occur spontaneously, not being scheduled in advance in the EHR and/or not following a routine (e.g., at the same time every day but not documented in the EHR).

A pause in enteral feeding may occur for other reasons, for example, a physician decision, due to a clog in the feeding tube, a diagnosis of gastroparesis (e.g., stored in the EHR), and/or a prokinetic medication (e.g., indicative of a problem in gastric intake). It is noted that in act 116, the adjustment to the baseline feeding profile automatically compensates for the pause in enteral feeding, by increasing the feeding rate when possible (e.g., risk of reflux is relatively low).

The pause may be for a pause time interval, which may be predefined and/or according to a detected end of the reflux event itself and/or according to the end of the patient orientation changes (e.g., end of patient procedure, end of change of patient bedding). Additional exemplary details of detecting a reflux event, pausing enteral feeding, evacuation of gastric contents during the reflux event (e.g., by establishment of a passive evacuation channel into a reservoir), detection of termination of the reflux event, and/or resumption of feeding are described, for example, in application Ser. No. 15/614,641. The patient change in orientation may be detected based on analysis of images of the patient captured by a camera, and/or based on a sensor monitor orientation of a patient that may be worn on the patient (e.g., accelerometer, compass, angle sensor).

Optionally, reflux-event parameter(s) are collected during the detected reflux event and/or the detected change in patient orientation event. Exemplary reflux-event parameter(s) include: reflux duration, and reflux amount. Reflux duration may be computed according to a start time when the reflux event was first detected (e.g., based on output of the impedance sensor(s)) and an end time when the reflux event is detected as having terminated (e.g., based on output of the impedance sensor(s)). Reflux amount may be computed according to the reflux reservoir evacuation dataset, for example, a sensor that monitors volume of reflux evacuated into a reservoir. It is noted that pausing feeding during the detected change in patient orientation may prevent or reduce reflux.

The reflux-event parameters may be stored in the monitoring dataset.

Optionally, when the reflux event is detected, an adjustment to the baseline feeding profile is computed by reducing the current feeding rate. The enteral feeding may be resumed after the pause time interval has elapsed, at the reduced feeding rate. Alternatively, when the patient orientation changes are detected, the adjustment to the baseline feeding profile may be to increase the baseline feeding rate to compensate for the loss of feeding occurring during the pause due to the patient orientation event. The increased in feeding rate may be bounded by the defined maximal feeding rate. The feeding rate may be increased, for example, when the computation of risk of reflux of a pause due to patient orientation change is low, even when the risk of reflux due to the patient orientation change is high. The patient orientation change may affect risk of reflux during the change itself, while risk of reflux before and/or after the change may be low. Therefore, since the pause due to patient orientation itself is not associated with risk of reflux, the feeding rate may be increased before and/or after the change when risk of reflux remains low. However, it is noted that during a next iteration, when the patient orientation change (which is associated with increased risk of reflux) is predicted (e.g., due to a regular recurring pattern, and/or detected from the EHR) the pause may be scheduled in advance, and the increased feeding rate may be computed in advance for compensating for lack of feeding during the pause. The compensation may occur before and/or after the planned pause.

It is noted that the resumption of feeding at the reduced feeding rate after the reflux event may be contrary to standard practice and/or intuition, where feeding rate is increased in order to compensate for losses of reflux. In contrast, as described herein, the feeding rate is gradually increased when risk of reflux is determined to be low, to prevent further reflux events. Compensation for the loss of feedings during reflux is performed when risk of reflux is computed to be low.

At 110, a model (e.g., classifier component of the model) is trained for predicting likelihood of a future reflux event according to an input of scheduled and/or predicted reflux-related parameters. It is noted that the model (e.g., classifier component of the model) is trained for each patient being enterally fed. The customized model (e.g., classifier component of the model) improves accuracy of computing an adjustment to the baseline feeding profile which is best for the current patient, for reaching the target nutritional goal while minimizing reflux events and/or severity of reflux events. Conceptually, the model (e.g., classifier component of the model) learns the feeding profile that is best tolerated by the current patient.

The outputted likelihood of future reflux event may be, for example, a binary value such as predicted reflux event, or no predicted reflux event. Alternatively, or additionally, the outputted likelihood of future reflux event is a category indicative of relative classes of risk, for example, high risk, medium risk, and low risk. Alternatively, or additionally, the outputted likelihood of future reflux event is a value, optionally a continuous value, indicative of probability of reflux event, for example, about 50%, or about 20%, or about 90%. The probability values may be thresholder to create the binary and/or category outputs.

The model (e.g., classifier component of the model) may be trained according to computed correlations between the reflux-related parameters and detected reflux event(s) and/or indications of no reflux event(s). The correlations may be a multi-dimensional space, where each reflux-related parameter denotes a respective dimension. Other implementations may be possible, for example, a neural network.

The model (e.g., classifier component of the model) is updated (e.g., continuously and/or at intervals and/or during defined events) with new monitored data and/or new detected reflux events and/or no detected reflux events. The model (e.g., classifier component of the model) may be updated according to correlations between the reflux-related parameters associated with the detected reflux event(s), and the detected reflux event itself.

The updating of the model (e.g., classifier component of the model) may update the computed correlations. Conceptually, the model (e.g., classifier component of the model) learns from its past mistakes by improving the correlations based on the new monitoring data, to provide more accurate predictions for the current patient. The updating may be iteratively performed, as described herein. The updating improves accuracy of the computed correlations for the current patient being enteral fed. The increased accuracy of the correlations enables fine tuning the baseline feeding profile according to the ability of the current patient to tolerate enteral feedings to reach the target nutritional goal, while reducing the reflux events and/or reducing severity of the reflux events.

Optionally, the reflux event(s) are associated with one or more reflux-event parameters, for example, reflux duration and/or reflux amount (e.g., volume). The model (e.g., classifier component of the model) may be trained for prediction of likelihood of the future reflux event based on computed correlations between the reflux-related parameters and the reflux-event parameters.

Optionally, the reflux event is defined as a requirement of the reflux-event parameters. The requirement enables defining what qualifies as a reflux event, such as severity of a reflux event of interest that should be avoided. For example, a minimal time that qualifies as a reflux event and/or minimal volume that qualifies as a reflux event. For example, short and/or small reflux events may be ignored, to focus on reducing risk of significant longer and/or larger reflux events. Alternatively, any time and/or any amount of reflux qualifies as reflux event, for example, to reduce risk of any reflux event of any severity.

Optionally, the correlations are computed between reflux-related parameters and reflux event(s) (and/or no reflux events) (which may be associated with an indication of time, for example, tags of time) falling within a common time window, for example about 5 minutes, or 10 minutes, or 15 minutes, or 20 minutes, or 30 minutes, or 45 minutes, or 60 minutes, other intervals. The common time window may enable determining cause and effect correlations, where a certain reflux-related parameter that occurred a certain amount of time before the reflux event is correlated with the reflux event. For example, administration of medication 10 minutes before the reflux event is correlated with risk of brining on the reflux event. Optionally, the common timing window is a sliding window that is slide over time stamped monitoring data. The correlations are iteratively computed according to the sliding window.

Optionally, the reflux-related parameters denote a time and/or location within a repeating physiological cycle. It is noted that the reflux-related parameter may be the actual time. The patient may experience a repeating physiological cycle, where for some parts of the cycle (e.g., day) the patient is able to tolerate faster feeding rates, and for other parts of the cycle (e.g., night) the patient may tolerate slower feeding rates. The correlation may be computed between reflux event(s) and/or no reflux event(s) and the time and/or location within the repeating physiological cycle. The risk of likelihood of future reflux event is based on a current time (i.e., fed into the trained model (e.g., classifier component of the model)) with respect to the repeating physiological cycle.

At 112, scheduled and/or predicted reflux-related parameters are fed into the trained model (e.g., classifier component of the model), for outputting risk of likelihood of a future reflux event.

The scheduled and/or predicted reflux-related parameters may be fed, for example, triggered in response to new detected data (e.g., new values appearing in the EHR of the patient), continuously, and/or at regularly scheduled time intervals.

The risk of likelihood of the future reflux event may be for a future time interval that includes the scheduled and/or predicted reflux-related parameters.

The scheduled and/or predicted reflux-related parameters may include, for example, one or more of:

A current time. For example, for predictions based on physiological cycles. It is noted that the current time for prediction based on the physiological cycle includes future times, where the future times do not necessarily need to be fed into the model (e.g., classifier component of the model). When the physiological cycle is associated with low risk of reflux by the model (e.g., classifier component of the model), the feeding rate may be increased. When the physiological cycle is associated with higher risk of reflux by the model (e.g., classifier component of the model), the feeding rate may be decreased.

Enteral feeding rate. For example, according to the feeding profile.

Patient orientation changes. Patient orientation changes may be scheduled, for example, appearing in the EHR of the patient, for example, a scheduled patient event where the patient requires change of location. The patient locations may be predicted based on a historical analysis of previous patient changes. For example, the images obtained from the camera capturing images of the patient indicate change of sheets once a day at approximately the same time every day and/or signal obtained, accumulated and analyzed by the patient body strapped inertial sensors. The future time for the change of sheets may be predicted.

Medication administration. Medications scheduled for administration to the patient may be obtained, from example, from the EHR of the patient.

At 114, an adjustment to the baseline feeding profile is computed for reducing likelihood of the future reflux event and for meeting the target nutritional goal. The adjustment to the baseline feeding profile may be computed by the model, for example, by another component of the model.

The adjustment to the baseline feeding profile may include an adjustment to a baseline feeding rate delivered by a pump. The stroke rate of the pump, and/or the stroke amplitude of the pump may be adjusted.

Optionally, when the risk of likelihood of the future reflux event denotes a likely occurrence of the future reflux event (e.g., according to a threshold, range, and/or other requirement), the adjustment is a reduction in feeding rate.

Alternatively, or additionally, when the risk of likelihood of the future reflux event denotes an unlikely occurrence of the future reflux event (e.g., according to a threshold, range, and/or other requirement), the adjustment is an increase in feeding rate.

Optionally, the adjustment is for compensating for reduced feedings provided to the patient during a predicted and/or scheduled pause in feeding due to change in patient orientation (e.g., scheduled procedure).

Alternatively, or additionally, the adjustment may be a pause in feeding for a computed time interval to reduce risk of reflux. For example, a reduction in feeding rate may refer to pausing the feeding (i.e., zero feeding rate) by an amount of time which is adjusted accordingly. Optionally, after the pause in feeding, the adjusted may be to increase or decreased the feeding rate in comparison to the feeding rate before the pause in feeding. For example, when the pause is due to a predicted and/or scheduled change in patient orientation (e.g., scheduled procedure), which is associated with relatively low risk of reflux, the feeding rate may be increased to compensate for the loss of feeding due to the pause. Alternatively, when the pause is due to a predicted and/or scheduled medication, which is associated with relatively higher risk of reflux, the feeding rate may be reduced to provide the patient with feeding while reducing risk of reflux due to the medication.

Optionally, the adjustment to the feeding rate is performed for reaching the target nutritional goal at the end of the feeding time interval. For example, for the computed risk of reflux, the feeding rate may be adjusted to 50 milliliters per hour (ml/hour). When 200 milliliters are required to reach the nutritional goal, and there are 5 hours left, the feeding rate may be set to 40 ml/hour rather than 50 ml/hour, since the 40 ml/hour is expected to provide the target nutritional goal with an even lower risk of reflux over the 50 ml/hour. As described herein, feeding rate may be controlled by stroke rate and/or by stroke amplitude.

Optionally, the adjustment to the feeding rate is performed for compensating for feeding losses occurring due to reflux and/or gastric residual volume (GRV) procedures and/or pauses in feeding due to other reasons (e.g., procedures performed on the patient). The compensation may be performed by increasing the feeding rate above the baseline feeding profile, below the optional maximal feeding rate, according to the tolerated risk of reflux event.

The reduction and/or increase in feeding rate may be performed using one or more processes:

Proportion according to the risk of likelihood of the future reflux event. The higher the predicted risk of reflux, the lower the rate. The lower the predicted risk of reflux, the higher the rate. The rate may be computed according to risk, for example, by an inverse function, by a linear correlation, by a logarithmic correlation, by an exponential correlation, by a function fitted to a set of points, and/or other methods.

By a constant predefined amount. The predefined amount may be the same or different for the increase and decrease in feeding rate. When risk is low, at each iteration, the feeding profile is increased by a defined amount (e.g., 1 cc/hour or other value). When risk is high, at each iteration, the feeding profile is reduced by the defied amount.

According to a set of rules based on the computed the risk of likelihood of the future reflux event. For example, when risk is high, lower the feeding rate drastically to a low level, maintain feeding rate at a low level for a time interval to make sure a low risk has been reached, then slowly titrate the feeding rate higher while risk remains low within an interval.

The increase in feeding rate may be limited by the maximal feeding rate. The maximal feeding rate may be computed according to a risk of likelihood of future reflux event below a requirement for no scheduled and/or predicted reflux-related parameters. The maximal feeding rate may denote the fastest feeding rate tolerated by the patient under best conditions, where risk of reflux is insignificant, low, and/or according to other thresholds.

The adjustment to the feeding profile may be computed based on an analysis of the amount of reflux that exited the body, for example, collected in the container, sensed by a sensor, and provided by the reflux reservoir evacuation dataset. The feeding profile may be adjusted to compensate for the amount of enteral feeding lost by the reflux event. Additional details are provided, for example, with reference to application Ser. No. 15/614,641.

The adjusted feeding profile may be presented on a display, for example, within a GUI, for example as described below with reference to FIGS. 3A-3B. The adjusted feeding profile may be further manually adjusted, for example, via the GUI.

At 116, the patient is treated by enteral feeding delivered by the enteral feeding controller according to the adjusted feeding profile. The feeding rate is according to the adjustment feeding rate.

Instructions for adjustment of the enteral feeding rate by the enteral feeding controller may be generated according to the computed adjustment feeding profile, for example, code, and/or a script, such as combined code, source code, human readable code in text format, and/or machine code. The enteral feeding controller implements the generated instructions for automated enteral feeding of the patient according to the adjusted enteral feeding rate and/or adjusted baseline feeding profile.

At 118, one or more features described with reference to acts 106-116 are iterated. The iterations dynamically update the correlations used by the model (e.g., classifier component of the model) to compute likelihood of reflux event, dynamically re-compute risk of reflux event based on new reflux-related parameters, and dynamically adjust the baseline feeding profile, optionally by dynamic adjustment of the enteral feeding rate. Effectively, the model (e.g., classifier component of the model) learns to more accurately predict risk of reflux events from the monitored data, and fine tunes the feeding rate to attempt to reach the target nutritional goal while reducing reflux events and/or severity thereof.

Iterations may be performed, for example, after each detected reflux event, after change in computed likelihood of reflux event, after new reflux-related parameters are obtained (e.g., from the EHR), and/or over the timer interval at predefined intervals (e.g., once an hour over the 24 hours' time interval).

Optionally, the monitoring is performed over a time interval for which a risk of likelihood of the future reflux event was previously predicted. The monitoring may be for data indicating reflux-related parameters and/or reflux events, which has accumulated from the later monitoring iteration. For example, a medication which was previously associated with triggering a reflux event is scheduled for administration in the future. The mediation is given once a day, and has been given for the past several day. A few days ago, the medication triggered a reflux event. The adjustment to the baseline feeding profile was previously computed, for example, in response to the previously detected administration of the medication and triggered reflux event, the feeding was paused yesterday for 10 minutes after the medication was administered. A reflux event still occurred, but was less in severity. The training is performed for the time interval and associated reflux event, for updating the trained model (e.g., classifier component of the model) based on the monitoring data accumulated since the previous training iteration. For example, the correlations are updated based on monitoring data collected during the pause and the triggered reflux event. The feeding into the model (e.g., classifier component of the model) is performed based on the updated trained model (e.g., classifier component of the model) for outputting a new and/or updated risk of likelihood of the future reflux event. The feeding into the model (e.g., classifier component of the model) may be iterated for previously processed and/or new scheduled and/or predicted reflux-related parameters. The feeding into the model (e.g., classifier component of the model), which is iteratively performed, may re-outputting updated risk of likelihood of the future reflux event.

The previously processed reflux-related parameters may be associated with updated risk of reflux event due to the updated correlations. For example, for the scenario that occurred yesterday of the administration of the medication and 10 minute pause post administration, likelihood of the smaller reflux event is computed. The adjustment is dynamically computed according to dynamically predicted likelihood of future reflux events. The adjustment may be re-computed according to changes in the likelihood of future reflux events arising from updated correlations and/or new reflux-related parameters. The feeding rate may be further reduced according to the re-outputted risk, for the same scenario for which the feeding rate was previously reduced but still resulted in reflux. The new feeding rate may be further reduced in an attempt to prevent reflux for the repeat scenario. The adjustment is performed to further increase the amount of time that the enteral feeding is paused to further reduce risk of reflux, for example, pause for 20 minutes. The 20 minute pause is implemented, which may result in preventing the reflux event. The model (e.g., classifier component of the model) is updated with the monitoring data that indicates that the 20 minute pause prevents reflux when the medication is administered.

At 120, optionally, instructions for parenteral feeding of the patient are generated (e.g., code, script, for manual setting of an automated machine). The parenteral feeding may be automatically performed by a parenteral feeding controller that implements the generated instructions.

The parenteral feeding may be computed at the end of the time interval, as a nutritional difference between the accumulation of enteral feeding parameters delivered according to the dynamically adjusted feeding profile, and the initially set target nutritional goal. The nutritional difference denotes the amount of missing nutrition which was unable to be enterally provided to the patient due to risk of reflux events. Since the missing nutrition cannot be made up enterally (i.e., will trigger reflux events), the missing nutrition may be provided parenteral.

Figure 2A:
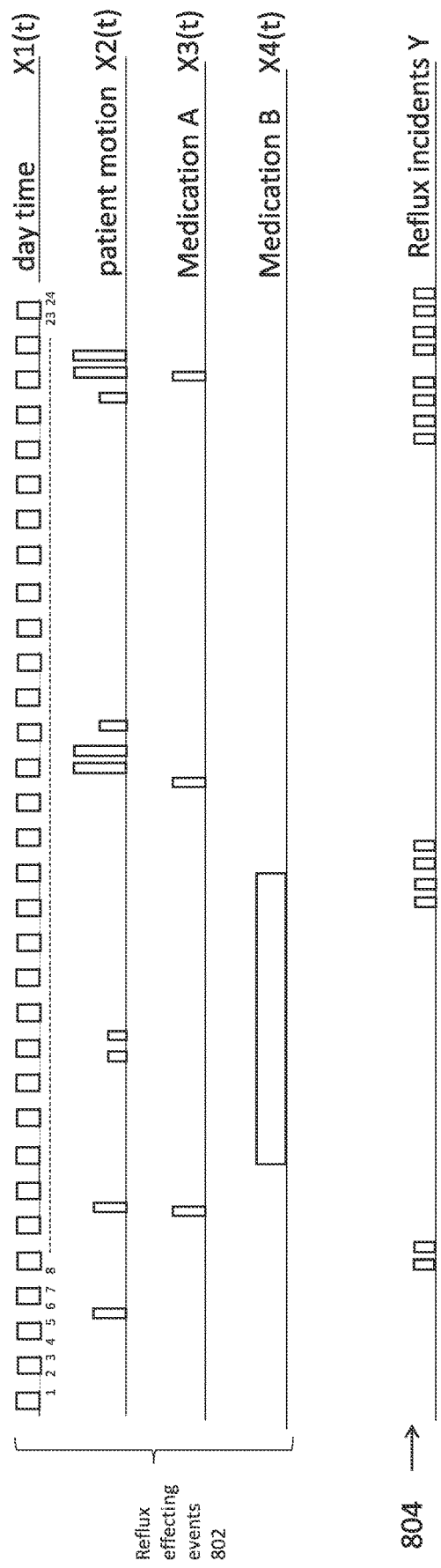
FIG. 2A is a graph depicting reflux-related parameters and reflux events occurring over a time interval for computing correlations thereof, in accordance with some embodiments of the present invention.

Reference is now made to FIG. 2A, which is a schematic depicting reflux-related parameters 802 and reflux events 804 occurring over a time interval, in accordance with some embodiments of the present invention. Correlations are computed between reflux-related parameters 802 and reflux events 804, as described herein. Reflux events 804 may be denoted by appearance of reflux, which may be in a pattern (e.g., intensity, volume, over a time interval) posing a significant risk for triggering inspiration pneumonia. For example, high correlation values between reflux-related parameter 802 and reflux events 804 over a threshold (e.g., about 0.7, or 0.8, or 0.9, or 0.95, or other intermediate, smaller, or larger values) may generate instructions for adaption of patient management, for example, pausing the enteral feeding or reducing the rate of enteral feeding.

Reflux-related parameters 802 may include: time of day (denoted $x1(t)$), patient motion (denoted $x2(t)$), one medication (denoted $x3(t)$), and another medication (denoted $x4(t)$), as described herein. Additional, fewer, and/or alternative reflux-related parameters 802 may be used. Reflux events are denoted y.

Correlations are computed between the reflux-related parameters 802 and reflux events 804, for example, reflux events (y) are correlated to daily events (x1, x2, x3, . . . ) such as patient motion, medication administration, and parts of the day (e.g., night, afternoon) which may be based on a physiological cycle of the patient. The correlations may be mathematically denoted as [y,x1], [y,x2], [y,x3], [y,x4], and additional correlations may be used for additional reflux-related parameters. The model learns the correlations, for reducing (or avoiding) likelihood of future reflux events, for example, by halting feeing before a predicted or scheduled reflux-related event.

Figure 2B:
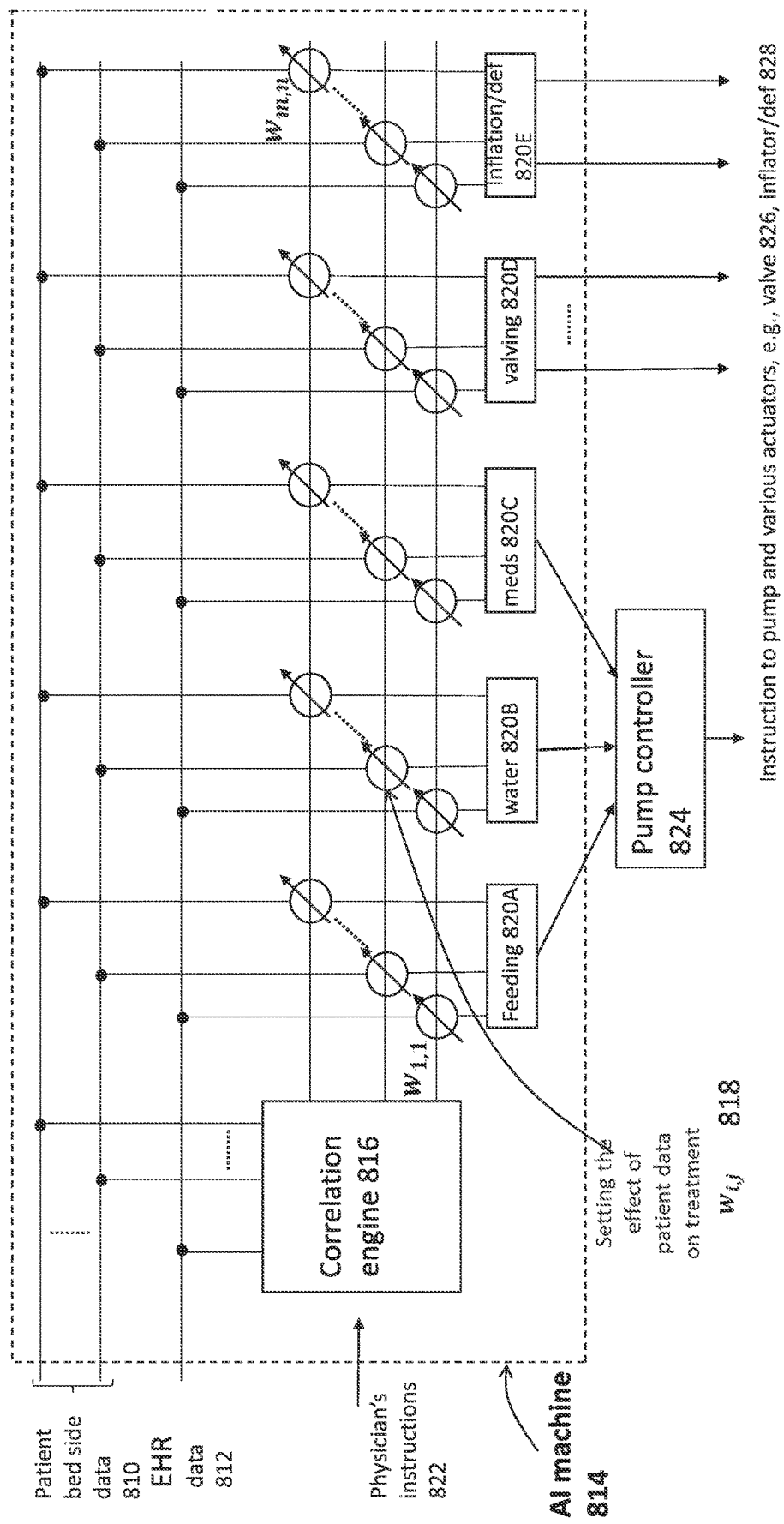
FIG. 2B is a schematic of exemplary dataflow for automated adjustment of enteral feeding and/or other parameters for patient management, in accordance with some embodiments of the present invention.

Reference is now made to FIG. 2B, which is a schematic depicting an exemplary dataflow of medical signals for automated adjustment of enteral feeding and/or other control parameters, in accordance with some embodiments of the present invention.

The dataflow of FIG. 2B may be implemented as, and/or integrated with, and/or replaced with, features and/or components described with reference to FIGS. 1-8. Data signals, including patient bed side data 810 and/or EHR data 812 (e.g., patient-related parameters, and/or reflux-event parameters and/or enteral delivered substances, for example, output of sensors and/or scheduled medication administration and/or scheduled events that indicate change in patient orientation) are fed into AI machine 814 (e.g., computing device executing at least code of the trained model described herein). The data signals are fed into a correlation engine 816, which computes multiple correlations, optionally values of weights denoted $W_{i,j}$ 818, as described herein. Correlations $W_{i,j}$ outputted by correlation engine 816, and the input data 810 812 are fed into one or more sub-component code 820A-E that compute instructions based on the correlations, for example, according to a set of rules, a sub-classifier component, and/or according to physician instructions 822. The instructions are provided for control of an enteral pump controller 824 and/or other actuators, for example, a valve 826 and/or inflator/deflator 828 of a balloon on the end portion of the feeding tube. Optionally, when risk of reflux is high, the balloon is inflated to prevent reflux from entering the esophagus, and optionally direct the reflux into an evacuation reservoir, for example, as described with reference to patent application Ser. No. 15/614,641. When risk of reflux is low, the balloon is deflated, for example, to prevent or reduce risk of damage to the inner lining of the esophagus from pressure.

Figure 2C:
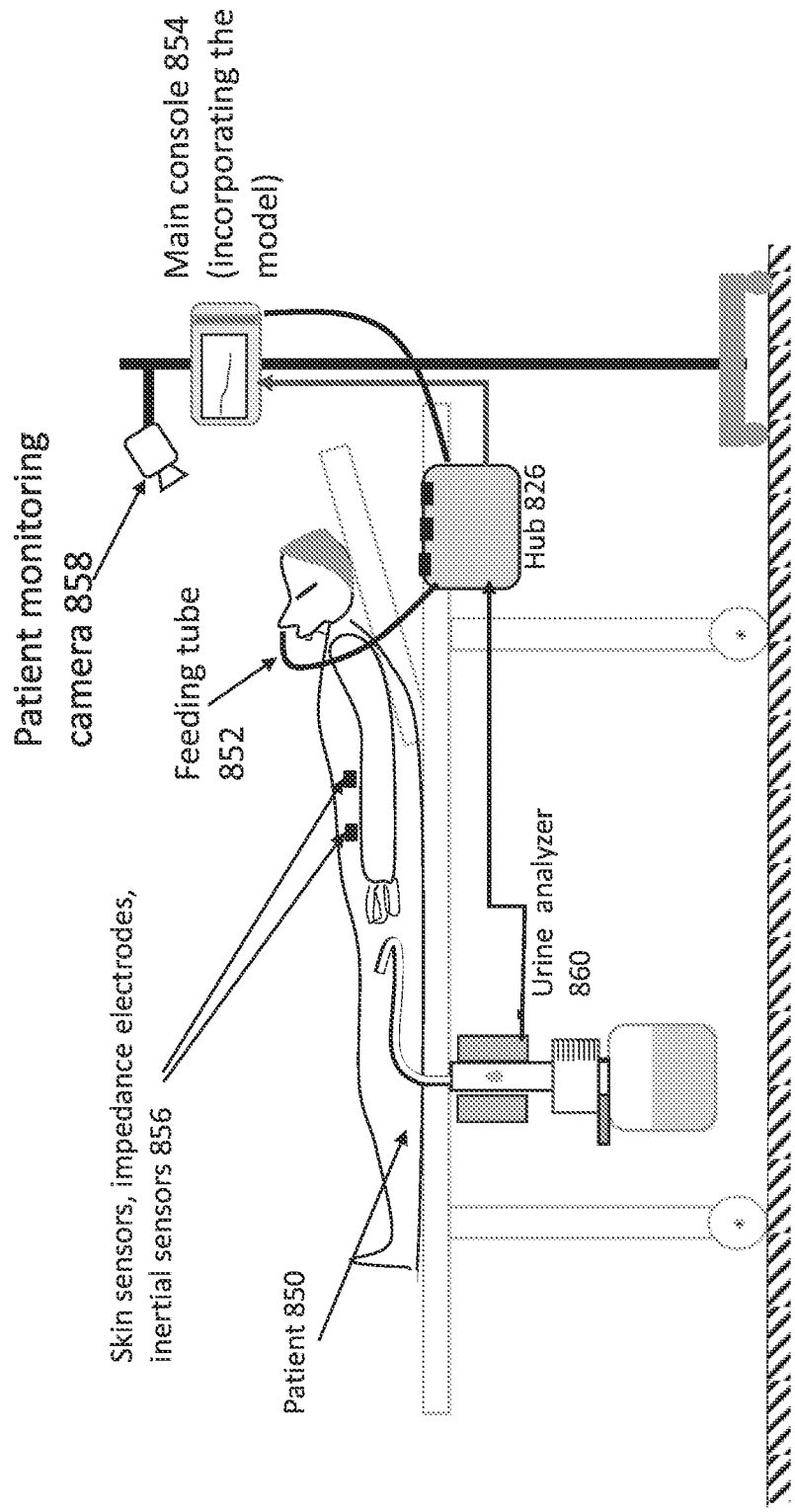
FIG. 2C is a schematic of an environmental perspective of a patient being fed by automatic adjustment of enteral feeding according to computed correlations for reduction of reflux, in accordance with some embodiments of the present invention.

Reference is now made to FIG. 2C which is a schematic of an environmental perspective of a patient 850 being fed via a feeding tube 852 by automatic adjustment of enteral feeding according to computed correlations for reduction of reflux computed by a main console 854 (e.g., including the computing device described herein that executes code of the model, e.g., AI machine), in accordance with some embodiments of the present invention. Patient-related parameters and/or reflux-related parameters of patient 850 are obtained from output of sensors 856 (e.g., skin sensors, impedance electrodes, inertial sensors, SpO2 sensor, cardiac sensor, vital sign sensors, skin electrodes, lung fluid measurement electrodes, limb electrodes, and others) and/or patient monitoring camera 858 and/or urine analyzer 860, as described herein. Data outputted from sensors may be fed into a hub 862, which communicates with main console 854 and/or may include an enteral feeding controller and/or pump. Hub 826 and/or main console 854 may communicate with the server storing the EHR of the patient. Console 854 receives the data, computes correlations (e.g., to detect cross effects between feeding parameters, water, and/or medication administration), and generates instructions for adjusting enteral substances fed into the patient (e.g. formula, water, medications), as described herein.

Reference is now made to FIG. 3A, which is a graph depicting an example of adjusting a baseline feeding profile 302, in accordance with some embodiments of the present invention. Baseline feeding profile 302 (depicted as dotted lines) is provided for 24 hours feeding time interval, as described herein. Baseline feeding profile 302 defines a feeding rate (e.g., in milliliters per hours (ml/hr), depicted on the y-axis as a function of time depicted on the x-axis. Baseline feeding profile 302 may define a maximal feeding rate 304 (e.g., 150 ml/hr), as described herein. At the start of the feeding session, the patient is fed according to the rate 306 defined by baseline feeding profile 302 (e.g., about 40-45 ml/hour). A first feeding pause A 308 occurs. Feeding pause 308 may occur, for example, due to a scheduled procedure on the patient that requires pausing feeding. When pause 308 ends, the feeding rate may be increased 310 to a rate above the initial baseline feeding profile 302, in order to compensate for the pause in feeding. The rate may be increased when the model (e.g., classifier component of the model) computes a relatively low risk of reflux events. At 312, a second feeding pause B occurs due to a detected reflux event. Feeding resumes 314 when the reflux event has ended, at a rate that is below the initial baseline feeding profile 302 and below the previous feeding rate 310, in order to reduce risk of another reflux event. Graph 316 depicts the accumulated amount of food provided to the patient during the feeding interval at time 10:00 AM (depicted by arrow 318 relative to the baseline feeding profile 302) relative to a target nutritional goal 320 (e.g., 1500 ml).

Reference is now made to FIG. 3B, which is a graph depicting the process of adjusting baseline feeding profile 302 to reach target nutritional goal 320, in accordance with some embodiments of the present invention. The graph of FIG. 3B includes graph FIG. 3A, which describes adjustment of baseline feeding profile 302 until 10:00 AM, and includes details of adjustment of baseline feeding profile 302 for the full 24 hours of the feeding time interval. Feeding continues until another scheduled feeding pause C 322 is reached. When pause 322 ends, the feeding rate may be increased 324 to a rate above the initial baseline feeding profile 302, in order to compensate for the pause in feeding. The rate may be increased when the model (e.g., classifier component of the model) computes a relatively low risk of reflux events. At 326, a gastro residual volume (GRV) event occurs, where a significant amount of digestive contents are evacuated from the digestive system (e.g., stomach) of the patient, as denoted by the negative feed rate values. The GRV event may occur, for example, due to reflux of the patient, and/or a scheduled GRV procedure. At 328, the feeding rate may be increased to a rate above the initial baseline feeding profile 302, in order to compensate for the GRV losses. The rate may be increased when the model (e.g., classifier component of the model) computes a relatively low risk of reflux events. It is noted that at all times the adjusted feeding rate is maintained below maximal feeding rate 304. At end of the 24 hours feeding interval, graph 316B indicates that the target nutritional goal 320 has been met.

Reference is now made to FIG. 4, which includes equations for computing an estimation of an amount of enteral feeding lost due to reflux and/or a GRV procedure, for compensating by adjustment of the baseline feeding rate, in accordance with some embodiments of the present invention. The amount of lost water can be calculated by subtracting the lost food volume $V_f$ from the total volume $V_t$.

An exemplary implementation of a model (e.g., classifier component of the model) based on the monitoring data is now described. The model (e.g., classifier component of the model) is based on the $\chi^2$ technique, curve fitting, and/or adaptive optimum processes.

Figure 5:
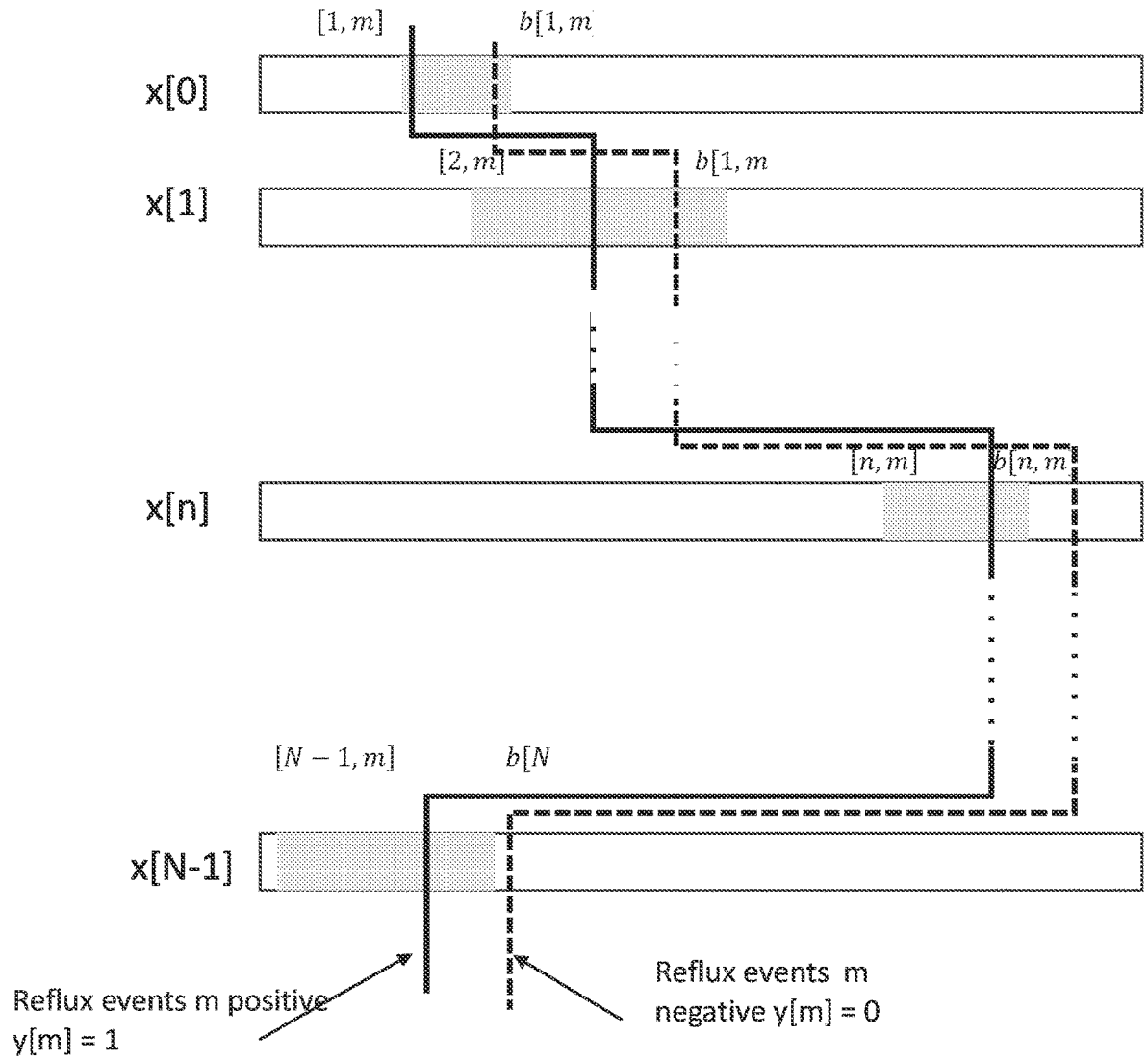
FIG. 5 is a graph that presents a reflux event denoted y[m] that is associated with reflux-related parameters denoted x[n] in a range denoted a[n,m] and b[n,m], where it is assumed that N reflux events are present and M possible reflux-related parameters are considered, in accordance with some embodiments of the present invention.

Reference is now made to FIG. 5, which is a graph that presents a reflux event denoted y[m] that is associated with reflux-related parameters denoted x[n] in a range denoted a[n,m] and b[n,m], where it is assumed that N reflux events are present and M possible reflux-related parameters are considered, in accordance with some embodiments of the present invention.

When patient reflux-related parameters denoted X are within the range denoted a[n,m] and b[n,m] it is concluded that the patient has experienced reflux event denoted y[m] or, logically stated:

$$\bigcap_{n=0}^{n=N-1}\{a[n,m]\leq X\leq b[n,m]=1\} \text{ then } Y=y[m]$$

Figure 6:
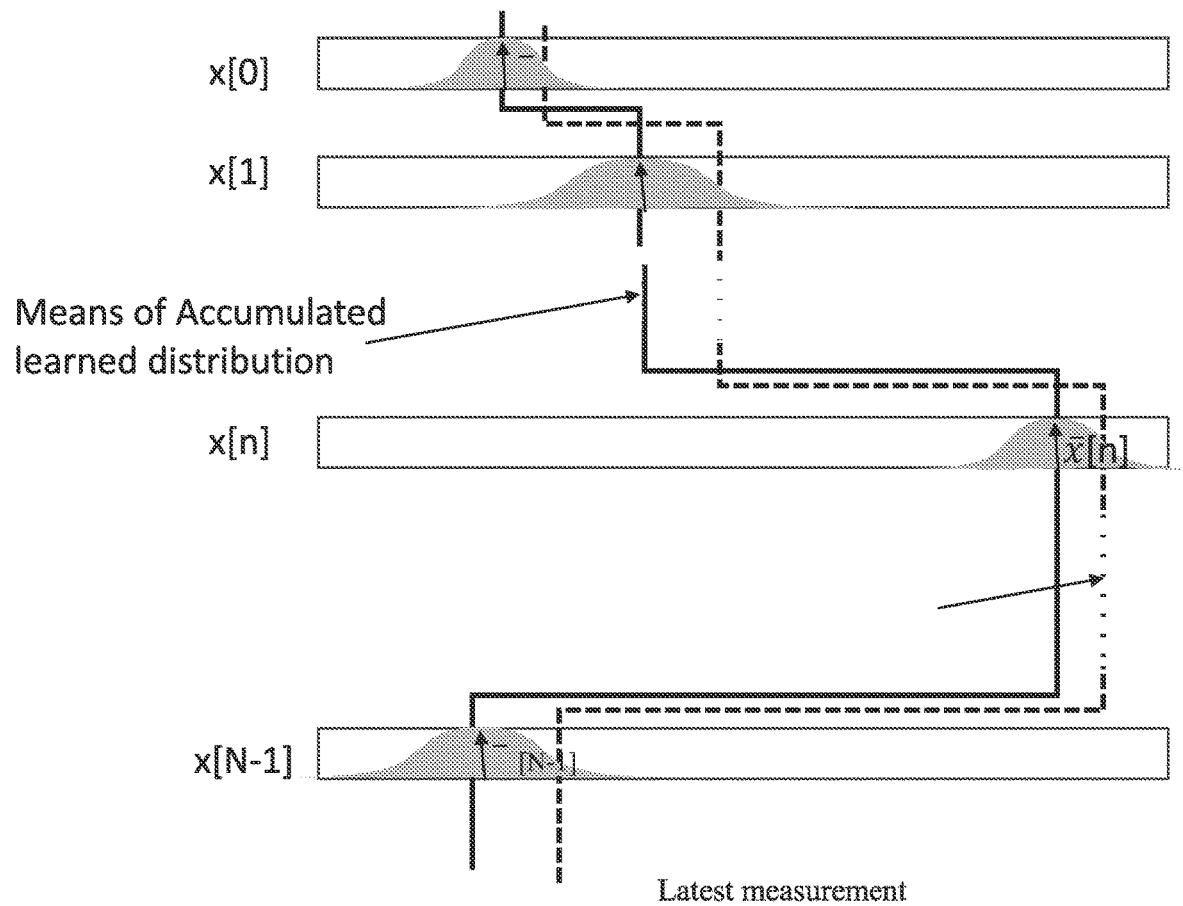
FIG. 6 is a normal distribution of the accumulated reflux-related parameters associated with reflux events, in accordance with some embodiments of the present invention.

Reference is now made to FIG. 6, which depicts a normal distribution of the accumulated reflux-related parameters associated with reflux events, in accordance with some embodiments of the present invention.

When data for a specific patient is analyzed the resulting measured parameters will be used to test for a series of null hypothesis each associated with one of the M potential reflux events:

$$H_0^m m(0 \ldots M-1)$$

The associated Chi square value associated with each of the M hypothesis (one of the M potential reflux events) will be given by:

$$\chi^2[m] = \sum_{n=0}^{n=N-1} \frac{[x[n]\text{measured} - \bar{x}[n]\text{accumulated}]^2}{\bar{x}[n]\text{accumulated}}$$

Figure 7:
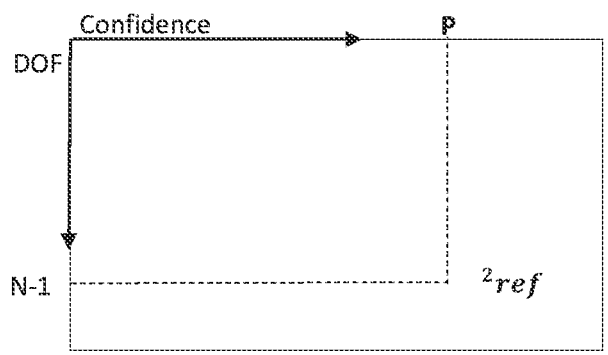
FIG. 7 is a depicting resulting value of each of the M calculated $\chi^2[m]$ compared with the ref value $\chi^2\text{ref}$ taken from a standard $\chi^2$ table under the desired confidence level P and the number of degrees of freedom N-1, in accordance with some embodiments of the present invention.

Reference is now made to FIG. 7, which is a graph depicting resulting value of each of the M calculated $\chi^2[m]$ compared with the ref value $\chi^2$ref taken from a standard $\chi^2$ table under the desired confidence level P and the number of degrees of freedom N-1, in accordance with some embodiments of the present invention.

The decision is taken to be reflux event m* of the M possible for which:

$\chi^2[m^*]$ is the smallest of all $\chi^2[m]$'s

And $\chi^2[m^*]<\chi^2$ref

If non-fits additional tests are indicated.

The a's and b's are obtained from the monitored dataset and as additional data is gathered, they are updated by:

$$a[n,m]=a[n,m]+\Delta a[n,m]$$

$$b[n,m]=b[n,m]+\Delta b[n,m]$$

The Δ's are corrections of the limits based on new accumulated data. For the case where, normal distribution is accumulated and used, the distribution will also be updated when additional statistics is accumulated.

Figure 8:
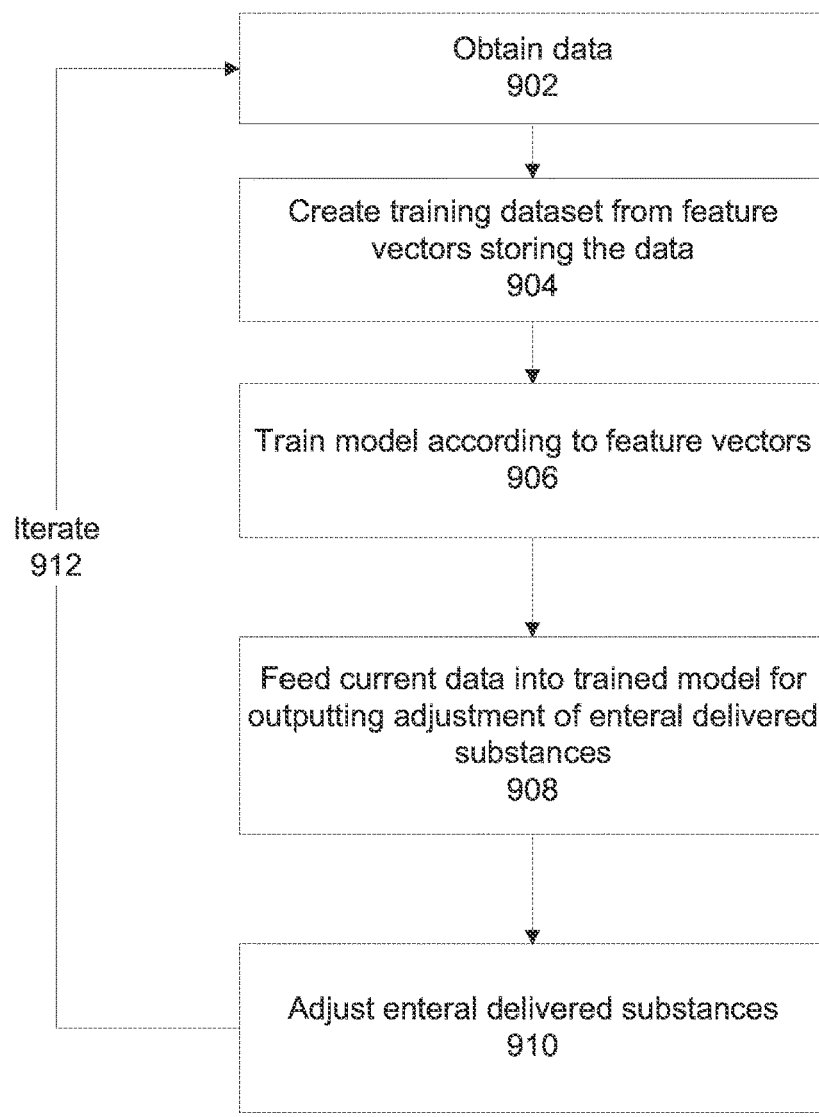
FIG. 8 is a flowchart of an exemplary method for generating instructions for treating a patient by automated enteral feeding controlled by a trained model, in accordance with some embodiments of the present invention.

Reference is now made to FIG. 8, which is a flowchart of an exemplary method for generating instructions for treating a patient by automated enteral feeding controlled by a trained model, in accordance with some embodiments of the present invention. The method described with reference to FIG. 8 may include, and/or substitute for, and/or be combined with, features and/or components described with reference to FIGS. 1-7.

It is noted that the model described herein may refer to the model of FIG. 1, and/or the model of FIG. 8, and/or combinations thereof. For example, data elements used to train the model of FIG. 8 may be used to train the model of FIG. 1.

At 902, data is obtained. The data may be obtained by a monitoring process over a monitoring interval. The data may be obtained while the patient is automatically enteral fed by an enteral feeding controller. The data may be obtained from one or more components 202A-E.

The patient may be enteral fed according to a baseline feeding profile, which may include a target nutritional goal, as described herein.

One or more of the following exemplary data may obtained:

Patient-related parameters. The patient-related parameters may include static and/or dynamic values associated with the patient.

Exemplary patient-related parameters include: patient demographics, patient age, patient gender, current patient medical diagnosis, past patient medical history, current patient signs and/or symptoms, patient vital signs, patient urine data, patient calorimetry data, enteral feeding rate, patient location changes, blood test values, urinalysis test values, lung function parameter values.

Enteral delivered substances. The enteral delivered substances include one or more substances that are enteral delivered to the patient. Exemplary enteral delivered substances include: enteral feeding (e.g., formula), water, and one or more medications.

The enteral delivered substances may be defined by the baseline feeding profile, and/or for reaching the target nutritional goal.

Reflux-event parameters. The reflux-event parameters define one or more aspects of the reflux event. Exemplary reflux-event parameters include: time of day of the reflux event, volume of reflux, intensity of reflux, duration of reflux, weight of reflux.

At 904, a training dataset is created by computing one or more feature vectors. Each feature vector stores (e.g., an indication of) the obtained data elements, including the patient-related parameters, and/or the enteral delivered substances, and/or the reflux-event parameters, for example, as a large vector where each value of each parameter is stored in an element of the feature vector.

Each feature vector may be associated with an indication of time during the monitoring interval indicating when the respective data element was obtained. Alternatively, or additionally, individual data elements are each associated with an indication of time when the respective data element was obtained. The time may be stored as an element of the feature vector.

Each feature vector may store data elements obtained during a common time interval, for example, within a 10 minute interval, or other values.

At 906, a model is trained and/or created based on the training dataset. The model is adapted to receive current patient-related parameters and output instructions for adjustment of the enteral delivered substances. The adjustment of the enteral delivered substances may be for reducing likelihood of a future reflux event.

The model may be trained according to computed correlations between the patient-related parameters, and/or the enteral delivered substances, and/or the reflux-event parameters. The correlations may be indicative of which patient-related parameters and/or enteral delivered substances, alone or in a combination, are associated with various risks of reflux events having varying values of reflux-event parameters.

At 908, current patient-related parameters and/or current enteral delivered substances are fed into the trained model. The model outputs instructions for adjustment of the enteral delivered substances. The adjustment may be selected for reducing likelihood of a future reflux event.

For example, the adjustment may be for entering a medication phase when administration of medication is indicated, by temporarily halting (i.e., pausing) feeding for a predefined time interval for reducing likelihood of reflux.

In another example, the adjustment defines how much water to enteral provide to the patient, and when in time to provide the water. The water providing may be selected to reduce likelihood of reflux.

In another example, the adjustment defines when in time to administer a scheduled medication to the patient. The medication administration may be selected to reduce likelihood of reflux.

At 910, the enteral delivered substances are adjusted according to the instructions.

At 912, one or more of features 902-910 are iterated over time. The receiving of data of 902, the creating the dataset of 904, and the training the model of 906 are iterated over time to update the model with responses to the adjustment of the enteral delivered substances. The model learns the effects of its adjustment decisions, and iteratively improves the decision making ability to reduce risk of reflux and/or improve delivery of enteral delivered substances. Features of 908-910 are iterated over time for new data values using the updated model.

Figure 9:
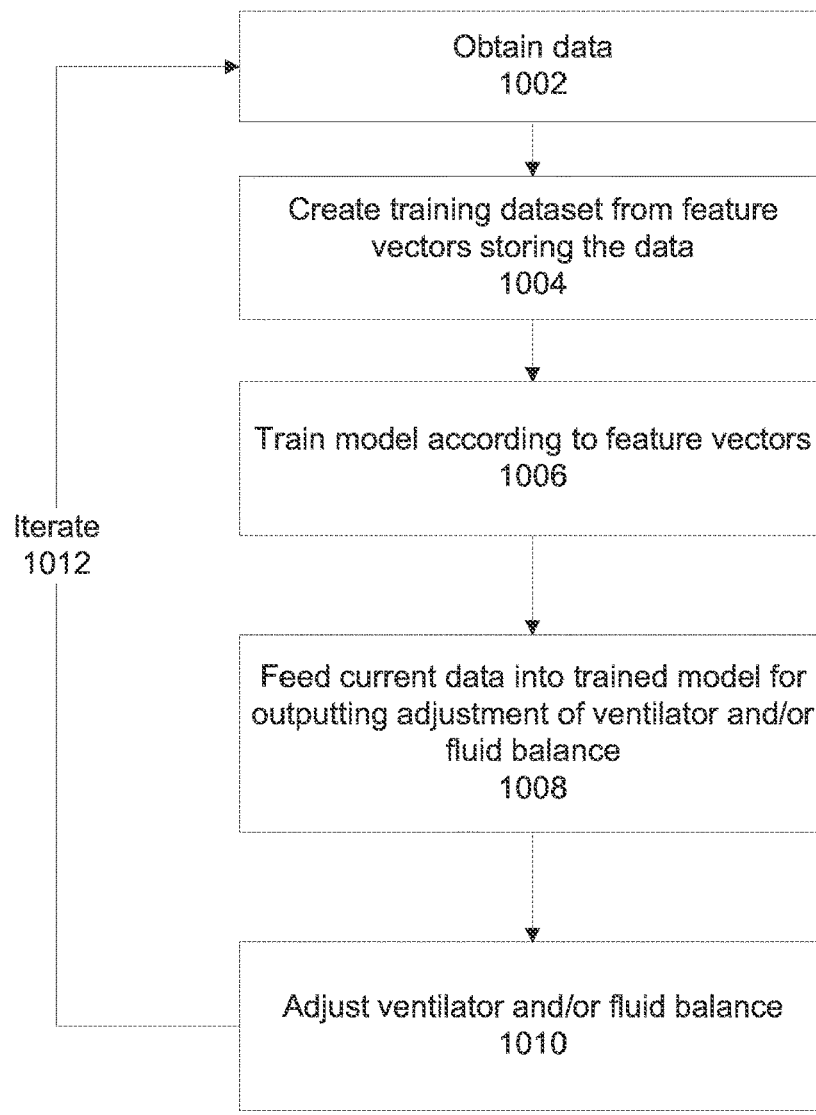
FIG. 9 is a flowchart of an exemplary method for generating instructions for treating a patient by adjustment of a ventilator and/or fluid balance of a patient according to instructions based on output of a trained model, in accordance with some embodiments of the present invention.

Reference is now made to FIG. 9, which is a flowchart of an exemplary method for generating instructions for treating a patient by adjustment of a ventilator and/or fluid balance of a patient according to instructions based on output of a trained model, in accordance with some embodiments of the present invention. The method described with reference to FIG. 9 may include, and/or substitute for, and/or be combined with, features and/or components described with reference to FIGS. 1-8.

It is noted that the model described herein may refer to the model of FIG. 1, and/or the model of FIG. 9 and/or other implementations of the models described herein, and/or combinations thereof. For example, data elements used to train the model of FIG. 9 may be used to train the model of FIG. 1.

It is noted that the implementations of the models described herein may be combined into a single model that performs all (or some) of the features described herein, for example, with reference to FIGS. 1-9.

At 1002, data is obtained. The data may be obtained by a monitoring process over a monitoring interval. The data may be obtained while the patient is automatically enteral fed by an enteral feeding controller. The data may be obtained from one or more components 202A-F.

The patient may be enteral fed according to a baseline feeding profile, which may include a target nutritional goal, as described herein.

One or more of the following exemplary data may obtained:

Output of sensors located on a feeding tube positioned for enteral feeding of the patient. The output of the sensors may include an indication of an estimated amount of fluid in the lung(s) of the patient, and/or an indication of an estimated spontaneous movement of the diaphragm of the patient. Additional details are described for example, with reference to U.S. patent application Ser. No. 16/000,922, and/or International Patent Application No. IB2017/057702.

Ventilation-related parameters denoting adjustable settings of the mechanical ventilator that automatically ventilates the patient, for example, rate of ventilations (e.g., per minute), tidal volume, percent of oxygen delivered, and the like. Additional details of exemplary adjustable ventilation parameters are described, for example, with reference to U.S. patent application Ser. No. 16/000,922.

Fluid-related parameters denoting actions taken and/or adjustable settings (e.g., of a controller) that affect patient fluid balance of the patient, for example, administration of diuretic medication, administration of antidiuretic medication, administration of intravenous fluid administration, amount of enteral fluid administration, and type of fluid being administered. Delivery may be, for example, manually by a nurse, automatically by the enteral feeding controller, by a medication dispenser, and/or by an IV fluid controller.

Patient-breathing parameter indicating how well the patient is current breathing, for example, SpO2, and/or other breathing and/or oxygenation related parameters.

Patient-fluid parameter indicating adjustment of fluid balance of the patient. For example, administration of diuretic medication, administration of antidiuretic medication, amount of urine outputted, time of urine output, concentration of urine output, and amount of fluid in lungs. The patient-fluid parameters may be obtained, for example, from the EHR, from sensors (e.g., an IV fluid controller), from urine sensors, and/or computed from output of the sensors on the feeding tube (e.g., fluid in lung).

At 1004, a training dataset is created by computing one or more feature vectors. Each feature vector stores (e.g., an indication of) the obtained data elements, including features computed from the output of the sensors located on the feeding tube, the ventilation-related parameters, the fluid-related parameters and/or optionally patient-breathing parameter and/or optionally patient-fluid parameters, for example, as a large vector where each value of each parameter is stored in an element of the feature vector.

Each feature vector may be associated with an indication of time during the monitoring interval indicating when the respective data element was obtained.

Alternatively, or additionally, individual data elements are each associated with an indication of time when the respective data element was obtained. The time may be stored as an element of the feature vector.

Each feature vector may store data elements obtained during a common time interval, for example, within a 10 minute interval, or other values.

At 1006, a model is trained and/or created based on the training dataset. The model is adapted to receive current outputs of the sensors located on the feeding tube and/or current patient-breathing parameters and/or current patient-fluid parameters and output instructions for adjustment of the mechanical ventilator and/or fluid balance. The adjustment of the mechanical ventilator and/or fluid balance may be for obtaining a target patient-breathing parameter (e.g., SpO2 of at least 90%, or at least 92%, or at least 95%, or other values) and/or a target patient-fluid parameter (e.g., at least 1000, or 1500, or 2000 cc of urine over 24 hours, or other values).

The model may be trained according to computed correlations between the patient-breathing parameter(s) and/or the patient-fluid parameter(s) and/or the output of the sensors located on the feeding tube and/or the ventilation-related parameters and/or the fluid-related parameters. The correlations may be indicative of which patient-breathing parameter(s) and/or the patient-fluid parameter(s) and/or the output of the sensors located on the feeding tube and/or the ventilation-related parameters and/or the fluid-related parameters, alone or in a combination, are associated with various values of target patient-breathing parameters and/or various values of target patient-fluid parameters.

At 1008, current outputs of the sensors located on the feeding tube and/or current values of the patient-breathing parameter(s) and/or current values of the patient-fluid parameter(s) are fed into the trained model. The model outputs instructions for adjustment of the mechanical ventilator, and/or the fluid balance. The adjustment may be selected for obtaining (i.e., increasing likelihood of reaching) the target patient-breathing parameter and/or the target patient-fluid parameter.

The instructions may be code for automatic execution by the mechanical ventilator and/or other controllers (e.g., enteral feeding controller to add fluid, IV fluid controller, add instructions to the EHR of the patient). The instructions may be for manual adjustment of the mechanical ventilator and/or actions to be performed, for example presented on a display, outputted text instructions, audio instructions, and/or a video. For example, instructions to add a diuretic medication, setting IV fluid rate, and/or set the ventilator.

At 1010, the ventilator and/or fluid balance are adjusted according to the instructions.

At 1012, one or more of features 1002-1010 are iterated over time. The receiving of data of 1002, the creating the dataset of 1004, and the training the model of 1006 are iterated over time to update the model with responses to the adjustment of the ventilator and/or fluid balance. The model learns the effects of its adjustment decisions, and iteratively improves the decision making ability to reach the target patient-breathing parameter(s) and/or the target patient-fluid parameter(s). Features of 1008-1010 are iterated over time for new data values using the updated model.

Figure 10:
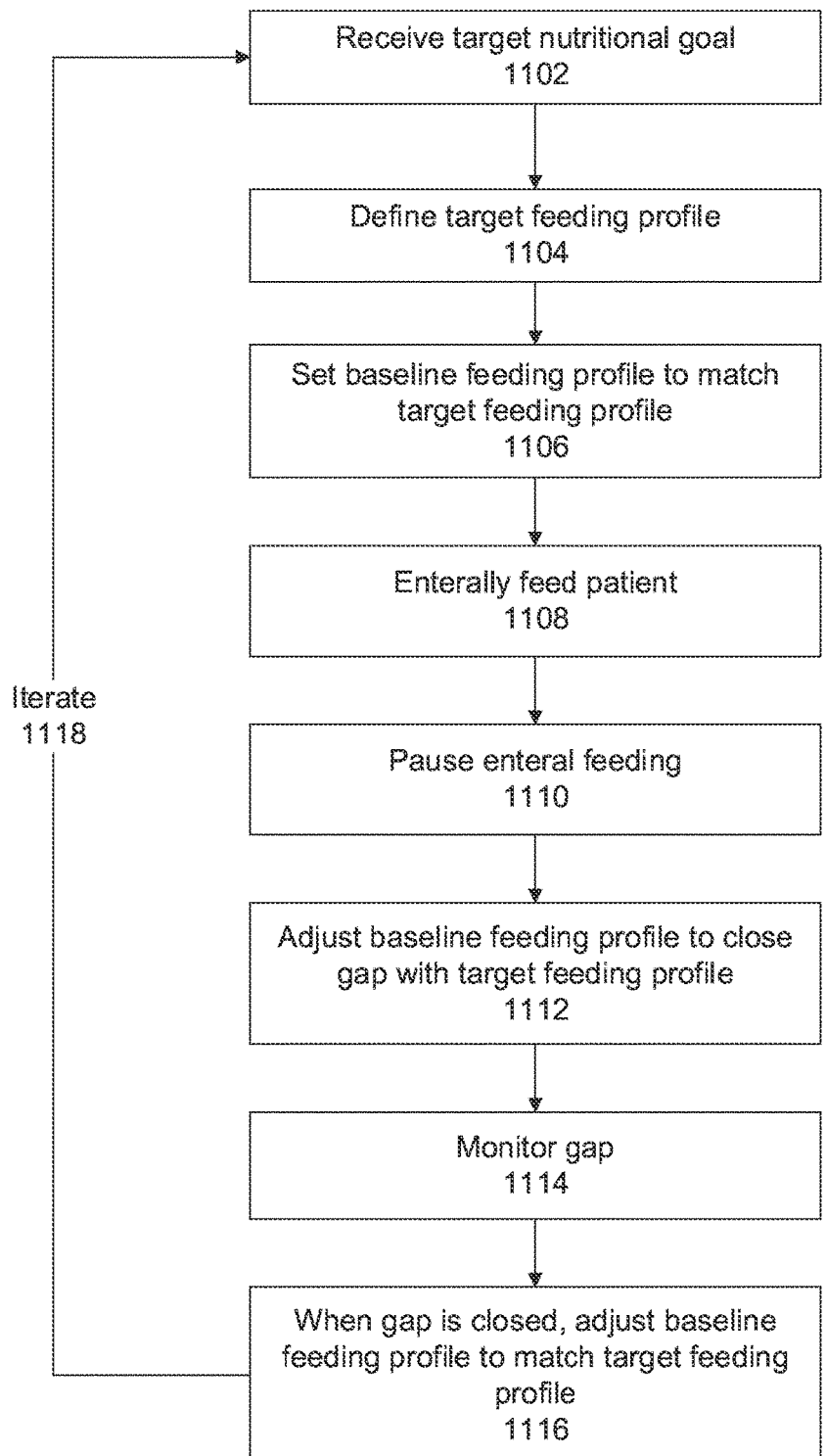
FIG. 10 is a flowchart of an exemplary method for dynamic adjustment of the baseline feeding for meeting a target nutritional requirement in view of pauses in feeding and/or dynamic changes to the target nutritional requirement, in accordance with some embodiments of the present invention.

Reference is now made to FIG. 10, which is a flowchart of an exemplary method for dynamic adjustment of the baseline feeding for meeting a target nutritional requirement in view of pauses in feeding and/or dynamic changes to the target nutritional requirement, in accordance with some embodiments of the present invention. The method described with reference to FIG. 10 may include, and/or substitute for, and/or be combined with, features and/or components described with reference to FIGS. 1-9.

It is noted that the model described herein may refer to the model of FIG. 1, and/or other models described herein, and/or combinations thereof. The method described with reference to FIG. 10 may be implemented by components of system 200 described with reference to FIG. 2.

Reference is also made to FIGS. 11A-11G, which are exemplary graphs of the target feeding profile and the baseline feeding profile over a time interval of 24 hours, to help understand the method described with reference to FIG. 10. A GUI may be created and presented on a display, for example, as a visual aid for the healthcare provider, to track the actual feedings in comparison to the target feeding profile, based on FIGS. 11A-11G.

At 1102, a target nutritional goal for automated enteral feeding of the patient may be received and/or set. The target nutritional goal may define a target accumulation of feeding parameters at an end of a time interval, for example, in 4, 6, 8, 12, 24 hours, or other time frames. The target nutritional goal may denote an accumulation of multiple enteral feeding parameters to reach at the end of the feeding time interval, for example, total volume of the enteral feeding, total number of calories to provide to the patient, amount of protein to provide to the patient, and/or other nutrients to provide to the patient (e.g., define multiple components of the feeding).

The nutritional goal may define a maximal limit for the feeding time interval, for example, maximum calories and/or maximum volume and/or maximum protein over 24 hours.

The target nutritional goal may be provided manually selected by a user and/or automatically computed by code. The target nutritional goal may be computed, for example, based on a resting energy expenditure (REE) computed based on calorimetry sensors (e.g., as described with reference to International Patent Application No. IL2017/051271), based on predictive equations (e.g., Harris-Benedict), by a classifier that is fed parameters associated with the patient feeding and trained on a training dataset of target nutritional goals of sample patients.

An exemplary process for setting the target nutritional goal is now described. It is noted that other methods may be used, and/or the exemplary method may be adapted. The process may be executed by a GUI presented on a display associated with the computing device. An REE calculation is performed for determining the energy amount the patient is using, in order to determine the target nutritional goal. The REE measurement duration is defined. Once the duration is set (e.g., while patient is in resting) the measurement is launched. The measurement may be stopped if the patient is restless or for any other reason. After the duration has elapsed, the REE is calculated from the accumulated $VCO_2$ measurement (e.g., by a $CO_2$ sensor). The results may be accepted, or if they seem erroneous, they may be rejected. Once the REE measurement is accepted, the food calculator may be launched. If the operator selects to exit this panel it returns to the regular REE panel. The food calculator assists in selecting the optimal feeding material based on the REE calculation, hidden calories (optional to insert this information by the user), protein calculation and other optional filters (e.g., low fiber). Based on the food calculator's parameters and the selected nutrition, the volume to be delivered (VTBD) and nutrition basal rate are determined, and may be edited by the user. The user is asked by the GUI to set Max rate (per hour) and Max VTBD (per the duration of the feeding time interval, for example 24 hours), this will enable automatic adjustments in order to compensate for feeding stop time (e.g., because of reflux events or routine procedures by the caregivers like bedding, CT scans, surgeries, and the like) and for the residual loss in the GRV residual bag (which is weighted and/or flow is measured by a GRV flow sensor). The GRV mechanism is for decompressing the stomach in reflux event and/or changes in REE estimations that is within the determined range of the user. When $VCO_2$ exceeds the range set (e.g., threshold changed by +\−15%), an alert is generated. If Max VTBD is defined a new kCAL/day target is automatically computed and proposed, along with a newly derived VTBD and nutrition rate. Once accepted, a new target nutritional goal is set. Additional exemplary details are described with reference to International Patent Application No. IL2017/051271.

Food type and/or additives may be selected a-priori by the physician and entered into the computing device based on the offering list presented to him/her according to the hospital available inventory. In another implementation, an updatable database of feeding materials is embedded in the computing device, or communicated to the computing device via the hospital system to create a personalized top list of the materials that fit the patient according to the baseline feeding profile.

Additional details of determining the target nutritional goal are described, for example, with reference to 102, where the term baseline feeding profile may refer to the target nutritional goal and/or to the term target feeding profile as described below. At 1104, a target feeding profile for reaching the target nutritional goal at an end of a time interval is defined. The target feeding profile may represent a rate of feeding. The accumulation of the feeding delivered at the set rate, at the end of the time interval, may represent the target nutritional goal. For example, the target nutritional goal is 2400 calories at the end of the next 24 hours, and the target feeding profile is a feeding rate of 100 calories per hour.

The target feeding profile may be computed for reducing risk of reflux, for example, as described herein.

The target feeding profile may be computed by the model, for example, as described herein.

At 1106, the baseline feeding profile is set. The baseline feeding profile is set by matching to the target feeding profile. The baseline feeding profile may be defined over the same time interval of the target feeding profile for reaching the target accumulation.

It is noted that the target feeding profile may not necessarily be explicitly defined. For example, the baseline feeding profile may be directly set based on the target nutritional goal without explicitly defining the target feeding profile. The target feeding profile may represent a conceptual step to help understand the process described herein. Alternatively, the target feeding profile may be explicitly defined and used as described herein, for example, when a GUI is presented on a display to the user, for example, based on the graphs described with reference to FIGS. 11A-11G.

At 1108, the patient is enterally fed according to the baseline feeding profile, for example, as described with reference to 104 and/or 116 of FIG. 1.

The baseline feeding profile indicates the actual feeding delivered to the patient. The target feeding profile indicates the desired feeding administered, which may not necessarily be what is actually administered, as described herein.

Figure 11A:
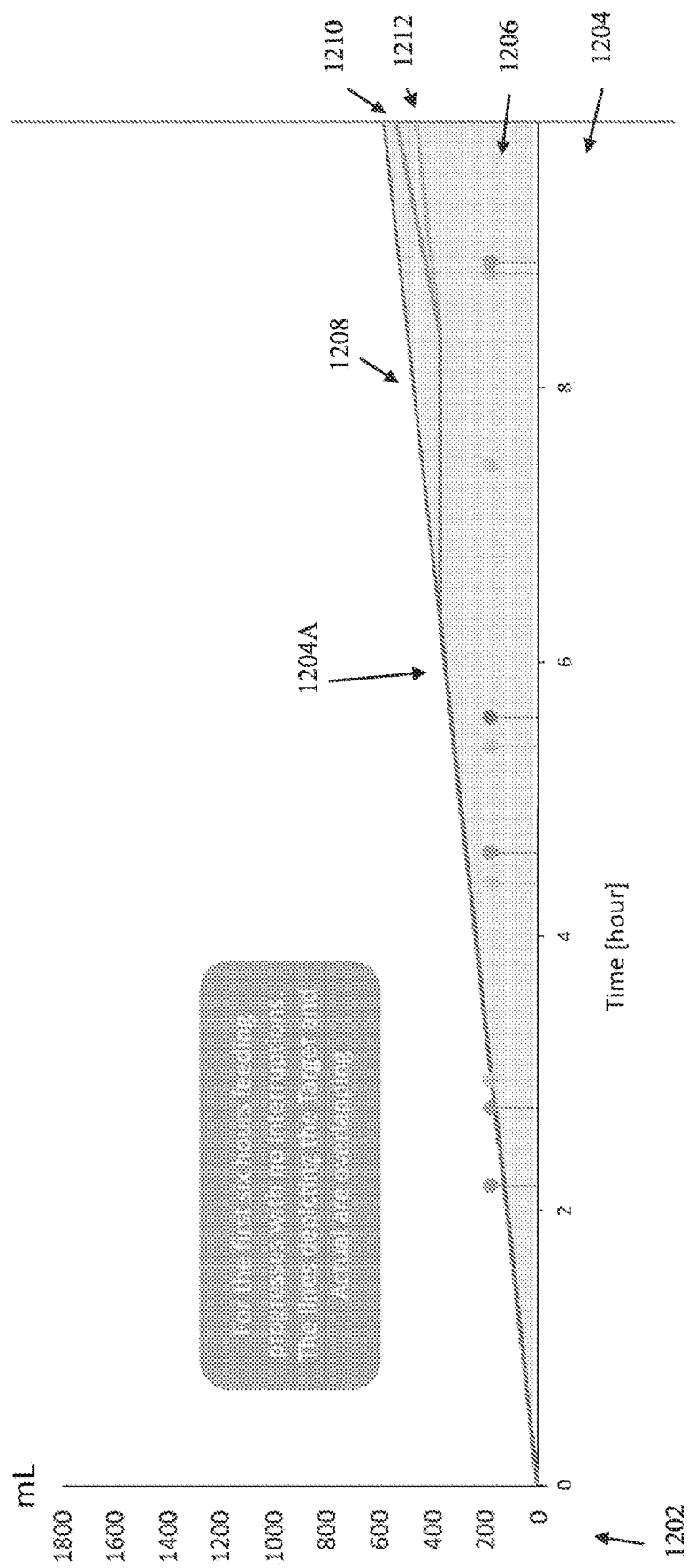
FIGS. 11A-11G are exemplary graphs of the target feeding profile and the baseline feeding profile over a time interval of 24 hours, to help understand the method described with reference to FIG. 10.

Referring now to FIG. 11A, graphs of accumulated feedings (in milliliters (mL)) over time are depicted. Y-axis 1202 depicts the accumulated feedings. X-axis 1204 denotes passage of time, from a start time of zero to an end time of 24 hours. Events 1206 occurring at different points in time that may sometimes cause a pause in feeding are depicted along x-axis 1204. Examples of events 1206 include: going for a CT scan, tracheal suction, routine position change, and medication bolus.

Graph 1208 indicates the target feeding profile. Graph 1210 indicates the baseline feeding profile. Graph 1212 indicates a conceptual standard feeding profile which is not dynamically adjusted as described herein, in order to help better understand and differentiate graph 1210.

It is noted that from the start (i.e., 0 hour) until the $6^{th}$ hour 1204A, the target feeding profile 1208 matches the baseline feeding profile 1210.

Referring now back to FIG. 10, at 1110, the enteral feeding is paused (e.g., by the enteral feeding controller) for one or more pause time intervals. A gap is formed between the target feeding profile and the baseline feeding profile during each pause time interval. The gap indicates the difference between the part of the target nutritional goal that the patient should have received, and the feedings that the patient actually received.

Additional details of pausing the enteral feeding are described, for example, with reference to 108 of FIG. 1.

Figure 11B:
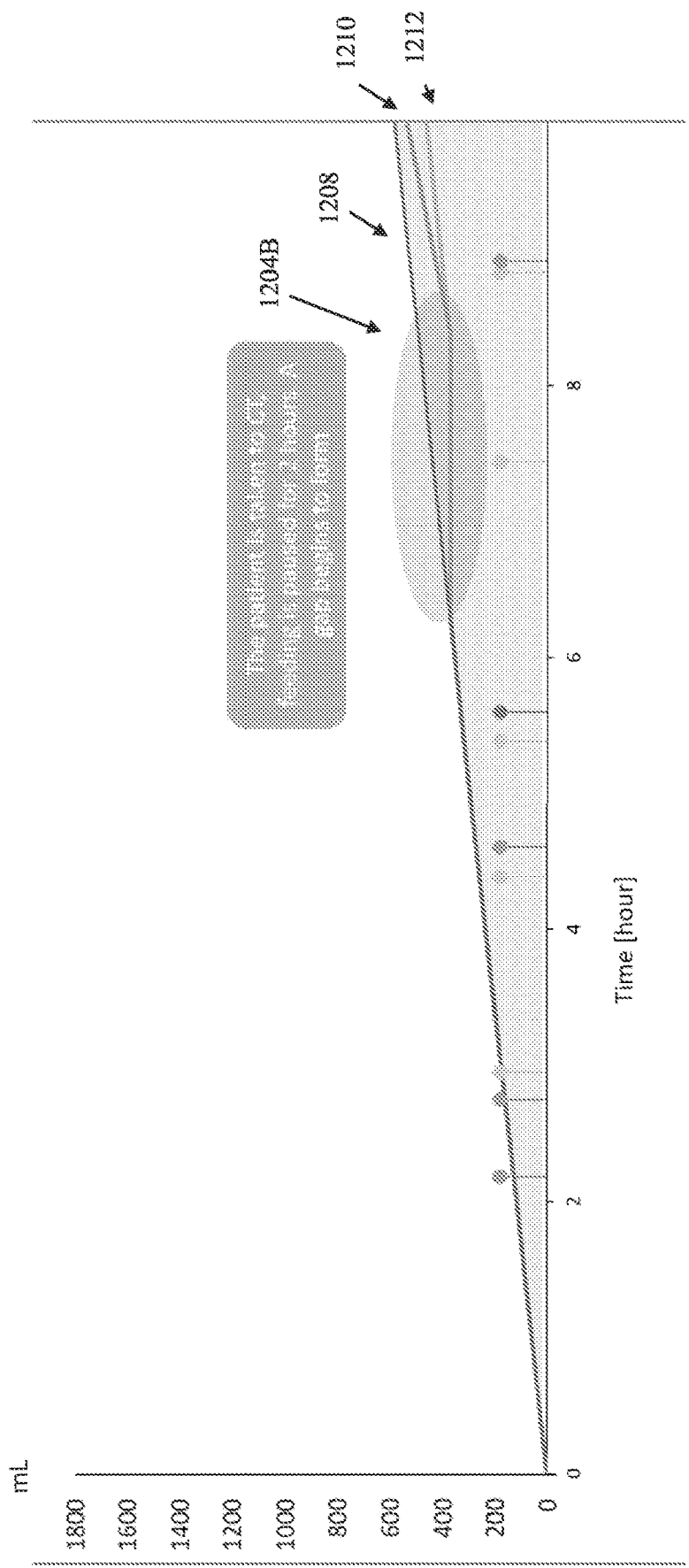

Reference is now made to FIG. 11B. At about 6.5 hours, the patient is taken for a CT scan. Feeding is paused for about 2 hours. A gap 1204B is formed between the target feeding profile 1208 and the baseline feeding profile 1210.

Referring now back to FIG. 10, at 1112, the baseline feeding profile is adjusted to a higher feeding rate than the previous feeding rate of the baseline feeding profile, which matches the feeding rate of the corresponding target feeding profile. In other words, the baseline feeding profile is adjusted to a higher feeding rate than the feeding rate of the corresponding target feeding profile.

The adjustment to the higher feeding profile is performed in an attempt to close (and/or reduce) the gap for reaching the target accumulation at the end of the time interval.

Optionally, the baseline feeding profile is adjusted to a defined maximal feeding rate. The maximal feeding rate may indicate a maximum feeding rate which is not to be exceeded by the feeding controller. The maximal feeding rate may be computed according to a risk of likelihood of future reflux event below a requirement for no scheduled and/or predicted reflux-related parameters, for example, by the model. Alternatively or additionally, the maximal feeding rate may be manually selected by a user (e.g., physician). The maximal feeding rate may be set according to a feeding rate tolerated by an enterally fed patient for which risk of reflux events are low (i.e., no expected upcoming change of patient position that increase risk of reflux event), for example, computed by the model and/or manually set by a user.

Figure 11C:
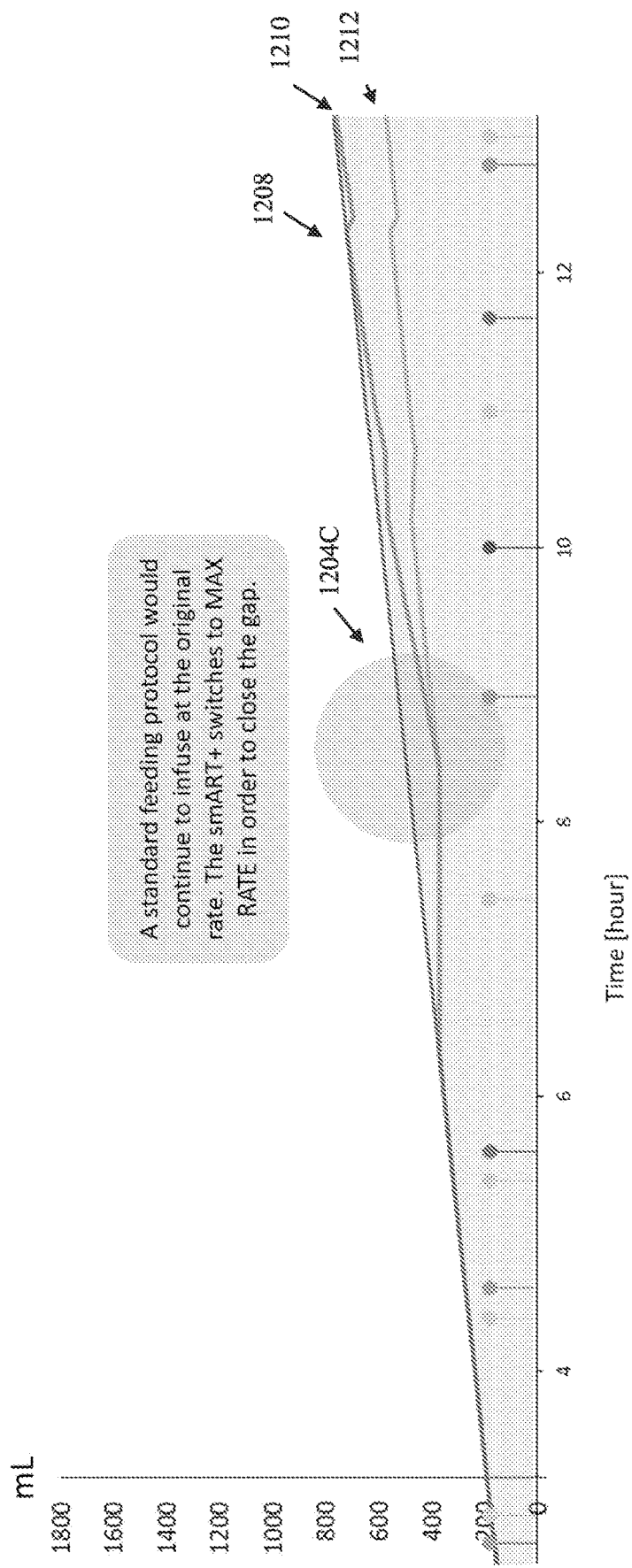

Reference is now made to FIG. 11C. After about 8.5 hours, when the patient returns from the CT scan, the feeding is resumed. At 1204C, the feeding rate of the baseline feeding profile 1210 is adjusted to a higher rate than the feeding rate of the corresponding target feeding profile 1208. The feeding rate of the baseline feeding profile 1210 may be adjusted to the maximal feeding rate. It is noted that for comparison purposes, the standard feeding protocol 1212 is simply resumed to its previous rate after the pause. It can be visually seen that the standard feeding protocol 1212 will never close the gap with the target feeding profile 1208, while the higher rate of the baseline feeding profile 1210 will eventually intersect (i.e., close the gap) with the target feeding profile 1208.04

Figure 11D:
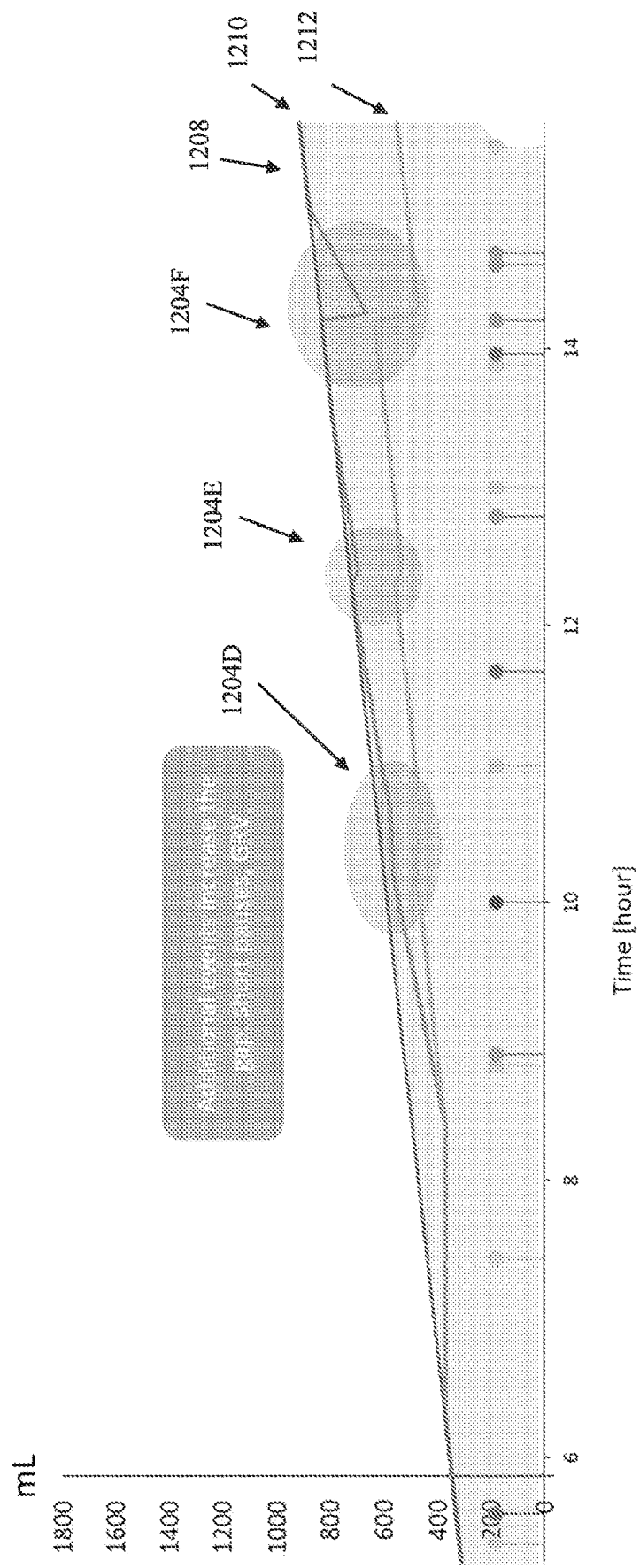

Reference is now made to FIG. 11D. Multiple pauses in feeding are depicted 1204D-F. After each pause, the feeding is resume by adjusting the baseline feeding profile 1210 to the higher rate (e.g., the maximal rate) in an attempt to eventually close the gap with the target feeding profile 1208. The gap is successfully closed as shown. Referring now back to FIG. 10, at 1114, the gap between the target feeding profile and the baseline feeding profile may be monitored. The closing of the gap may be detected. The closing of the gap may be defined, for example, by a requirement, such as a range of values that define when the gap is closed. For example, the gap may be closed when the actual feeding is within about 100 calories, or about 50 calories, or other values, of the target nutritional goal. It is noted that an exact match (i.e., gap of zero) is not necessarily required.

At 1116, when the gap has been determined as being closed, the feeding rate of the baseline feeding profile may be adjusted down (i.e., reduced), to match the feeding rate of the target feeding profile.

Figure 11E:
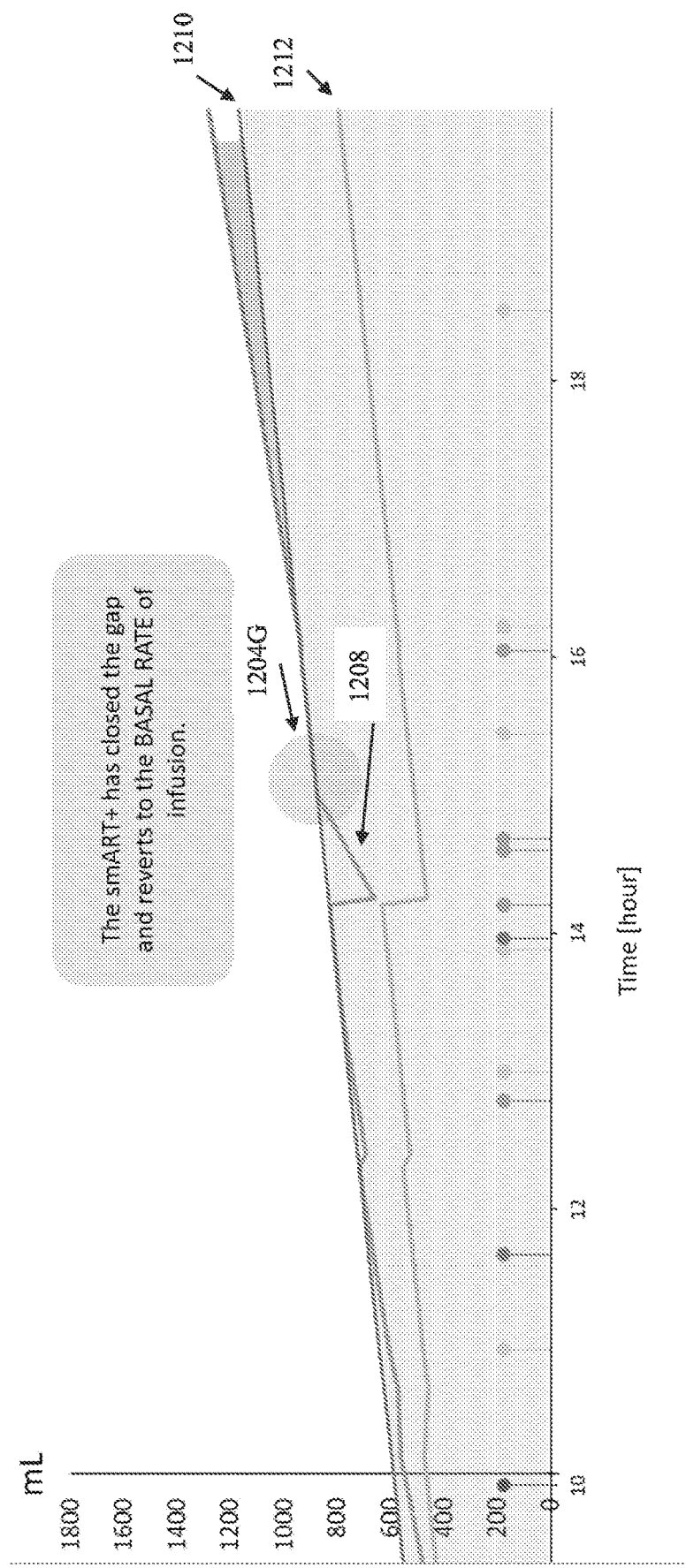

Reference is now made to FIG. 11E. At 1204G, when the gap between baseline feeding profile 1210 and target feeding profile 1208 has been closed, the feeding rate of the baseline feeding profile 1210 may be adjusted back to match the feeding rate of the target feeding profile 1208.

Referring now back to FIG. 10, at 1118, one or more features described with reference to 1102-1116 are iterated. The features 1102-1116 may be iterated over the time interval, and/or may be iterated over multiple sequential time intervals.

Optionally, the model is updated based on the iterations described with reference to 1102-1116, for example, as described herein and/or with reference to 110 of FIG. 1.

In an exemplary iteration, at 1102, the target nutritional goal is dynamically adjusted, for example, due to changes in the patient's medical condition. Such changes in the medical conditions may translate into additional calories, and/or change in mix of nutrition (e.g., higher percentage of protein) and/or a reduction in calories. At 1104, the target feeding profile for reaching the dynamically adjusted target accumulation of enteral feeding parameters at the end of the time interval is dynamically adjusted. At 1106, the baseline feeding profile is dynamically adjusted to the adjusted target feeding profile, to correspond to the dynamically adjusted target nutritional goal.

Figure 11F:
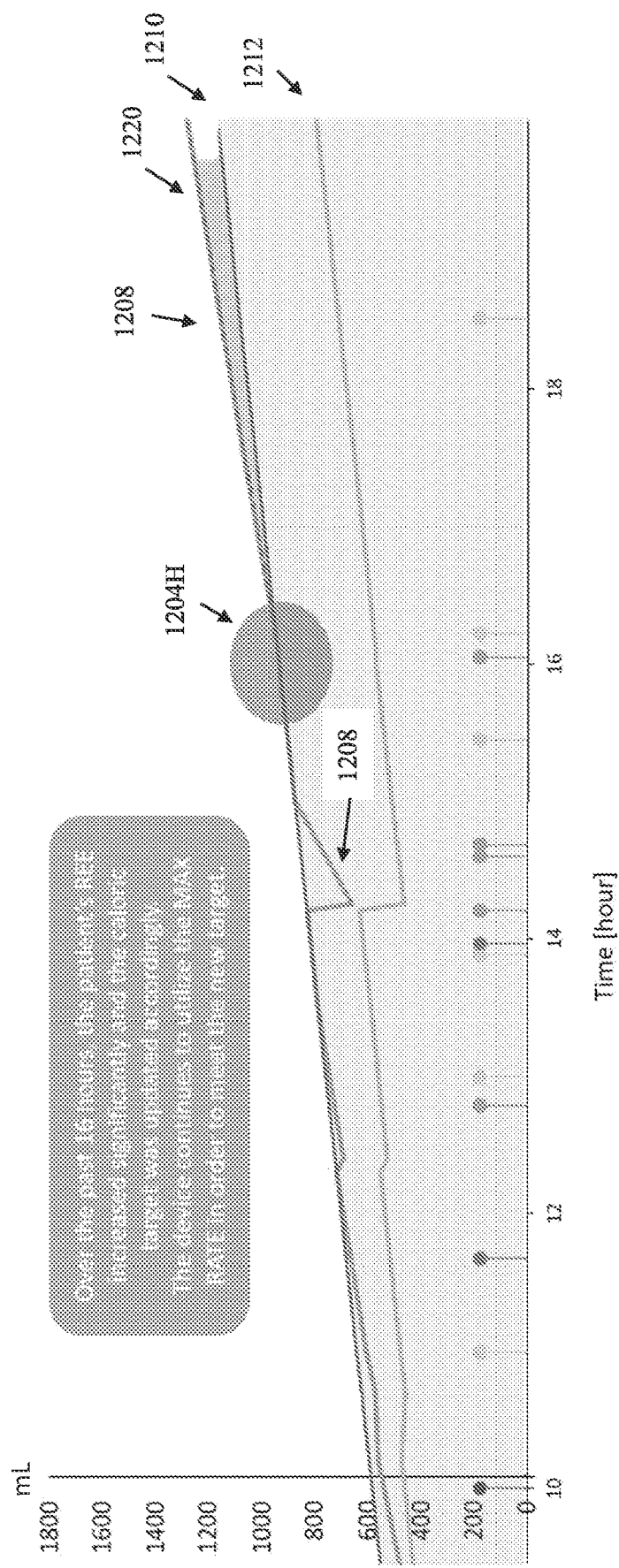

Reference is now made to FIG. 11F. At 1204H, the patient's REE increased significantly, triggering an increase in the target nutritional requirement to reach at the end of 24 hours. The original target feeding profile 1210 is dynamically adjusted, creating an adjusted target feeding profile 1220, according to the updated target nutritional requirement. The feeding rate of the baseline feeding profile 1208 is adjusted to match the adjusted target feeding profile 1220.

Figure 11G:
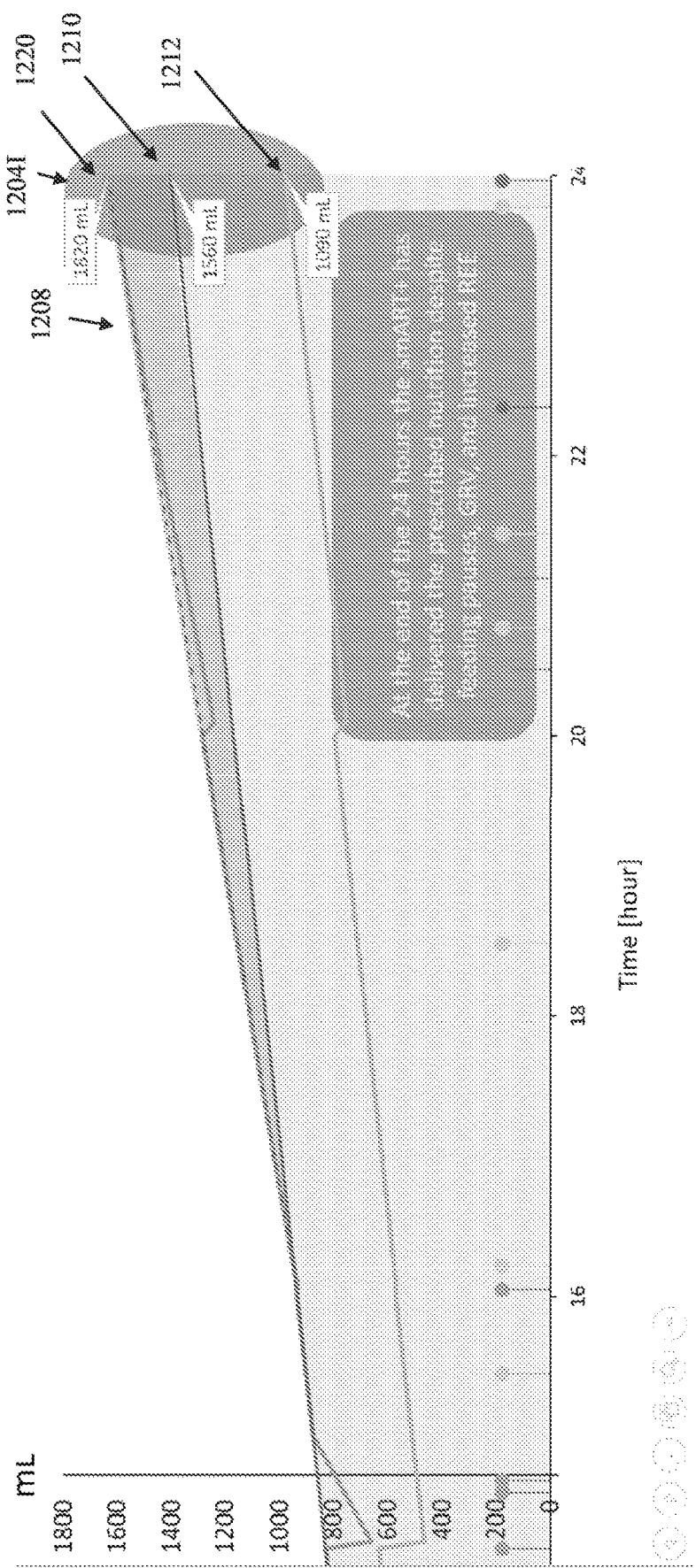

Reference is now made to FIG. 11G. At the end time interval of 24 hours 1204I, the dynamically adjusted baseline feeding profile 1208 that matches the dynamically adjusted feeding profile 1220 achieved the dynamically adjusted target nutritional goal at the end of 24 hours of 1820 mL (e.g., within a tolerated error range). The dynamic target nutritional goal was met, despite pauses in feedings, and/or despite changes in patient nutritional requirements (e.g., increased REE). In comparison, without the dynamic adjustment of the nutritional feeding requirement, the original target feeding profile 1210 would meet the original nutritional target of 1560 mL, which has not kept up with changing patient nutritional requirements. In yet another comparison, without the dynamic adjustment of the feeding rate to compensate for pauses in feeding 1212, only 1090 mL of feeding would be provided to the patient.

Various embodiments and aspects as delineated hereinabove and as claimed in the claims section below find computed support in the following examples.

EXAMPLES

Reference is now made to the following examples, which together with the above descriptions illustrate some embodiments in a non limiting fashion.

Figure 12:
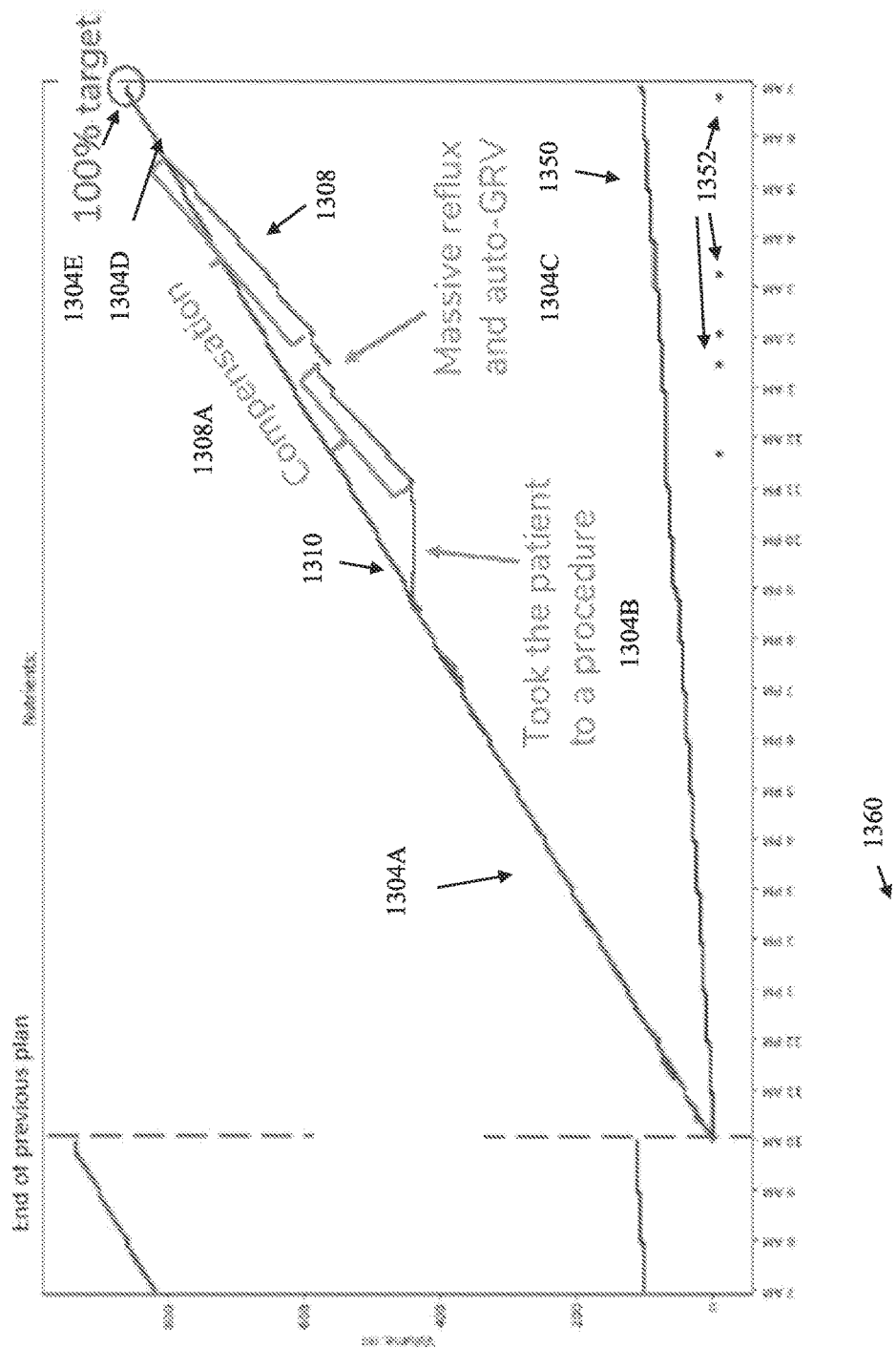
FIG. 12 is a graph presenting experimental results of an experiment performed by the Inventors for assessing ability of a system that automatically enterally feeds a patient to meet a target nutritional feeding requirement in view of reflux events and/or pauses in the enteral feeding, in accordance with some embodiments of the present invention.

Reference is now made to FIG. 12, which is a graph presenting experimental results of an experiment performed by the Inventors for assessing ability of a system that automatically enterally feeds a patient to meet a target nutritional feeding requirement in view of reflux events and/or pauses in the enteral feeding, in accordance with some embodiments of the present invention. The graph depicts time on the x-axis. The time interval is from 10 AM to 7 AM the next day. The total volume administered is depicted on the y-axis.

Curve 1310 denotes the target feeding profile, which indicates the desired feeding rate, for meeting a target nutritional requirement 1304E (representing 100% of the nutritional goal at the end the time interval), as described herein.

Curve 1308 denotes the baseline feeding profile, indicating the actual feeding rate administered to the patient.

Between about 10 AM and 8:30 PM (denoted by element 1304A), baseline feeding profile 1308 matches target feeding profile 1310.

Between about 8:30 PM and 11:30 PM (denoted by element 1304B), the enteral feeding is paused due to the patient being taken to a medical procedure. A gap is formed between baseline feeding profile 1308 and target feeding profile 1310.

Between about 11:30 PM and 5:30 AM (denoted by element 1304C), the feeding rate of baseline feeding profile 1308 is increased, optionally to the maximum value, denoting a compensation rate 1308A that compensates for the long pause in feeding of 1304B. It is noted that feeding is paused for short periods of time during reflux and/or auto- GRV 1304C and then resumed. Reflux events are shown as dots marked by element 1352 at times corresponding to 1304C. Reflux events may be used to update the model as described herein, and/or for adjusting the feeding rate of the baseline feeding profile, as described herein.

At about 5:30 AM (denoted by element 1304D), the gap between baseline feeding profile 1308 and target feeding profile 1310 has been closed.

From about 5:30 AM until 7:00 AM (denoted by element 1304E), the feeding rate of baseline feeding profile 1308 is reduced to match the rate of target feeding profile 1310.

The 100% target 1304E at the end of the time interval is reached at the end of the time interval (within a tolerance range).

Graph 1350 shows the rate of water administered to the patient, at a constant rate over the time interval.

The following summarizes the experimental results. The target nutritional requirement to reach by the end of the time interval (i.e., "Total nutrition prescribed") is 979 ml. Target feeding profile 1310 is set to meet the target nutritional requirement. The feeding actually administered to the patient (i.e., "Total nutrition") is 978 ml, representing a feeding efficiency of 99.90%. Baseline feeding profile 1308 represents the dynamically adjusted feeding rate of the feedings actually administered to the patient. It is noted that the feeding efficiency without compensation, which would otherwise be delivered if the baseline feeding profile is simply paused, without adjusting the rate for compensating for gaps, is 84.45%. Of note is that 115 ml of water were administered over the time interval.

Figure 16:
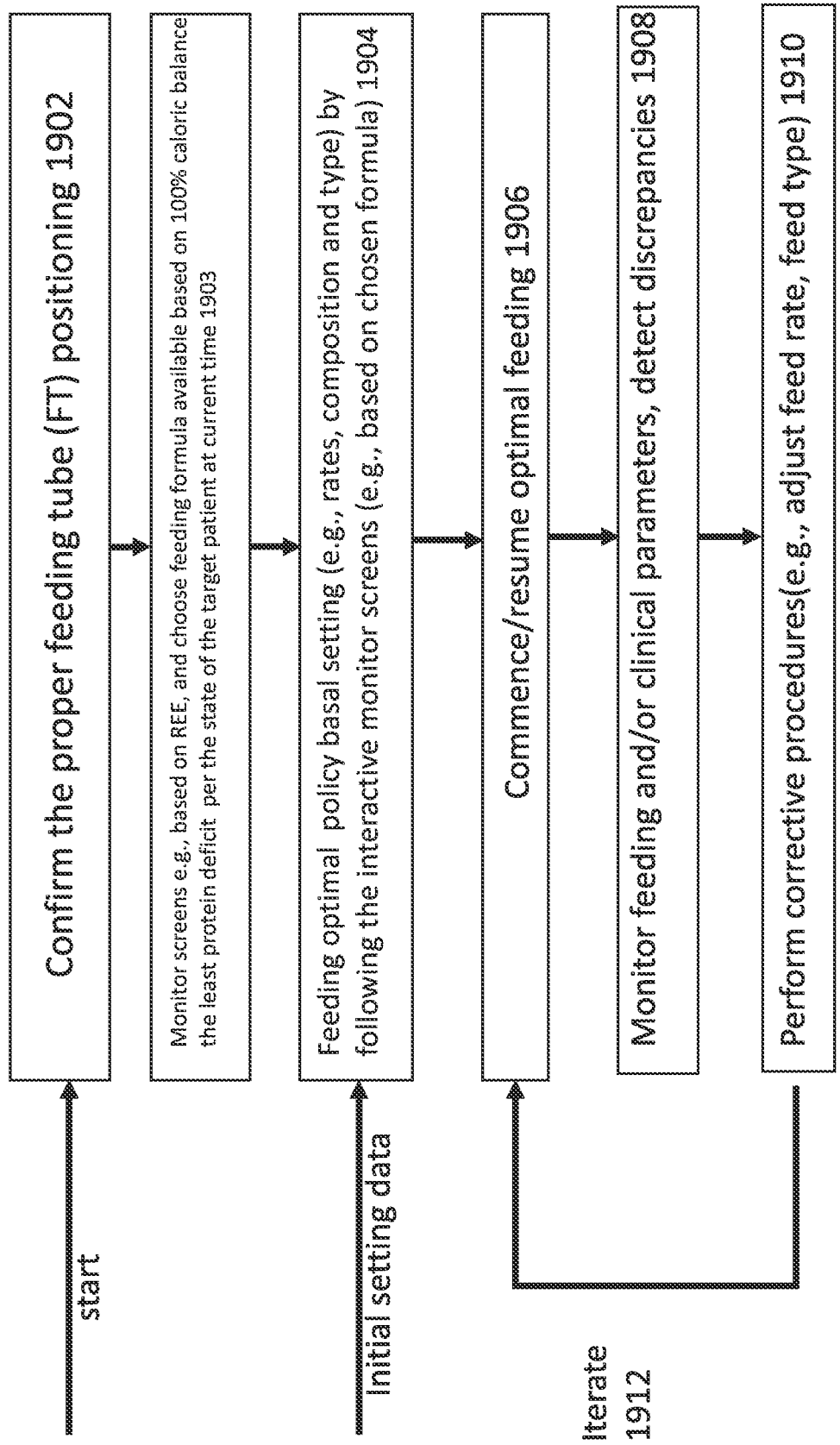
FIG. 16 is a flowchart of an exemplary method of operational flow of an automated patient feeding device, in accordance with some embodiments of the present invention.

Reference is now made to FIG. 16, which is a flowchart of an exemplary method of operational flow of an automated patient feeding device, in accordance with some embodiments of the present invention. Features described with reference to FIG. 16 may be combined, integrated, replaced, and/or added to other features of other systems and/or methods described herein, and/or described with reference to other FIGS. described herein.

At 1902, the proper position (i.e., target location when feeding) of the feeding tube within the patient is confirmed, for example, as described herein, for example, using a GUI described with reference to FIG. 13.

The GUI may depict a schematic of an outline of a body of the patient including an indication of a current location of the feeding tube. The tube is maneuvered until the GUI image confirm the correct position, for example, by a message, color coding, and/or other indication. Tube location may be detected, for example, using impedance sensors to determine location within the stomach, and/or relative to the LES.

Optionally, feeding is prevented from automatically starting when the feeding tube is detected as being outside the target location. For example, additional features of the GUI for starting and/or selecting feedings are not presented until the tube is located at a target zone. The confirmation of the proper location of the feeding tube may indicate a start of the feeding process.

The location of the feeding tube may be dynamically monitored, and fed as a parameter (e.g., gastric parameter) into one or more of the models described herein. For example, location of the feeding tube may correlate with risk of reflux.

At 1903, one or more feeding formulas (also referred to herein as formulations) may be selected, for example, from a list of candidate and/or available formulas. The list of candidate formulas may be manually and/or automatically selected, for example, based on REE and/or other patient parameters (e.g. as described herein, such as urine output), such as the medical state of the target patient (e.g., based on manually entered data, and/or data obtained from the electronic health record). For example, to provide 100% (or near 100%, for example, within a tolerance range, for example, within 90% or 95%) of the target nutritional goal of the patient. Supplemental protein may be selected to provide additional protein when the selected nutritional formula is lacking sufficient protein to meet the nutritional goal of the patient. The nutritional goal may be set according to the REE and/or other patient parameters, for example, using predictive equations as described herein.

The feeding formulas may be selected using an interactive graphical user interface (GUI), which may present values of the REE and/or other patient parameters. The selected feeding formulas and/or the REE and/or other patient parameters may be fed into the model(s) described herein, for example, for computing adjustments to the baseline feeding profile and/or predicting risk of reflux event, and/or other predictions as described herein.

Optionally, one or more interactive GUIs are presented on a display, and used by a user for setting up the baseline feeding profile and/or target feeding profile. For example, the GUI may present additional patient data, for example, obtained from sensors, and/or patient data presented in the electronic medical record. The additional patient data may be used to compute the REE and/or baseline feeding profile and/or target nutritional profile, and/or for selecting from available feeding formulations, as described herein.

Initial setting data (e.g., REE, initial patient status) may be received (e.g., from sensor data, manually entered by the user, from the patient's electronic health record). The initial setting data may be used to set the feeding policy, as described herein.

Optionally, the daily nutrition requirement (e.g., the target nutritional goal) for the patient is as calculated from according to the REE computed based on measurements of $CO_2$ expiration level and/or $O_2$ consumption, which may be measured by sensor(s).

The calculation (e.g., of the baseline feeding profile and/or target feeding profile) may include available suitable nourishment(s) (e.g., in stock), optionally optimal nourishment, and/or extra protein and/or the hidden calories carried by medication. The user may select the feeding formulations to be provided to the patient from a list of available suitable feeding formulations (e.g., presented in the GUI), such as the available formulations that are closest in matching to the caloric needs and/or protein requirements of the patient. Additional water for proper system operation may be automatically computed and added to the feeding schedule (e.g., the baseline feeding profile and/or target feeding profile). Supplemental protein may be presented for selection (e.g., brand and/or quantity), for example, based on protein deficiency in the presented feedings. Supplemental protein may be selected from dedicated protein sources which may be added to the selected feeding formulation. Optionally, the presented nourishments are filtered according to the patient's medical condition (e.g., manually entered by a user and/or extracted from the electronic health record of the patient), for example, certain nourishments are excluded for diabetics and/or those with cardiovascular disease.

Optionally, the most suitable nourishment (i.e., feeding formulation) available is presented in the GUI for selection, and/or selected, based on protein requirements while matching the measured REE measured and supplemental protein to add to the feedings provided to the patient. "Hidden" calories carried by the extra protein and/or medication are compensated. When medications are prescribed to the patient, the calories the patient receives from the medication itself (referred to herein as hidden calories) are considered as part of the overall baseline and/or target feeding profile, included in the overall energy balance for the patient. The baseline feeding profile and/or target feeding profile may be set according to the selected available feeding formulations, supplemental protein, and/or hidden calories from the supplementation protein and/or medications.

At 1904, one or more feeding policy settings are defined, optionally using a designed user interface, for example, an interactive GUI, as described herein. Exemplary feeding policy settings include: rate of feeding, baseline feeding profile, target feeding profile, target nutritional goal, nutritional composition of feeding (e.g., water, protein), and/or type of feeding, as described herein.

Optionally, the user may use interactive GUIs, which may direct the user for setting the proper values for the feeding program (e.g., selecting parameters for the baseline feeding profile and/or target feeding profile).

Optionally, based on the REE (e.g., presented in the GUI), the feeding rate (e.g., in kiloCalories per day (kCal/day)) is computed, for example, the baseline feeding rate and/or target feeding profile is in the range of about 15-100 milliliters per hour (ml/hr), or about 700-2500 kCal/day.

Feeding may start gradually (e.g., as selected by the operator and/or predefined and/or automatically computed), for example, during the first 4 days, the following percentage of the target nutritional goal and/or baseline feeding profile and/or target feeding profile is set: 30% for the first day, 50% for the second day, 70% for the third day, and 100% for the fourth day, are set. It is noted the percentages are examples of value and not necessarily limiting.

The target nutritional requirements may be matched (e.g., exactly and/or approximately within a tolerance range, optionally a closest but not necessarily exact match) to the existing nutritional inventory available to the feeding facility (e.g., stored in the hospital). Optionally extra protein is added (e.g., manually by the user and/or automatically selected by code) depending on patient medical status.

Optionally, maximum feeding rates (i.e., used to compensate when the baseline feeding profile falls below the target feeding profile, as described herein) may be defined, for example, as straight broken lines 1606 described with reference to FIG. 15A. The maximal feeding rate defines a pumping rate (i.e., feeding rate) should never be exceeded, for example, when compensating for feed halts due to reflux, treatments, procedures, and/or GRV events, as described herein. A final setup inspection may be performed. Triggering a START command (e.g., pressing a start icon on the GUI) initiates the fully automatic feeding, as described herein.

Final initial settings of the feeding controller (e.g., baseline feeding profile and/or target feeding profile and/or target nutritional goal) for feeding the patient may be presented, for example, within the GUI. Exemplary settings include maximum rate and/or maximum volume to be delivered (VTBD). The VTBD may be defined for a time interval, for example, 6 hours, 12 hours, 24 hours, or other values. The GUI may present a visual snapshot of the feeding plan (e.g., baseline feeding rate, target feeding profile, nutritional target, maximal adjustment rate) for review by the healthcare provider.

The following are exemplary equations representing relationships of variables described herein in mathematical terms:

$$CT\left[\frac{kCal}{day}\right] = \text{caloric } dailytarget = REE \cdot (\% \text{ plan}) - \text{hidden calories}$$

$$VTBD(\text{volume to be delivered}) =$$
$$\left(CT / \text{caloric value of nutrient} \cdot \frac{duration}{24}\right) [ml]$$

$$VTBD \text{ rate} = \frac{VTBD}{duration}\left[\frac{ml}{hr}\right]$$

$$\text{max rate} = \text{basal rate} \times 1.75 \ (\textit{defoult})$$

Max VTBD rate=VTBD rat×1.2 (or by physician instruction)

CT denotes the caloric target (e.g., daily), i.e., target nutritional goal at the end of the time interval.

REE is as described herein

% Plan denotes the percentage of the maximal total nutritional goal that is gradually increased per day, as described herein.

Hidden calories denotes the calories in medications that are excluded from the target nutritional goal, since the calories will be provided in the prescribed medications.

Caloric value of nutrient denotes the calories in the selected feeding formulation.

Duration denotes a certain time interval from a daily 24 hours, over which the target and/or baseline feeding profile are defined.

It is noted that overall values may be used to compute the maximum feeding rate (i.e., max rate) from the basal rate (i.e., the baseline feeding rate), for example, from the range of 1.5-2, or 1.7-1.9, or 1.6, 1.7, 1.8, 1.9, or other values.

It is noted that overall values may be used to compute the maximum VTBD rate (i.e., max VTBD rate) from the VTBD rate (i.e., the baseline feeding rate to reach the defined VTBD target at the end of the time interval), for example, from the range of 1.1-1.4, or 1.1-1.3, or 1.1, 1.3, 1.4, 1.25, or other values.

The setup procedure may include one or more of the following features, for example, as described herein:

Present interactive popup screens (e.g., GUI) for parameters initiation, optionally based on sensors input and/or data stored in the electronic health record.

Identifying one or more best protein matching feeding formulas (e.g., available at the feeding site).

Calculating the extra protein to be provided as a supplement to the patient. The supplemental protein may be included in the baseline feeding profile and/or the target feeding profile.

Define a flexible feeding schedule including on/off feeding pause periods.

An Exemplary target feeding profile (i.e., feeding plan) computed for the target patient may include one or more of:

Display of REE information (e.g., dynamically updated in real time)

Rate ranges e.g. 15-100 mL/hour, and kCal/day 700-2500 kCal/day

Define gradual increase in percentage of target nutritional goal defined per time interval (e.g., per day), for example, define 4 day percentage escalation and fixed percentage thereafter—e.g. 30% on day 1, 50% on day 2, 70% on day 3, 100% on day 4, and thereafter 100%.

Selection of feeding formulations (i.e., nutrients) from a list of in-stock formulations (e.g., the hospital). Optionally, when a certain formulation has run out, another available formulation that best matches to the patient requirements (as described herein) is presented and/or selected.

Target feeding profile and/or baseline feeding profile takes into account one or more of: patient weight, protein factor (e.g., increased protein requirements over what is available in standard formulations) and/or protein tolerances, (+−grams) of protein that don't need to be compensated for (e.g. +5 g, −10 g).

Intermittent mode (i.e., on/off) and/or number of meals and/or interval (e.g., at top rate range, controlled by reflux detection).

Water per required urine output level.

Press start fully automatic mode.

At 1906, feeding is commenced. The patient is automatically fed using the feeding tube, as described herein. The feeding may gradually be increased as set. Alternatively, when feeding has been paused (e.g., due to a procedure, as described herein), feeding commences.

The feeding may be performed in a fully automated and/or semi-automated manner. For example, instructions are generated for controlling a pump and/or valve (e.g., pinch valve) to deliver and/or pause feedings, without necessarily requiring intervention by a human user.

Feeding may be automatically provided to the patient according to one or more of the following features, for example, as described herein:

Closed loop operation (i.e., fully automatic).

Automatic compensation of the feeding rate to catch-up with feed losses, for example due to GRV events and/or feed halting due to reflux or result of treatment.

Water flow rate (i.e., supplemental water provided to the patient) adjusted according to urine output, for example, matching the urine output, and/or increased to increase urine output, and/or decreased to decrease urine output.

Matching (e.g., within a tolerance range) the instantaneous REE to the feeding rate, for example, at preassigned intervals i.e. update the feed flow correspondingly.

At 1908, one or more parameters are monitored, as described herein. Exemplary monitored parameters include one or more of: urine status, REE, $CO_2$ measurements (e.g., from patient expiration), $O_2$ measurements (e.g., from patient inhalation), feeding plan (e.g., baseline feeding profile, target feeding profile), and/or showing one or more feeding tube related indicators: reflux, tube position and/or GRV, gastric reflux-related parameters, gastric reflux events, other feeding parameters and/or clinical parameters, as described herein. The parameters may be fed into the model, as described herein. Discrepancies may be detected, as described herein.

Optionally, a real time REE is computed based on the monitored $CO_2$ and/or $O_2$ measurements. The real time REE may be fed as input for dynamically adjusting the baseline feeding profile, for example, the REE is fed into the model, as described herein.

Optionally, a real time indication of the parameters is presented within the GUI, providing a working screen presenting the real time status of the patient.

Optionally, one or more graphs are created and presented (e.g., within a GUI) based on the monitored parameters, for example, as described with reference to FIGS. 15A-15B.

The exemplary following features may be automatically implemented during the fully automated feeding procedure, and/or during the monitoring of the parameters:

Every set time interface (e.g., half hour, hour, or other value) the actual energy expenditure may be measured, for example, based on sensors that estimate $CO_2$ and/or $O_2$ values, as described herein.

The actual feedings (e.g., volume, weight) to be delivered may be adjusted automatically accordingly (e.g., the baseline feeding profile is adjusted). For example, at an initial time interval the target feeding profile and/or baseline feeding profile is initially set to 30 [kCal/hr], for example, based on REE measurements and/or output of the model. At a subsequent time interval, the actual measured REE is 33 [kCal/hr]. Instructions for adjustment of the baseline feeding profile (i.e., feeding pump and/or feeding controller) according to the updated value of the REE may be generated, for example, to increase the feeding rate to match the updated REE value. The actual feeding by the pump and/or controller is correspondingly adjusted to the adjusted baseline feeding profile.

Feeding halts and/or GRV, which represent actual losses of feeding (i.e., GRV) and/or loss of potential feeding (i.e., time during which feeding has not been delivered due to halts) are compensated for automatically, for example, by increasing the feeding rate to the maximal defined rate, in order to close the gap between the actual feedings (i.e., baseline feeding profile) and the target feeding profile, as described herein.

Present and dynamically update in real time, a snap review monitor screen (e.g., GUI) that presents real time values of one or more parameters, for example, REE, urine rate, and the like. The parameters may be used to compute and/or adjust the baseline feeding rate.

Present warnings in the GUI, for example, as pop-up windows. For example, when values of parameters deviate from a defined target zone.

When feeding and/or water contains are exhausted or about to become empty in the near future. Best matching replacements may be presented in the GUI for selection.

Container replacement may be followed by an automatic priming cycle.

Optionally, one or more alarms and/or intermitted indications are generated, for example, when values fall out of defined normal and/or safe values. The alarms and/or indications may be presented within the GUI, such as showing current state (e.g., normal, safe, and/or not-normal and/or risky), for example, as described with reference to FIG. 13. Exemplary alarms and/or indications include one or more of: REE, Urine, GRV, reflux, replace drainage bag, nutrient currently being fed to patient (e.g., type), warning when current nutrient will be running out (or has run out), and water runout warning.

At 1910, one or more corrective procedures are performed. The feeding pay be paused during the corrective procedure. For example, the refluxing material is evacuated from the patient, and/or the baseline feeding profile (and/or other feeding policy settings) is adjusted, as described herein. In another example, feeding is paused while the patient is taken for imaging, to clear the tracheal tube, and/or for other procedures as described herein.

At 1912, features described with reference to 1902-1910 are iterated, for example, over a time interval while the patient is enterally fed, until the patient resumes eating without a tube.

The actual energy expenditure of the patient may be continuously measured, for example, based on the REE and/or other parameters as described herein. The baseline feeding profile may be dynamically adapted, as described herein.

Figure 13:
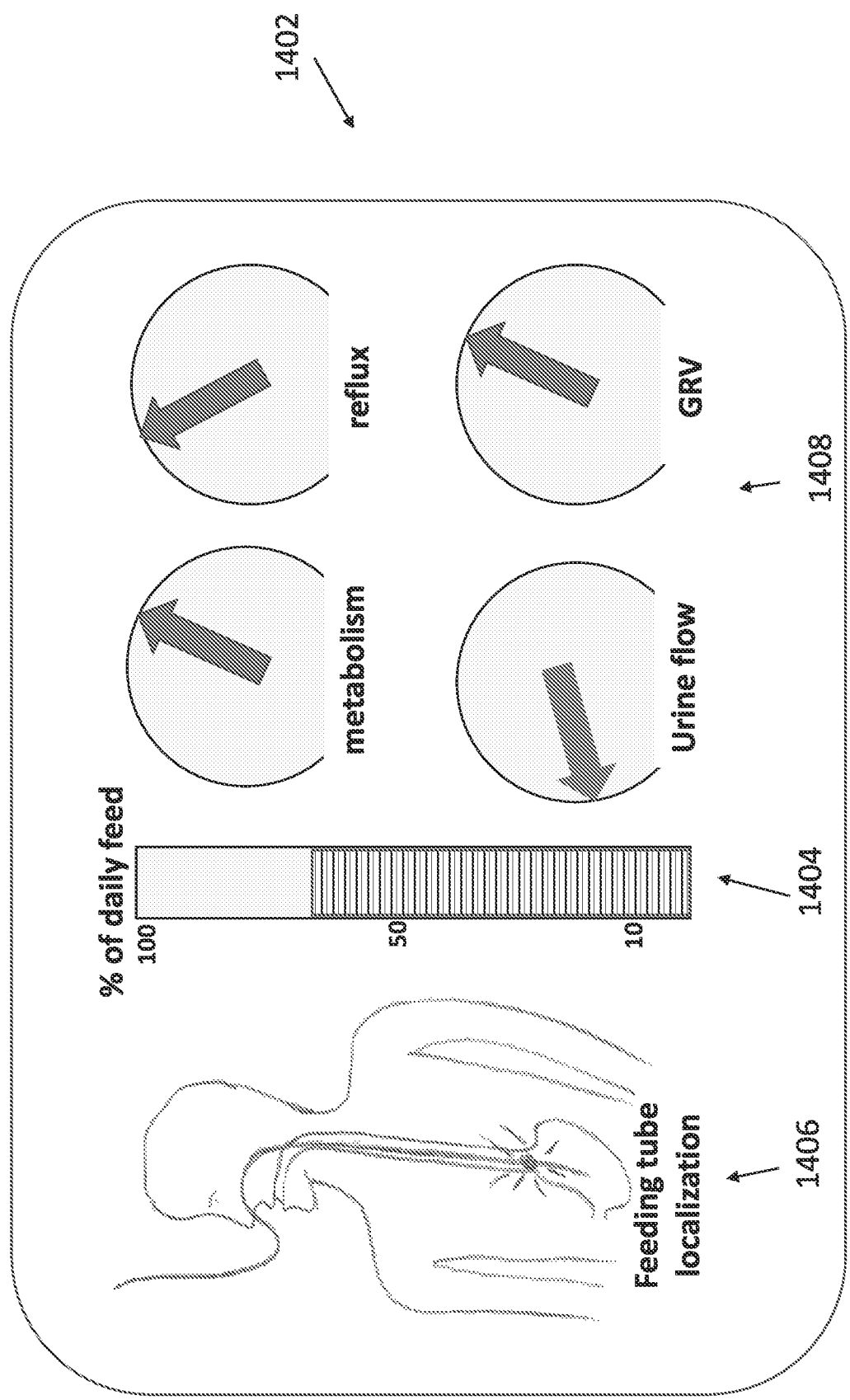
FIG. 13, which is a schematic of an exemplary GUI presenting an overall patient status, in accordance with some embodiments of the present invention.

Reference is now made to FIG. 13, which is a schematic of an exemplary GUI 1402 presenting an overall patient status, in accordance with some embodiments of the present invention. GUI 1402 provides a fast patient status observation monitor screen. GUI 1402 is designed to provide a snap shot and/or quick view of the patient status. GUI 1402 may be displayed on a monitor as a default image capable of alerting the care takers in case of deteriorating clinical indicators.

GUI 1402 may be presented as a dashboard, with one or more of the following exemplary regions:

Vertical bar(s) 1404 indicating, for example, the baseline feeding (i.e, representing actual feeding) as a percentage of the target feeding (e.g., in terms of real time rate), accumulated baseline feeding profile (i.e., actual amount of feedings provided to the patient) as percentage of target nutritional goal, i.e., how much of the total daily target the patient has already received, and accumulated baseline feeding profile as percentage of target feeding profile—which represents the patient's nutritional deficit which may be restored by increased feeding rates as decried herein. The vertical bar is one example implementation, for example, the percentage may be presented as a value, as a bar graph, and/or color coded to indicate whether the percentage is significant or not (e.g., green when within an allowed tolerance, and red when the percentage falls outside the allowed tolerance indicating insufficient feeding).

Graphic 1406 indicating current location of the feeding tube and/or indication of whether the tube is in the correct place. The graphic may include the esophagus and stomach, and a tube positioned within the esophagus and/or stomach according to tube location (e.g., based on impedance sensor measurements located on the distal end region of the feeding tube).

Circular dials 1408 presenting key parameter, for example, GRV, reflux, urine flow, metabolism, and/or other parameters described herein. Dials 1408 provide an indication of whether the values of the parameters are within normal, for example, a pointer within a vertical sector indicates normal values, and deviation clockwise or anti-clockwise indicates abnormal values. It is noted that dials are examples, for example, numerical values may be presented and/or the dials and/or values and/or other graphical elements may be color coded to indicate whether the respective values are within defined targets (e.g., normal, healthy, desired values) or not.

It is noted that values depicted by GUI 1402 may be fed into the model(s) as described herein. For example, location of feeding tube, metabolism, and urine flow may be fed as additional gastric parameters (over the reflux, GRV and/or actual feedings) into the model for predicting risk of reflux and/or adjusting the feeding rate.

Figure 14:
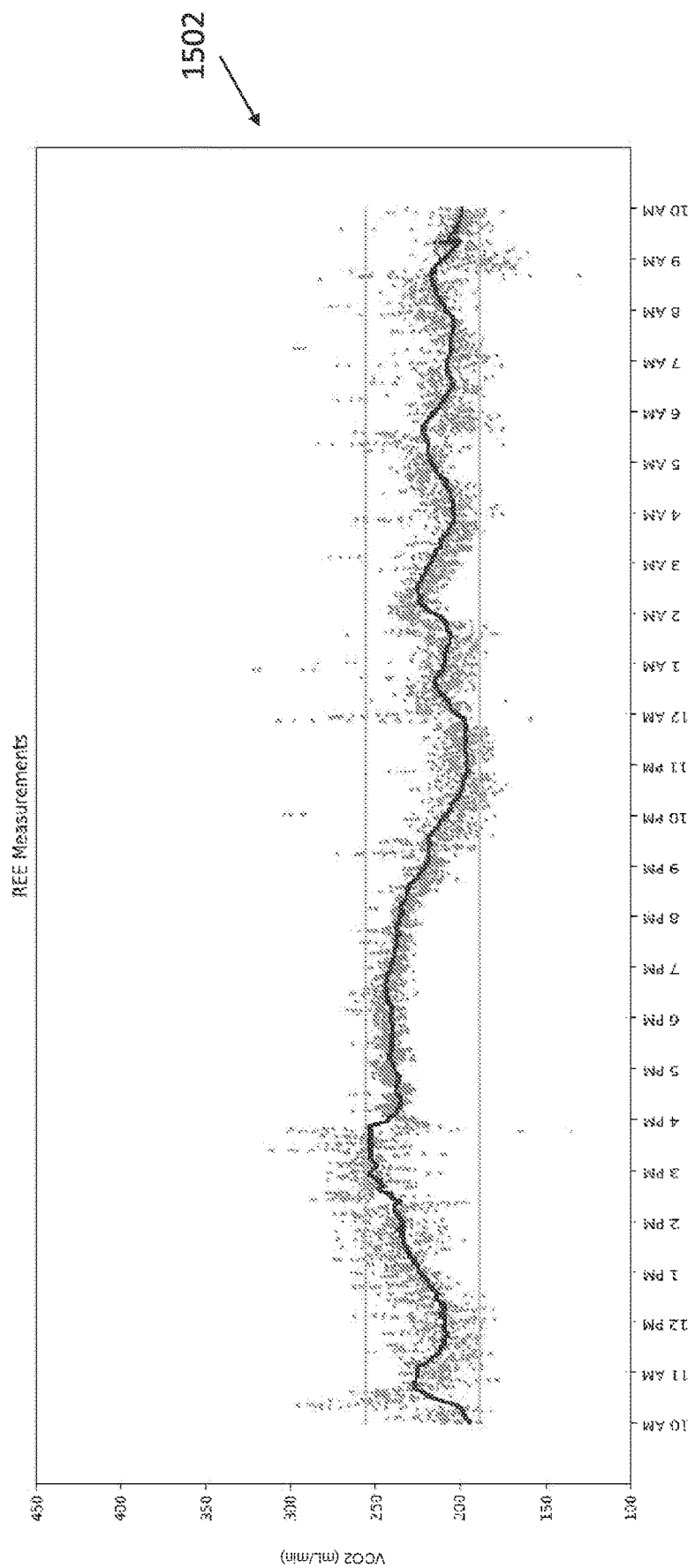
FIG. 14 is a graph of exemplary typical $CO_2$ production rates, in accordance with some embodiments of the present invention.

Reference is now made to FIG. 14, which is a graph 1502 of exemplary typical $CO_2$ production rates (in milliliters per minute), in accordance with some embodiments of the present invention. The values of graph 1502 may be indicative of REE values, which may be used to select and/or adjust patient feeding rates, for example, as described herein. Values of graph 1502 have been obtained for a real patient.

Figure 15A:
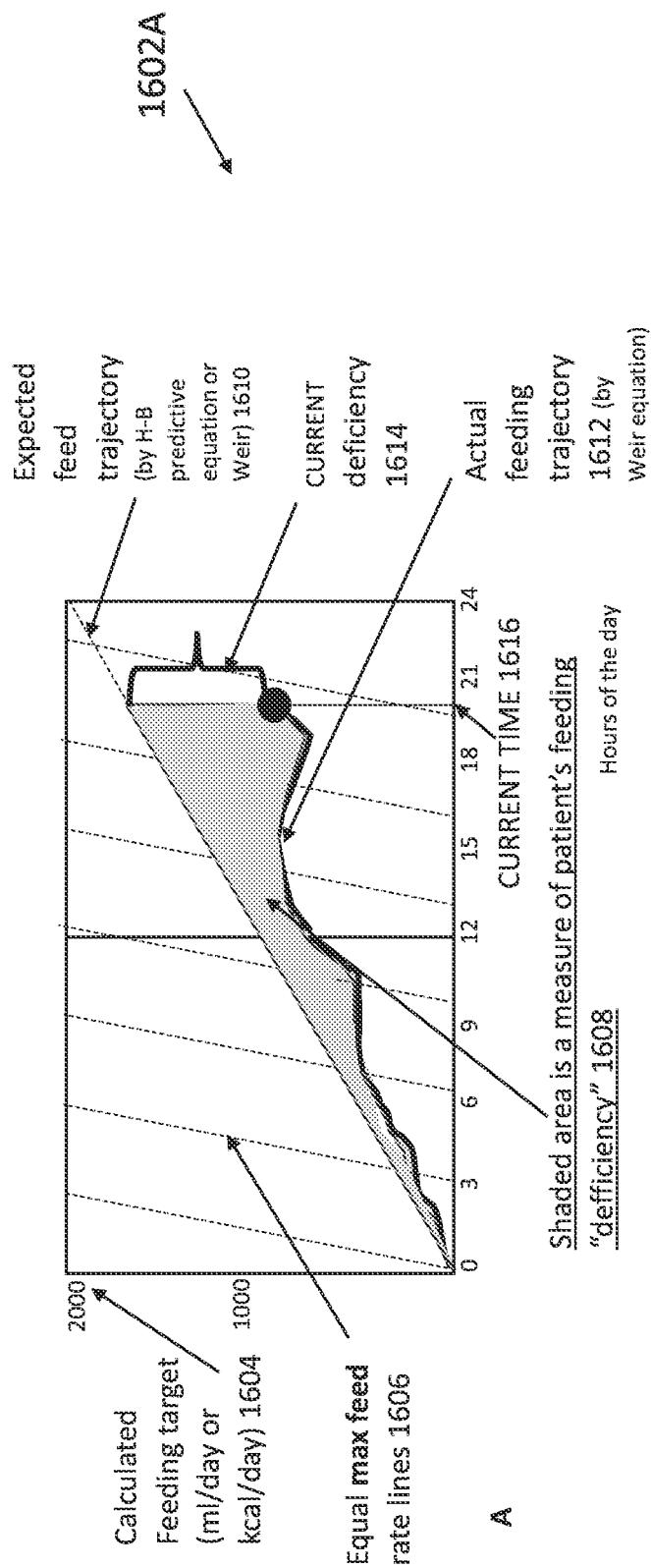

Reference is now made to FIG. 15A-15B which includes a graph 1602A and 1602B depicting an exemplary nutritional daily chart for a patient, summarizing exemplary important nutritional status of the patient, in accordance with some embodiments of the present invention. Graph 1602 of FIG. 15B provides more details over graph 1602A of FIG. 15A. Following the feeding progress track is an important early indicator of approaching organ crash. Portions of graphs 1602A-B may be computed and/or adjusted, for example, as described herein, for example, based on the model described herein.

1604 is a y-axis indicating the amount of feeding relative to time (on x-axis 1616) relative to a Calculated Feeding target (e.g., in ml/day or kcal/day), as described herein.

1606 indicates an example of equal maximal feeding rate lines, defining maximal feeding rates, for example, as described herein.

1608 is a marked region (e.g., shaded, color coded, marked with an indication such as arrow and/or text) between expected feed trajectory 1610, i.e., target feeding profile (e.g., computed by H-B and/or Weir and/or other predictive equations, for example, as described herein) and actual feeding trajectory 1612, i.e., baseline feeding profile (e.g., computed by Weir, for example, as described herein). Feeding halts are depicted as straight segments of curve 1612 indicating no feeding has been provided to the patient. Feeding halts may occur, for example, events 1650 and 1652 depicted in FIG. 15B. Feeding halts may be due to, for example, due to treatments performed on the patient and/or medical procedures (e.g., x-ray). Current deficiency 1614 is computed, for a value along the current time axis 1616, as a difference between the corresponding values of curve 1610 and 1612. Shaded region 1608 may represent a buildup of nutritional deficiency occurring over the feeding time interval. The size of shaded region 1608 indicates the amount of deficiency, for example, indicative of risk of organ collapse.

The feeding target and/or the corresponding feeding trajectory may be calculated according to the equation to match the patient's REE & EEE (e.g., as described herein) and/or adjusted and/or computed using the model described herein.

Graph 1602 of FIG. 15B shows an example of: a halt event 1650, a halt event with GRV 1652, basal rate 1654, max (i.e., recovery) feeding rate 1656, actual feed trajectory 1658, expected feed trajectory 1660, long halt event 1662, day end deficiency 1664, and calculated feeding target 1666.

Figure 15C:
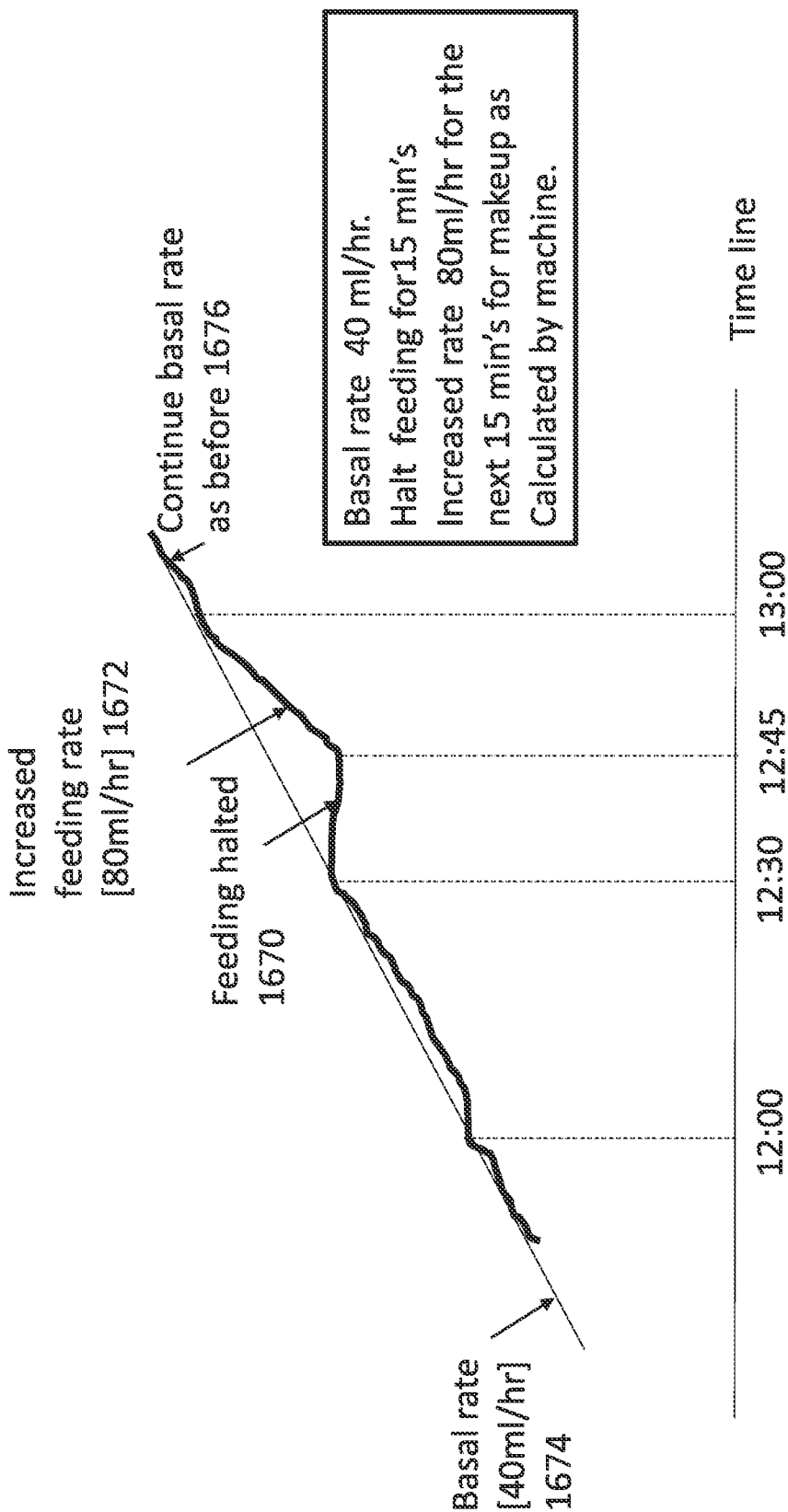
FIG. 15C is a graph depicting an example of a halt in feeding, which is compensated for by automatically increasing the feeding rate, in accordance with some embodiments of the present invention.

Reference is now made to FIG. 15C, which is a graph depicting an example of a halt in feeding 1670, which is compensated for by automatically increasing the feeding rate (e.g., instructing a pump to increase the pumping rate) 1672 (i.e., adjustment to the baseline feeding profile) to reach a defined basal rate (i.e., target feeding profile) 1674, in accordance with some embodiments of the present invention. Once the deficiency between actual feeding (based on the baseline feeding profile) and target feeding profile substantially match, the baseline feeding profile is set to the target feeding profile 1676. For example, the basal rate 1674 (i.e., target feeding profile) is initially set to 40 ml/hour (e.g., as described herein). The feeding is halted 1670 for 15 minutes (e.g., for reasons as described herein), which creates a deficit in feeding (i.e., gap between baseline feeding profile and target feeding profile). The baseline feeding profile is adjusted to 80 ml/hour 1672 to close the deficit. The baseline feeding profile is adjusted to match the target feeding profile 1676 of 40 ml/hour.

Figure 15D:
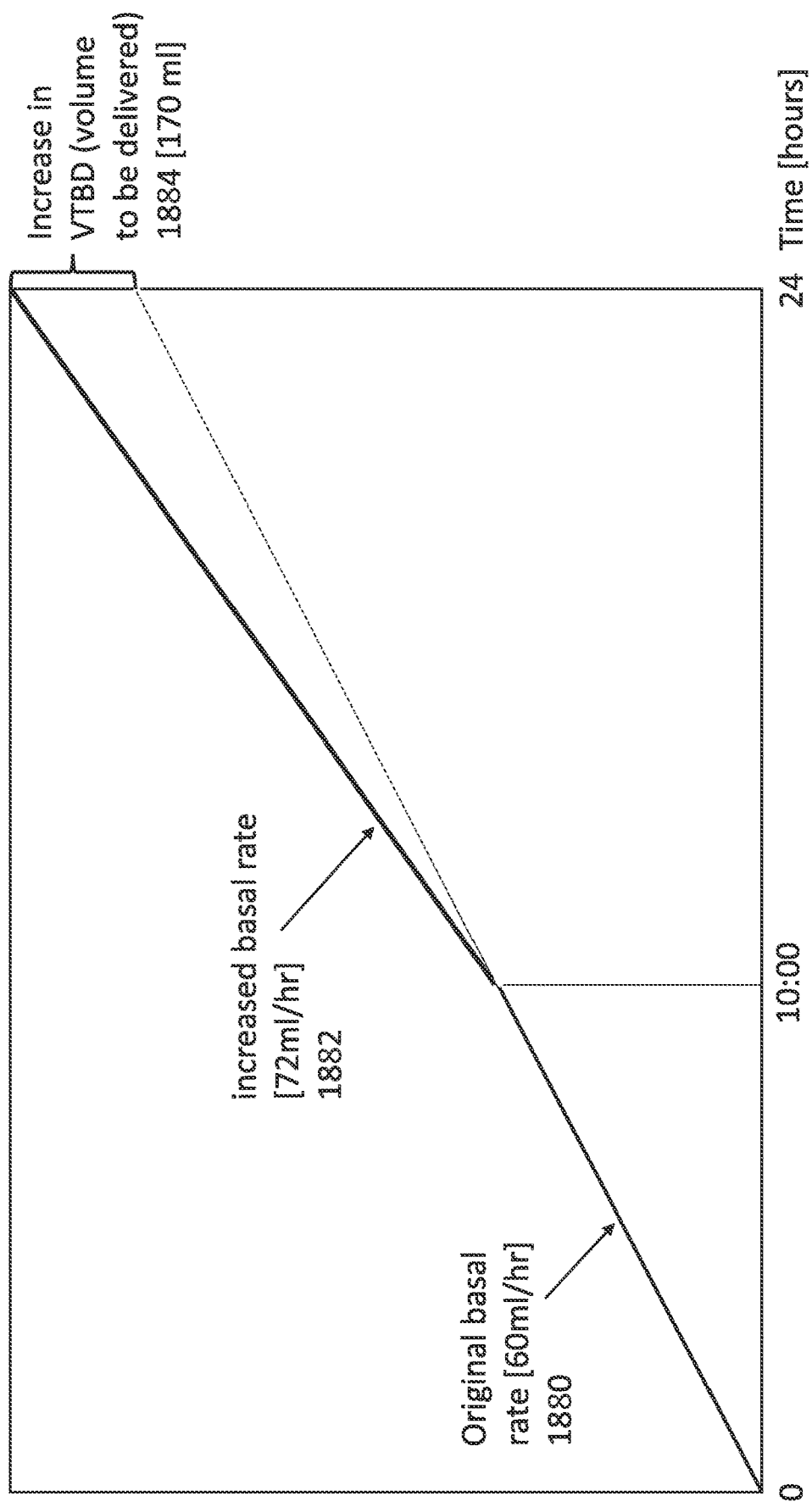
FIG. 15D is a graph depicting an example of a change in the target feeding profile, in accordance with some embodiments of the present invention.

Reference is now made to FIG. 15D, which is a graph depicting an example of a change in the target feeding profile, in accordance with some embodiments of the present invention. The original basal rate 1870 (i.e., target feeding profile) is set to 60 ml/hour. At 10:00 Am, the basal rate increases 1872 to 72 ml/hour (i.e., target feeding profile is adjusted). The baseline feeding profile, which is set to match the target feeding profile, is adjusted accordingly. It is noted that the increase in VTBD 1874 for the 24 hour time interval increases from 1440 to 1610 ml, i.e., increase of 170 ml.

It is noted that the feeding rate may be increased to a higher rate, up to the maximal rate. The maximal rate may be selected according to likelihood of the patient refluxing the enteral feeding being below a threshold, for example, computed by the model(s). The maximal rate may be set as the maximal rate that the patient can tolerate without refluxing, optionally determined based on feeding rate that the patient can tolerate without refluxing and/or the maximal volume that the patient can tolerate without refluxing.

Figure 17:
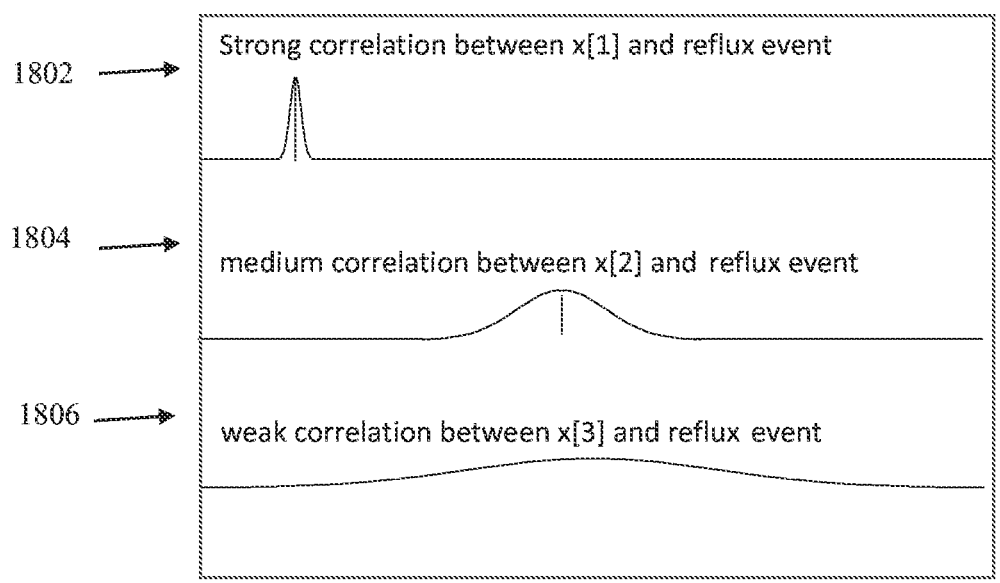
FIG. 17, which is a schematic that graphically depicts correlations between parameters and reflux events, in accordance with some embodiments of the present invention.

Reference is now made to FIG. 17, which is a schematic that graphically depicts correlations between parameters and reflux events, in accordance with some embodiments of the present invention. Schematic 1802 depicts a strong correlation between parameter denoted x[1] and a reflux event, via a high defined peak. Schematic 1804 depicts a medium correlation between parameter denoted x[2] and a reflux event, via a more spread out but still defined and medium high peak. Schematic 1806 depicts a weak correlation between parameter denoted x[3] and a reflux event via a speak out and not well defined and low peak.

Patient clinical parameters for which a strong reflux correlation has been calculated (e.g., based on accumulated data), as described herein, for example, with reference to FIG. 5 are identified. For example, correlation values above a threshold (e.g., 0.7, 0.8, 0.9, or other value) represent strong correlation between a parameter and reflux event, mathematically denoted as $\rho[1] > 0.8$, $\rho[2] > 0.8$ . . . for parameters x[1], x[2] . . . .

The parameters highly correlated with reflux may be accounted for (e.g., automatically, and/or manually by the user). For example, when the parameter associated with patient maneuvering has been shown to be induce reflux (i.e., via high correlation factor above the threshold) feeding may be halted (e.g., manually and/or automatically) before maneuvering the patient to reduce the possibility of reflux.

Detecting the correlation between reflux incidents and the patient's parameters and/or treatment may be performed as described herein, and/or for example, as follows: Whenever a reflux event is observed (denoted Y=1) the said parameter levels are recorded. As time passes the accumulated data indicate the level of influence the parameters have on the reflux.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant computing devices and enteral feeding controllers will be developed and the scope of the terms computing devices and enteral feeding controllers are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A system for automated enteral feeding of a subject, comprising:
at least one hardware processor executing a code for:
measuring, over a portion of a time interval, a resting energy expenditure (REE) of the subject based on $CO_2$ production rate and/or $O_2$ consumption rate estimates of the subject made by measurements of at least one sensor;
computing a target nutritional goal to reach at an end of the time interval, wherein the target nutritional goal comprises a volume to be delivered (VTBD) by the end of the time interval that matches to a target amount of energy expenditure of the subject over the time interval computed by extrapolating the REE from the portion to the time interval;
computing a target feeding profile defining a target feeding delivery rate that is up to a defined maximal feeding delivery rate for enteral feeding of the subject by an automated enteral feeding device for reaching the VTBD by the end of the time interval;
continuously monitoring the real time energy expenditure of the subject over the time interval based on continuous measurements of the REE measurements computed from $CO_2$ production rate and/or $O_2$ consumption rate estimates of the subject made by measurements of the at least one sensor;
dynamically adapting the target nutritional goal and corresponding VTBD to compute a maximum VTBD (max VTBD) to reach at the end of the time interval according to dynamic adaptations of the monitored real time energy expenditure of the subject;
dynamically sending a control signal to the automated enteral feeding device that automatically delivers feedings to the subject for adapting the target feeding delivery rate and the corresponding target feeding profile for a remaining portion of the time interval for reaching the max VTBD by the end of the time interval, wherein the target feeding profile matches to changes of the REE and does not exceed the defined maximal feeding delivery rate.

2. The system of claim 1, further comprising code for: selecting an optimal feeding formulation from a plurality of in-stock pre-prepared clinical feeding formulations, wherein the target feeding profile is computed according to the optimal feeding formulation.

3. The system of claim 2, further comprising code for: computing an optimal protein nutritional goal to reach at the end of the time interval;
computing a protein deficit between the optimal protein nutritional goal and the optimal feeding formulation; and
generating instructions for adding an amount of protein corresponding to the protein deficit to the optimal feeding formulation.

4. The system of claim 3, wherein the optimal protein nutritional goal is selected based on a medical state of the subject.

5. The system of claim 2, wherein the optimal feeding formulation is selected to provide 100% or near 100% within a tolerance range of the target nutritional goal.

6. The system of claim 2, wherein the plurality of in-stock pre-prepared clinical feeding formulations are filtered to exclude formulations unsuitable for the subject according to a medical state of the subject.

7. The system of claim 6, wherein excluded formulations are selected from a group consisting of: low fiber content, high fiber content, include nourishments unsuitable for diabetics, and include nourishments unsuitable for cardiovascular disease.

8. The system of claim 1, further comprising code for: obtaining an amount of hidden calories carried by medications prescribed for the subject for administration by the end of the time interval;
adjusting the target feeding profile to take into account the amount of hidden calories.

9. The system of claim 1, wherein the target nutritional goal comprises a preceding nutritional goal and the time interval comprises a preceding time interval, and further comprising computing a next target nutritional goal for a next time interval adding to a next target time nutritional goal to reach at an end of a next time interval, an amount equal to the preceding feeding deficit between the preceding nutritional goal and total feedings delivered over the preceding time interval.

10. A system for automated enteral feeding of a subject, comprising:
at least one hardware processor executing a code for:
computing a target feeding profile denoting a target enteral feeding of the subject by an automated enteral feeding device for reaching a target nutritional goal at the end of a time interval;
defining a baseline feeding profile of a subject by matching to the target feeding profile, wherein the subject is automatically fed by the automated enteral feeding device according to the baseline feeding profile for reaching the target nutritional goal;
pausing or slowing down the enteral feeding by the automated enteral feeding device for at least one pause time interval;
wherein a feeding deficit is formed between the target feeding profile and the baseline feeding profile during each pause time interval, the feeding deficit denoting a deficit to reach the target nutritional goal at the end of the time interval; and
adjusting the baseline feeding profile to a higher feeding delivery rate that is higher than a feeding delivery rate of the corresponding target feeding profile to compensate the feeding deficit for reaching the target nutritional goal at the end of the time interval.

11. The system of claim 10, further comprising code for: measuring, over a portion of the time interval, a resting energy expenditure (REE) of the subject based on $CO_2$ production rate and/or $O_2$ consumption rate estimates of the subject made by measurements of at least one sensor;

computing the target nutritional goal to reach at an end of the time interval, the target nutritional goal matching to a target amount of energy expenditure of the subject over the time interval computed by extrapolating the REE from the portion to the time interval.

12. The system of claim 10, further comprising code for:

detecting when the feeding deficit between the target feeding profile and the baseline feeding profile has been eliminated, when a gap indicating a difference the baseline feeding profile indicating total accumulated feedings actually administered to the patient matches the target feeding profile indicating total accumulated desired feeding; and reducing the baseline feeding profile to match the target feeding profile.

13. The system of claim 10, wherein a maximum feeding delivery rate defied by the baseline feeding profile is set according to a basal metabolic rate of the subject.

14. The system of claim 10, further comprising code for:

selecting an optimal feeding formulation from a plurality of in-stock pre-prepared clinical feeding formulations, wherein the target feeding profile is computed according to the optimal feeding formulation.

15. The system of claim 14, further comprising code for:

computing an optimal protein nutritional goal to reach at the end of the time interval;

computing a protein deficit between the optimal protein nutritional goal and the optimal feeding formulation; and generating instructions for adding an amount of protein corresponding to the protein deficit to the optimal feeding formulation.

16. The system of claim 15, wherein the optimal protein nutritional goal is selected based on a medical state of the subject.

17. The system of claim 14, wherein the optimal feeding formulation is selected to provide 100% or near 100% within a tolerance range of the target nutritional goal.

18. The system of claim 14, wherein the plurality of in-stock pre-prepared clinical feeding formulations are filtered to exclude formulations unsuitable for the subject according to a medical state of the subject.

19. The system of claim 10, wherein excluded formulations are selected from a group consisting of: low fiber content, high fiber content, include nourishments unsuitable for diabetics, and include nourishments unsuitable for cardiovascular disease.

20. The system of claim 10, further comprising code for:

obtaining an amount of hidden calories carried by medications prescribed for the subject for administration by the end of the time interval;

adjusting the target feeding profile to take into account the amount of hidden calories.

* * * * *